(12) United States Patent
Karicherla et al.

(10) Patent No.: US 12,605,536 B2
(45) Date of Patent: Apr. 21, 2026

(54) THIN FILM ELECTRODES FOR BRAIN COMPUTER INTERFACE AND METHODS OF MICROFABRICATING

(71) Applicant: Verily Life Sciences LLC, South San Francisco, CA (US)

(72) Inventors: Annapurna Karicherla, South San Francisco, CA (US); Bo Lu, South San Francisco, CA (US); Kedar Shah, San Francisco, CA (US); Peng Cong, South San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 797 days.

(21) Appl. No.: 17/912,478

(22) PCT Filed: Mar. 18, 2021

(86) PCT No.: PCT/US2021/023013
§ 371 (c)(1),
(2) Date: Sep. 16, 2022

(87) PCT Pub. No.: WO2021/188824
PCT Pub. Date: Sep. 23, 2021

(65) Prior Publication Data
US 2023/0158294 A1     May 25, 2023

Related U.S. Application Data

(60) Provisional application No. 62/991,524, filed on Mar. 18, 2020.

(51) Int. Cl.
| | |
|---|---|
| *A61N 1/05* | (2006.01) |
| *G06F 3/01* | (2006.01) |
| *H01B 7/08* | (2006.01) |

(52) U.S. Cl.
CPC .......... *A61N 1/0529* (2013.01); *G06F 3/015* (2013.01); *H01B 7/0846* (2013.01)

(58) Field of Classification Search
None
See application file for complete search history.

(56) References Cited

U.S. PATENT DOCUMENTS

| | | | |
|---|---|---|---|
| 7,319,906 B2 * | 1/2008 | Kuzma | ................ A61N 1/0541 |
| | | | 607/137 |
| 10,391,312 B2 * | 8/2019 | Mowery | ............ A61N 1/36034 |

(Continued)

OTHER PUBLICATIONS

Application No. PCT/US2021/023013 , International Search Report and Written Opinion, Mailed on Jul. 8, 2021, 8 pages.

*Primary Examiner* — Mallika D Fairchild
(74) *Attorney, Agent, or Firm* — Kilpatrick Townsend & Stockton LLP

(57) ABSTRACT

The present disclosure relates to a monolithic thin-film lead assembly and methods of microfabricating a monolithic thin-film lead assembly. Particularly, aspects of the present disclosure are directed to a monolithic thin-film lead assembly that includes a cable having a proximal end, a distal end, a supporting structure that extends from the proximal end to the distal end, and conductive traces formed on a portion of the supporting structure. The supporting structure includes one or more layers of dielectric material. The monolithic thin-film lead assembly further includes an interface formed on the supporting structure at the distal end of the cable. The interface includes electrodes and/or sensors in electrical connection with the conductive traces, and the supporting structure has at least one curved portion disposed between a first set of electrodes and a second set of electrodes, and/or between a first set of sensors and a second set of sensors.

16 Claims, 32 Drawing Sheets

(56) References Cited

U.S. PATENT DOCUMENTS

| | | | |
|---|---|---|---|
| 10,631,749 B2* | 4/2020 | Rubenstein | A61B 18/1492 |
| 2012/0306076 A1 | 12/2012 | Hsu | |
| 2013/0289686 A1* | 10/2013 | Masson | A61N 1/056 |
| | | | 607/122 |
| 2015/0142010 A1* | 5/2015 | Min | A61N 1/0551 |
| | | | 607/116 |
| 2016/0144078 A1* | 5/2016 | Young | A61B 5/24 |
| | | | 607/116 |
| 2016/0220812 A1* | 8/2016 | Bottomley | B29C 33/126 |
| 2018/0169406 A1 | 6/2018 | Shah et al. | |
| 2018/0235495 A1* | 8/2018 | Rubenstein | A61B 5/00 |
| 2019/0308018 A1* | 10/2019 | Petoe | A61N 1/0543 |

* cited by examiner

100

105
135
130
170
180
110
125
120
370
115
175
155

160

External Device

140

Electrodes

1235
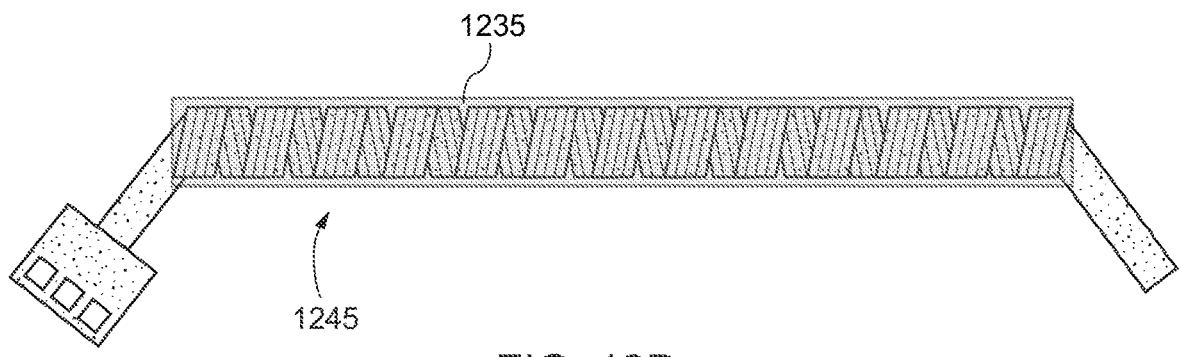
1245
FIG. 12D
1250          1235
1255
FIG. 12E
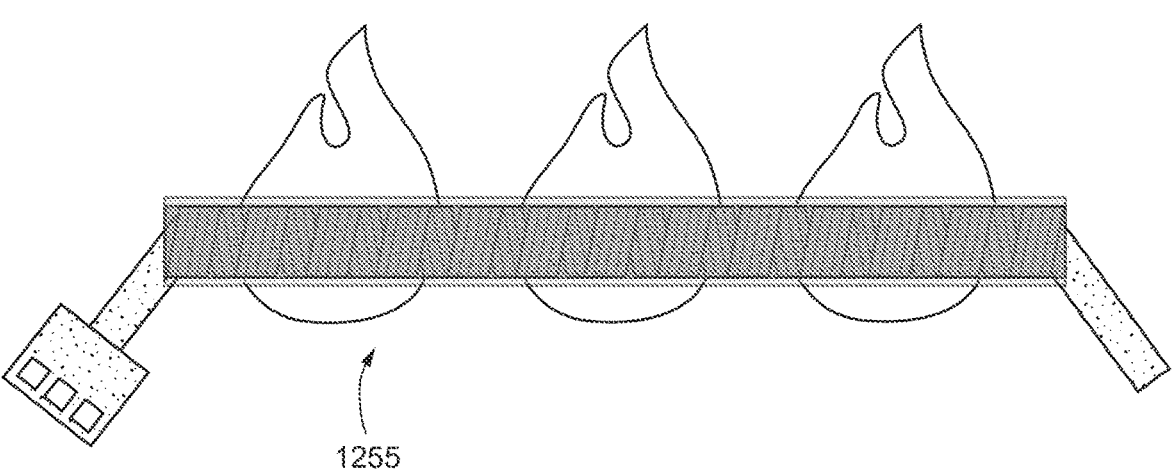
1255
FIG. 12F

1455

1460

THIN FILM ELECTRODES FOR BRAIN COMPUTER INTERFACE AND METHODS OF MICROFABRICATING

CROSS-REFERENCE TO RELATED APPLICATIONS

The present application is a U.S. National Stage of PCT application No. PCT/US2021/023013, filed on Mar. 18, 2021, which claims priority to U.S. Provisional Patent Application No. 62/991,524 filed on Mar. 18, 2020, both of which are incorporated herein by reference for all purposes in their entirety.

FIELD OF THE INVENTION

The present disclosure relates to implantable neuromodulation devices and methods of fabrication, and in particular to a monolithic thin-film lead assembly and methods of microfabricating a monolithic thin-film lead assembly.

BACKGROUND

Normal neural activity is an intricate balance of electrical and chemical signals, which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems that deliver electrical, chemical or other agents to reversibly modify brain and nerve cell activity. The most common neuromodulation therapy is spinal cord stimulation to treat chronic neuropathic pain. In addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis; gastric and colonic stimulation for gastrointestinal disorders such as dysmotility or obesity; vagus nerve stimulation for epilepsy, obesity or depression; carotid artery stimulation for hypertension, and spinal cord stimulation for ischemic disorders such as angina and peripheral vascular disease.

Neuromodulation devices and systems tend to have a similar form factor, derived from their predecessors, e.g. the pacemaker or defibrillator. Such neuromodulation devices and systems typically consist of an implant comprising a neurostimulator having electronics connected to a lead assembly that delivers electrical pulses to electrodes interfaced with nerves or nerve bundles via an electrode assembly. The lead assembly is typically formed of a conductive material and takes the form of an insulated wire connected to the electrodes via a first connector on one end (e.g., a distal end) and the electronics of the neurostimulator via a second connector on another end (e.g., a proximal end). In some instances (e.g., deep implants), the lead assembly comprises additional conductors and connectors such as extension wires or a cable connected via connectors between the electrodes and the electronics of the neurostimulator.

Conventional electrodes, conductors, and connectors are separate components typically connected to one another using various coupling means for maintaining electrical conductivity between the connected components. For example, the extension conductors of the lead assembly may be secured to a neurostimulator using a connector having set screws or spring-lock mechanisms, the extension conductors may be secured to the lead conductors using another connector having set screws or spring-lock mechanisms or using techniques such as welding or bonding (e.g., using solder or an adhesive), and the lead conductors may be connected to the electrodes using techniques such as welding or bonding. However, in the absence of hardware migration, the main reason for malfunction of the electrical neuromodulation system is disconnections and fractures of system components. These problems can occur in all types of conventional electrodes, conductors, and connectors. For example, in deep brain stimulation, most fractures occur due to migration of the extension connector between the electrode and the extension conductor. Conventionally, the incidence of fracture between components has been decreased by using improved surgical techniques such as implant and placement of the extension connector as proximal as possible to the stimulating or recording electrode. In view of these factors, it may be desirable to develop neuromodulation devices and systems that are capable of having design flexibility, and desirable mechanical properties to mitigate disconnections and fractures of system components.

BRIEF SUMMARY

In various embodiments, a monolithic thin-film cable assembly is provided that includes a proximal end; a distal end; and a supporting structure that extends from the proximal end to the distal end. The supporting structure is comprised of one or more layers of dielectric material that have a thickness from 10 μm to 150 μm. The monolithic thin-film cable assembly further includes a plurality of conductive traces formed on a portion of the supporting structure. The conductive traces have a thickness from 0.5 μm to 100 μm. The monolithic thin-film cable may have a spiral shape comprising two or more turns and a pitch between each of the turns from 10 μm to 1 cm.

In some embodiments, the plurality of conductive traces extend from the proximal end to the distal end. Optionally, a length of the supporting structure is from 5 cm to 150 cm. Optionally, a width of the supporting structure is from 25 μm to 5 mm. In some embodiments, the dielectric material is polyimide, liquid crystal polymer, parylene, polyether ether ketone, or a combination thereof. Optionally, a length of the plurality of conductive traces is from 5 cm to 150 cm. Optionally, a width of the plurality of conductive traces is from 2.0 μm to 500 μm.

In some embodiments, the plurality of conductive traces are comprised of one or more layers of conductive material, and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof. In some embodiments, a coefficient of thermal expansion for the plurality of conductive traces is approximately equal to a coefficient of thermal expansion for the supporting structure.

In various embodiments, a monolithic thin-film lead assembly is provided that includes a cable comprising a proximal end, a distal end, a supporting structure that extends from the proximal end to the distal end, and a plurality of conductive traces formed on a portion of the supporting structure. The supporting structure is comprised of one or more layers of dielectric material. The monolithic thin-film lead assembly further includes an electrode assembly formed on the supporting structure at the distal end of the cable. The electrode assembly comprises one or more electrodes in electrical connection with one or more conductive traces of the plurality of conductive traces.

In some embodiments, a thickness of the supporting structure is from 10 μm to 150 μm. In some embodiments, the plurality of conductive traces have a thickness from 0.5 μm to 100 μm. In some embodiments, a length of the supporting structure is from 5 cm to 150 cm. In some embodiments, the dielectric material is polyimide, liquid crystal polymer, parylene, polyether ether ketone, or a combination thereof. In some embodiments, a length of the plurality of conductive traces is from 5 cm to 150 cm.

In some embodiments, the plurality of conductive traces are comprised of one or more layers of conductive material, and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof. In some embodiments, a coefficient of thermal expansion for the plurality of conductive traces is approximately equal to a coefficient of thermal expansion for the supporting structure.

In some embodiments, the monolithic thin-film lead assembly further includes a connector formed on the supporting structure at the proximal end of the cable and in electrical connection with the one or more conductive traces of the plurality of conductive traces. In some embodiments, the connector comprises one or more bond or contact pads. In some embodiments, a portion of the cable is helical. Optionally, the helical portion of the cable comprises a pitch from 100 μm to 2 mm. Optionally, the helical portion of the cable comprises a pitch from 200 μm to 400 μm. Optionally, the helical portion of the cable comprises a pitch from 600 μm to 1600 μm. Optionally, the helical portion of the cable comprises a helix angle from 10° to 85°. Optionally, the helical portion of the cable comprises a helix angle from 40° to 65°. Optionally, the helical portion of the cable is wound in a clockwise direction or an anti-clockwise direction.

In some embodiments, the monolithic thin-film lead assembly further includes a housing encasing the portion of the supporting structure having the plurality of conductive traces. In some embodiments, the monolithic thin-film lead assembly further includes a housing encasing the helical portion of the cable. In some embodiments, the housing is comprised of a medical grade polymer material. Optionally, the medical grade polymer material is silicone, a polymer dispersion, parylene, or a polyurethane.

In various embodiments, a neuromodulation system is provided including a neurostimulator comprising an electronics module; and a cable comprising a supporting structure and a plurality of conductive traces formed on a portion of the supporting structure. The supporting structure is comprised of one or more layers of dielectric material. The neuromodulation system further includes an electrode assembly formed on the supporting structure. The electrode assembly comprises one or more electrodes in electrical connection with one or more conductive traces of the plurality of conductive traces; and a connector formed on the supporting structure and in electrical connection with the one or more conductive traces of the plurality of conductive traces. The connector electrically connects the one or more conductive traces of the plurality of conductive traces to the electronics module.

In some embodiments, a portion of the cable is helical. Optionally, the helical portion of the cable comprises a pitch from 100 μm to 2 mm. Optionally, the helical portion of the cable comprises a helix angle from 10° to 85°.

In some embodiments, the neuromodulation system further includes a housing encasing the portion of the supporting structure having the plurality of conductive traces. In some embodiments, the neuromodulation system further includes a housing encasing the helical portion of the cable. In some embodiments, the housing is comprised of a medical grade polymer material. Optionally, the medical grade polymer material is silicone, a polymer dispersion, parylene, or a polyurethane.

In various embodiments, a monolithic thin-film lead assembly is provided including a cable comprising: a first helical portion at a proximal end of the cable, the first helical portion having a pitch from 200 μm to 400 μm, a second helical portion at a distal end of the cable, the second helical portion having a pitch from 200 μm to 400 μm, a third helical portion that extends between the first helical portion and the second helical portion, the middle portion being a third helical portion with a pitch from 600 μm to 1600 μm, a supporting structure that extends from the proximal end to the distal end, and a plurality of conductive traces formed on a portion of the supporting structure; and an electrode assembly formed on the supporting structure at the distal end of the cable, where the electrode assembly comprises one or more electrodes in electrical connection with one or more conductive traces of the plurality of conductive traces.

In some embodiments, the monolithic thin-film lead assembly further includes a first portion of an housing formed coplanar with the first helical portion. In some embodiments, the first portion of the housing is comprised of a thermoplastic or thermosetting polymer. In some embodiments, the monolithic thin-film lead assembly further includes a second portion of an housing formed coplanar with the second helical portion. In some embodiments, the second portion of the housing is comprised of a thermoplastic or thermosetting polymer. In some embodiments, the monolithic thin-film lead assembly further includes a third portion of the housing completely encasing the third helical portion. In some embodiments, the third portion of the housing is comprised of silicone.

In some embodiments, the monolithic thin-film lead assembly further includes a multiplexer chip formed on the supporting structure at the proximal end or the distal end, the multiplexer chip in electrical connection with the one or more electrodes via the one or more conductive traces of the plurality of conductive traces.

In some embodiments, a thickness of the supporting structure is from 10 μm to 150 μm. In some embodiments, the plurality of conductive traces have a thickness from 0.5 μm to 100 μm. In some embodiments, a length of the supporting structure is from 5 cm to 150 cm. In some embodiments, the supporting structure is comprised of one or more layers of dielectric material that is polyimide, liquid crystal polymer, parylene, polyether ether ketone, or a combination thereof. In some embodiments, a length of the plurality of conductive traces is from 5 cm to 150 cm.

In some embodiments, the plurality of conductive traces are comprised of one or more layers of conductive material, and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof.

In various embodiments, a monolithic thin-film lead assembly comprises a cable comprising: a helical portion that extends between a proximal end and a distal end of the cable, the helical portion having a pitch from 600 μm to 1600 μm, a supporting structure that extends from the proximal end to the distal end of the cable, and a plurality of conductive traces formed on a portion of the supporting structure; and an electrode assembly formed on the supporting structure at the distal end of the cable. The electrode assembly comprises one or more electrodes in electrical connection with one or more conductive traces of the plurality of conductive traces.

In some embodiments, the monolithic thin-film lead assembly further includes a housing completely encasing the first helical portion, where the housing is comprised of silicone. In some embodiments, the electrode assembly further comprises one or more sensors in electrical connection with one or more conductive traces of the plurality of conductive traces. In some embodiments, the electrode assembly is a cuff electrode assembly. In some embodiments, the supporting structure at the distal end of the cable having the electrode assembly formed thereon is thermoformed into a cuff structure.

In some embodiments, the monolithic thin-film lead assembly further includes a connector formed on the supporting structure at the proximal end of the cable and in electrical connection with the one or more conductive traces of the plurality of conductive traces. In some embodiments, the connector comprises one or more bond or contact pads. In some embodiments, the monolithic thin-film lead assembly further includes a multiplexer chip formed on the supporting structure at the proximal end or the distal end, the multiplexer chip in electrical connection with the one or more electrodes via the one or more conductive traces of the plurality of conductive traces. In some embodiments, a thickness of the supporting structure is from 10 μm to 150 μm. In some embodiments, the plurality of conductive traces have a thickness from 0.5 μm to 100 μm. In some embodiments, a length of the supporting structure is from 5 cm to 150 cm. In some embodiments, the supporting structure is comprised of one or more layers of dielectric material that is polyimide, liquid crystal polymer, parylene, polyether ether ketone, or a combination thereof. In some embodiments, a length of the plurality of conductive traces is from 5 cm to 150 cm.

In some embodiments, the plurality of conductive traces are comprised of one or more layers of conductive material, and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof.

In various embodiments, a method of manufacturing a monolithic thin-film lead assembly is provided that includes: forming a first polymer layer on a wafer or panel of substrate; forming a plurality of conductive traces on a first portion of the first polymer layer, where the forming the plurality of conductive traces comprises depositing a conductive material in a spiral pattern with two or more turns on the first portion of the first polymer layer; forming a wiring layer on a second portion of the first polymer layer, where the forming the wiring layer comprises depositing the conductive material in electrical contact with the plurality of conductive traces; depositing a second polymer layer on the wiring layer and the second portion of the first polymer layer; forming at least one electrode on the second polymer layer such that the at least one electrode is in electrical contact with at least a portion of a top surface of the wiring layer; and cutting the monolithic thin-film lead assembly from the first polymer layer, where the monolithic thin-film lead assembly comprises the plurality of conductive traces in the spiral pattern on the first polymer layer and the at least one electrode on the second polymer layer electrically connected to the plurality of conductive traces.

In some embodiments, the first polymer layer comprises one or more layers of dielectric material. In some embodiments, the dielectric material is polyimide, liquid crystal polymer, parylene, polyether ether ketone, or a combination thereof. In some embodiments, the second polymer layer comprises one or more layers of dielectric material. In some embodiments, the dielectric material is polyimide, liquid crystal polymer, parylene, polyether ether ketone, or a combination thereof.

In some embodiments, the method of manufacturing a monolithic thin-film lead assembly further includes forming contact vias in the second polymer layer to the wiring layer, where the forming the at least one electrode comprises: depositing a conductive material in the contact via and on a top surface of the second polymer layer, and patterning the conductive material to form: (i) a first electrode over a first region of the second polymer layer such that the first electrode is in contact with a first portion of the top surface of the wiring layer, and (ii) a second electrode over a second region of the second polymer layer such that the second electrode is in contact with a second portion of the top surface of the wiring layer.

In some embodiments, the first region and the second region of the second polymer layer are separated from one another by a third region of the second polymer layer that does include at least a portion of the wiring layer but does not include an electrode. In some embodiments, the method of manufacturing a monolithic thin-film lead assembly further includes depositing the second polymer layer on the plurality of conductive traces and the first portion of the polymer layer. In some embodiments, the method of manufacturing a monolithic thin-film lead assembly further includes detaching the monolithic thin-film lead assembly from the wafer or panel of substrate.

In various embodiments, a method of manufacturing a monolithic thin-film lead assembly is provided that includes: obtaining an initial structure comprising: (i) a cable comprising: a proximal end, a distal end, a supporting structure that extends from the proximal end to the distal end, and a plurality of conductive traces formed on a portion of the supporting structure; and (ii) an electrode assembly formed on the supporting structure at the distal end of the cable, where the electrode assembly comprises one or more electrodes in electrical connection with one or more conductive traces of the plurality of conductive traces; winding the portion of the supporting structure in a helical pattern on a mandrel; and heating the initial structure with the portion of the supporting structure wound in the helical pattern on the mandrel to form the monolithic thin-film lead assembly.

In some embodiments, the winding is controlled such that the helical pattern has a helix angle from 10° to 85° and a pitch from 100 μm to 2 mm. In some embodiments, the supporting structure is comprised of one or more layers of dielectric material, and a length of the supporting structure is from 5 cm to 150 cm. In some embodiments, the dielectric material is polyimide, liquid crystal polymer, parylene, polyether ether ketone, or a combination thereof. In some embodiments, a length of the plurality of conductive traces is from 5 cm to 150 cm.

In some embodiments, the plurality of conductive traces are comprised of one or more layers of conductive material, and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof.

In some embodiments, the obtaining the initial structure comprises: forming the supporting structure on a wafer or panel of substrate; forming the plurality of conductive traces on a first portion of the supporting structure; forming a wiring layer on a second portion of the supporting structure; depositing a polymer layer on the wiring layer and the second portion of the supporting structure; forming at least one electrode on the polymer layer such that the at least one electrode is in electrical contact with at least a portion of a top surface of the wiring layer; removing the wafer or panel of substrate from the supporting structure; and cutting the initial structure from the first polymer layer.

In various embodiments, a method of manufacturing a monolithic thin-film lead assembly is provided that includes: obtaining an initial structure comprising: (i) a cable comprising: a proximal end, a distal end, a supporting structure that extends from the proximal end to the distal end, and a plurality of conductive traces formed on a portion of the supporting structure; and (ii) an electrode assembly formed on the supporting structure at the distal end of the cable, where the electrode assembly comprises one or more electrodes in electrical connection with one or more conductive traces of the plurality of conductive traces; winding the portion of the supporting structure in a helical pattern on a mandrel; inserting the mandrel with the portion of the supporting structure into a polymer tube to form an intermediate structure; heating the intermediate structure with the portion of the supporting structure wound in the helical pattern on the mandrel to form the monolithic thin-film lead assembly; and removing the mandrel from the monolithic thin-film lead assembly. The polymer tube may completely encase the portion of the supporting structure wound in the helical pattern.

In some embodiments, the polymer tube is comprised of silicone, a polymer dispersion, parylene, or a polyurethane. In some embodiments, an inner diameter of the polymer tube is less than an outer diameter of the portion of the supporting structure wound in the helical pattern. In some embodiments, the method of manufacturing a monolithic thin-film lead assembly further includes soaking the polymer tube in a solution to swell the polymer tube prior to the insertion of the mandrel with the portion of the supporting structure wound in the helical pattern into the polymer tube. In some embodiments, the solution comprises heptane. In some embodiments, the heating process results in at least a portion of the portion of the supporting structure wound in the helical pattern embedding into a wall of the polymer tube since the inner diameter of the polymer tube is less than the outer diameter of the portion of the supporting structure wound in the helical pattern.

In some embodiments, the method of manufacturing a monolithic thin-film lead assembly further includes treating the monolithic thin-film lead assembly with oxygen plasma. In some embodiments, the method of manufacturing a monolithic thin-film lead assembly further includes sealing ends of the polymer tube in the monolithic thin-film lead assembly.

In various embodiments, a method of manufacturing a monolithic thin-film lead assembly is provided that includes: obtaining an initial structure comprising: (i) a cable comprising: a proximal end, a distal end, a supporting structure that extends from the proximal end to the distal end, and a plurality of conductive traces formed on a portion of the supporting structure; and (ii) an electrode assembly formed on the supporting structure at the distal end of the cable, where the electrode assembly comprises one or more electrodes in electrical connection with one or more conductive traces of the plurality of conductive traces; winding the portion of the supporting structure in a helical pattern on a mandrel; heating the initial structure with the portion of the supporting structure wound in the helical pattern on the mandrel to form a first intermediate structure; removing the mandrel from the intermediate structure; inserting the mandrel into a polymer tube; winding the portion of the supporting structure in the helical pattern on the polymer tube and the mandrel to form a second intermediate structure; inserting the second intermediate structure into a heat shrink tube; heating the second intermediate structure with the heat shrink tube to form the monolithic thin-film lead assembly; and removing the heat shrink tube and the mandrel from the monolithic thin-film lead assembly. The heating embeds the supporting structure wound in the helical pattern into the polymer tube.

In some embodiments, the polymer tube is comprised of silicone, a polymer dispersion, parylene, or a polyurethane. In some embodiments, the polymer tube is comprised of polyurethane.

In various embodiments, a neuromodulation system is provided that includes: a neurostimulator comprising an electronics module; a cable comprising: a first helical portion at a proximal end of the cable, the first helical portion having a pitch from 200 μm to 400 μm, a second helical portion at a distal end of the cable, the second helical portion having a pitch from 200 μm to 400 μm, a third helical portion that extends between the first helical portion and the second helical portion, the middle portion being a third helical portion with a pitch from 600 μm to 1600 μm, a supporting structure that extends from the proximal end to the distal end, and a plurality of conductive traces formed on a portion of the supporting structure; an electrode assembly formed on the supporting structure at the distal end of the cable, where the electrode assembly comprises one or more electrodes in electrical connection with one or more conductive traces of the plurality of conductive traces; and a connector formed on the supporting structure at the proximal end and in electrical connection with the one or more conductive traces of the plurality of conductive traces. The connector electrically connects the one or more conductive traces of the plurality of conductive traces to the electronics module.

In various embodiments, a method of manufacturing a monolithic thin-film lead assembly is provided that includes: obtaining an initial structure comprising: (i) a cable comprising: a proximal end, a distal end, a supporting structure that extends from the proximal end to the distal end, and a plurality of conductive traces formed on a portion of the supporting structure; and (ii) an electrode assembly formed on the supporting structure at the distal end of the cable, where the electrode assembly comprises one or more electrodes in electrical connection with one or more conductive traces of the plurality of conductive traces; winding the portion of the supporting structure in a helical pattern on a mandrel; inserting the mandrel with the portion of the supporting structure into a heat shrink tube to form an intermediate structure; heating the first intermediate structure with the portion of the supporting structure wound in the helical pattern on the mandrel to form a second intermediate structure; removing the mandrel from the second intermediate structure such that the second intermediate structure is left with a lumen; injecting the lumen of the second intermediate structure with a polymer to form a third intermediate structure; heating the third intermediate structure with the heat shrink tube to form the monolithic thin-film lead assembly; and removing the heat shrink tube from the monolithic thin-film lead assembly. The heating embeds the supporting structure wound in the helical pattern into the polymer.

In some embodiments, the heat shrink tube is comprised of a fluoropolymer. In some embodiments, the polymer is comprised of silicone, a polyurethane, a copolymer thereof, or a blend thereof. In some embodiments, the polymer has a Shore durometer measured on a Shore 00 Scale of less than 50. In some embodiments, the plurality of conductive traces and the supporting structure wound in the helical pattern are coplanar with the polymer in the monolithic thin-film lead assembly.

In various embodiments, a method of manufacturing a monolithic thin-film lead assembly is provided including: obtaining an initial structure comprising: (i) a cable comprising: a proximal end, a distal end, a supporting structure that extends from the proximal end to the distal end, and a plurality of conductive traces formed on a portion of the supporting structure; and (ii) an electrode assembly formed on the supporting structure at the distal end of the cable, where the electrode assembly comprises one or more electrodes in electrical connection with one or more conductive traces of the plurality of conductive traces; winding the portion of the supporting structure in a helical pattern on a mandrel; cutting a slit into a polymer tube such that a lumen of the polymer tube is exposed along an entire length of the polymer tube; inserting the mandrel with the portion of the supporting structure into the lumen of the polymer tube through the slit to form a first intermediate structure; removing the mandrel from the first intermediate structure such that the first intermediate structure is left with the lumen; sealing ends of the polymer tube in the first intermediate structure to form a second intermediate structure; and heating the second intermediate structure to form the monolithic thin-film lead assembly. The polymer tube encases the portion of the supporting structure wound in the helical pattern.

In some embodiments, the polymer tube is comprised of silicone, a polymer dispersion, parylene, a polyurethane. In some embodiments, an inner diameter of the polymer tube is greater than an outer diameter of the portion of the supporting structure wound in the helical pattern.

In various embodiments, a method of manufacturing a monolithic thin-film lead assembly is provided that includes: obtaining an initial structure comprising: (i) a cable comprising: a proximal end, a distal end, a supporting structure that extends from the proximal end to the distal end, and a plurality of conductive traces formed on a portion of the supporting structure; and (ii) an electrode assembly formed on the supporting structure at the distal end of the cable, where the electrode assembly comprises one or more electrodes in electrical connection with one or more conductive traces of the plurality of conductive traces; winding the portion of the supporting structure in a helical pattern on a mandrel; removing the mandrel from the portion of the supporting structure; treating the portion of the supporting structure with oxygen plasma; diluting a liquid prepolymer or polymer with a solvent to form a solution; applying the solution on the supporting structure to form an intermediate structure comprising one or more coats of polymer; and heating the intermediate structure to form the monolithic thin-film lead assembly. The polymer encases the portion of the supporting structure wound in the helical pattern.

In some embodiments, the polymer is comprised of silicone, a polymer dispersion, parylene, or a polyurethane. In some embodiments, the applying the solution comprises applying the solution using a dip coating process, a spin coating process, or a spray coating process.

In various embodiments, a lead assembly is provided comprising: a cable comprising: a proximal end, a distal end, a supporting structure that extends from the proximal end to the distal end, and a plurality of conductive traces formed on a portion of the supporting structure, where the supporting structure is comprised of one or more layers of dielectric material; and an interface formed on the supporting structure at the distal end of the cable, where the interface comprises a plurality of electrodes and/or a plurality of sensors in electrical connection with one or more conductive traces of the plurality of conductive traces, the plurality of electrodes comprise a first set of electrodes and a second set of electrodes and/or the plurality of sensors comprise a first set of sensors and a second set of sensors, the supporting structure at the distal end of the cable comprises at least one curved portion; and (i) the at least one curved portion of the supporting structure is disposed between the first set of electrodes and the second set of electrodes, and/or (ii) the at least one curved portion of the supporting structure is disposed between the first set of sensors and the second set of sensors.

In some embodiments, the supporting structure at the distal end of the cable is thermoformed into a curved structure comprising the at least one curved portion.

In some embodiments, the at least one curved portion is a single curved portion and the curved structure has a shape of a "U" or a "J".

In some embodiments, the at least one curved portion is multiple curved portions and the curved structure has a shape of a "S", a helix, or a involute spiral.

In some embodiments, the plurality of conductive traces have a thickness from 0.5 μm to 100 μm.

In some embodiments, the cable has a spiral shape comprising two or more turns and a pitch between each of the turns from 10 μm to 1 cm.

In some embodiments, the plurality of conductive traces extend from the proximal end to the distal end.

In some embodiments, a length of the supporting structure is from 5 cm to 150 cm, and a width of the supporting structure is from 25 μm to 5 mm.

In some embodiments, the dielectric material is polyimide, liquid crystal polymer, parylene, polyether ether ketone, or a combination thereof.

In some embodiments, the plurality of conductive traces are comprised of one or more layers of conductive material, and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof.

In some embodiments, a coefficient of thermal expansion for the plurality of conductive traces is approximately equal to a coefficient of thermal expansion for the supporting structure.

In some embodiments, the lead assembly further comprises a multiplexer chip formed on the supporting structure at the proximal end or the distal end, the multiplexer chip in electrical connection with the plurality of electrodes and/or the plurality of sensors via the plurality of conductive traces.

In various embodiments, a method of manufacturing a monolithic thin-film lead assembly is provided that comprises: forming a cable comprising: forming a first polymer layer; and forming a plurality of conductive traces on a first portion of the first polymer layer, where the forming the plurality of conductive traces comprises depositing a conductive material on the first portion of the first polymer layer; forming an interface comprising: forming a wiring layer on a second portion of the first polymer layer, where the forming the wiring layer comprises depositing the conductive material in electrical contact with the plurality of conductive traces; depositing a second polymer layer on the wiring layer and the second portion of the first polymer layer; forming a plurality of electrodes and/or a plurality of sensors on the second polymer layer such that the plurality of electrodes and/or the plurality of sensors are in electrical contact with at least a portion of a top surface of the wiring layer; where the plurality of electrodes comprise a first set of electrodes and a second set of electrodes and/or the plurality of sensors comprise a first set of sensors and a second set of sensors; forming at least one curved portion in the second portion of the first polymer layer and the second polymer layer, where the at least one curved portion is formed by wrapping the interface around a mandrel or placing the interface in a mold, and where: (i) the at least one curved portion is disposed between the first set of electrodes and the second set of electrodes, and/or (ii) the at least one curved portion is disposed between the first set of sensors and the second set of sensors; and heating the interface while wrapped around the mandrel or placed in the mold to thermoform the second portion of the first polymer layer and the second polymer layer into a curved structure comprising the at least one curved portion.

In some embodiments, the at least one curved portion is a single curved portion and the curved structure has a shape of a "U" or a "J".

In some embodiments, the at least one curved portion is multiple curved portions and the curved structure has a shape of a "S", a helix, or a involute spiral.

In some embodiments, the method further comprises: inserting a guidewire having a stylet though the interface causing the at least one curved portion to straighten, which forces the curved structure into a linear structure.

In various embodiments, a method for deploying a monolithic thin-film lead assembly is provided that comprises: obtaining the lead assembly comprising: a cable comprising: a proximal end, a distal end, a supporting structure that extends from the proximal end to the distal end, and a plurality of conductive traces formed on a portion of the supporting structure, where the supporting structure is comprised of one or more layers of dielectric material; an interface formed on the supporting structure at the distal end of the cable, where the interface comprises a plurality of electrodes and/or a plurality of sensors in electrical connection with one or more conductive traces of the plurality of conductive traces, where the plurality of electrodes comprise a first set of electrodes and a second set of electrodes and/or the plurality of sensors comprise a first set of sensors and a second set of sensors; and a guidewire comprising a stylet inserted through the interface, where while the stylet is inserted through the interface, the interface has a first profile, and where the first profile is straight with the first set of electrodes and the second set of electrodes and/or the first set of sensors and the second set of sensors provided in a linear array; inserting, with the guidewire, the lead assembly into a cavity (such as an endovascular cavity) of a subject; moving, with the guidewire, the lead assembly through the cavity to position the interface at a target location (such as a target location for brain computer interfacing); and removing the guidewire and stylet from the cavity while leaving the lead assembly in place with the interface positioned at the target location, where removal of the stylet from the interface allows for the interface to take a second profile having at least one curved portion, where: (i) the at least one curved portion is disposed between the first set of electrodes and the second set of electrodes, and/or (ii) the at least one curved portion is disposed between the first set of sensors and the second set of sensors.

In some embodiments, the at least one curved portion is a single curved portion and the curved structure has a shape of a "U" or a "J".

In some embodiments, the at least one curved portion is multiple curved portions and the curved structure has a shape of a "S", a helix, or a involute spiral.

In some embodiments, the method further comprises: connecting the cable to a computing device and using the computing device to send a single through the interface to tissue at the target location or receive a signal from the tissue at the target location.

BRIEF DESCRIPTION OF THE DRAWINGS

The present invention will be better understood in view of the following non-limiting figures, in which:

FIG. 1 shows a neuromodulation system in accordance with various embodiments;

FIGS. 12A-12G show lead assembly views illustrating a method of forming a lead assembly in accordance with various embodiments;

DETAILED DESCRIPTION

I. Introduction

Figure 2A:
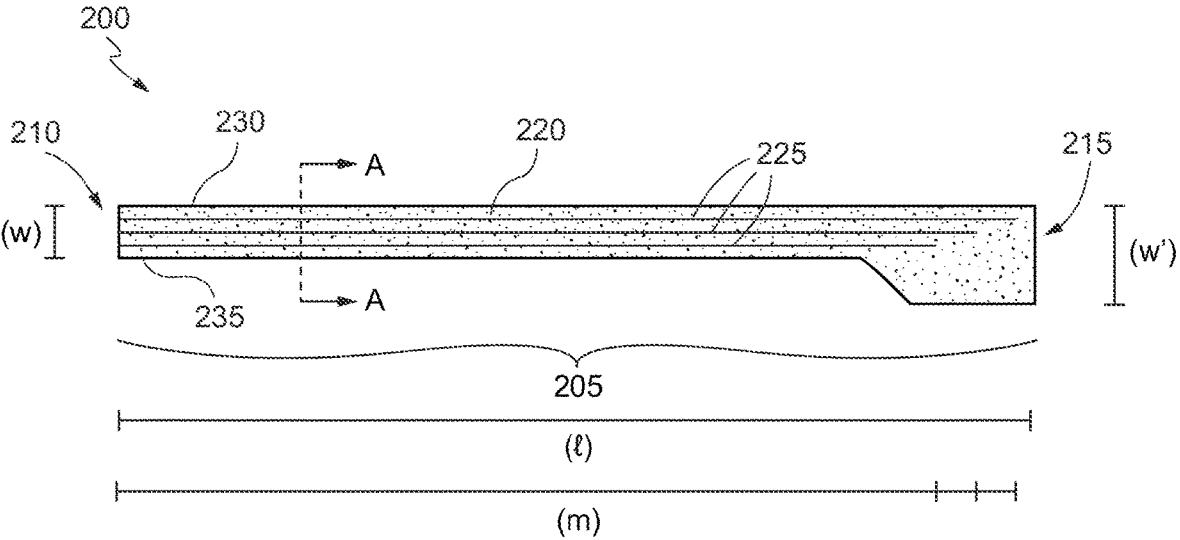
FIGS. 2A-2H show a lead assembly in accordance with various embodiments.

The following disclosure describes monolithic thin-film lead assemblies and methods of microfabricating monolithic thin-film lead assemblies. As used herein, the phrase "monolithic" refers to a device fabricated using a same layer of base material. The device may be fabricated using microfabricating techniques. As used herein, the phrase "microfabrication" refers to the process of fabricating miniature structures on micrometer scales and smaller. The major concepts and principles of microfabrication are microlithography, doping, thin films, etching, bonding, and polishing. As used herein, the phrase "thin films" refers to a layer of material ranging from fractions of a nanometer (monolayer) to several micrometers in thickness (e.g., between a few nanometers to about 100 μm, or the thickness of a few atoms). Thin films may be deposited by applying a very thin film of material (e.g., between a few nanometers to about 100 μm, or the thickness of a few atoms) onto a substrate surface to be coated, or onto a previously deposited layer of thin film. In various embodiments, a thin film lead assembly is provided comprising a base polymer body (e.g., a supporting structure) and at least one conductive trace formed on the base polymer body.

Limitations associated with conventional thin film cables such as flexible printed circuits, flexible foil circuits or flexible flat cables is that the cable length is restricted by a size of the wafer or panel used to fabricate the cable, the base polymer typically has a small elastic elongation (e.g., an elastic elongation of <20%), and the cables are overall stiff with a relatively high Young's modulus (e.g., >1.0 GPa). All of these limitations create challenges for using thin film cables in electrical neuromodulation systems where the cables need to extend deep within the patient while allowing for freedom of movement by the patient with very little to no irritation or damage to surrounding tissues. Moreover, as discussed herein, conventional cables used in electrical neuromodulation systems have connectors on both ends for connecting the cable to additional components such as a lead conductor, electrode, and neurostimulator. The use of connectors and the presence of multiple conductive components to supply electrical signals between the neurostimulator and the electrodes results in an overall bulky electrical neuromodulation system and provide multiple connection points that are susceptible to disconnections and fractures of system components.

To address these limitations and problems, the thin film cable of various embodiments disclosed herein is a monolithic structure, which results in less connection points, a smaller footprint, and greater design flexibility. One illustrative embodiment of the present disclosure is directed to a monolithic thin-film lead assembly that comprises a cable having a proximal end, a distal end, a supporting structure that extends from the proximal end to the distal end, and a plurality of conductive traces formed on a portion of the supporting structure. The supporting structure may include one or more layers of dielectric material. The monolithic thin-film lead assembly may further include an electrode assembly formed on the supporting structure at the distal end of the cable. The electrode assembly may include one or more electrodes in electrical connection with one or more conductive traces of the plurality of conductive traces.

In other embodiments, a monolithic thin-film lead assembly is provided directed to a specific application (e.g., a deep brain neurostimulation). The monolithic thin-film lead assembly comprises a cable having: a first helical portion at a proximal end of the cable, the first helical portion having a pitch from 200 μm to 400 μm, a second helical portion at a distal end of the cable, the second helical portion having a pitch from 200 μm to 400 μm, a third helical portion that extends between the first helical portion and the second helical portion, the middle portion being a third helical portion with a pitch from 600 μm to 1600 μm, a supporting structure that extends from the proximal end to the distal end, and a plurality of conductive traces formed on a portion of the supporting structure. The monolithic thin-film lead assembly may further include an electrode assembly formed on the supporting structure at the distal end of the cable. The electrode assembly may comprise one or more electrodes in electrical connection with one or more conductive traces of the plurality of conductive traces.

In other embodiments, a monolithic thin-film lead assembly is provided directed to a specific application (e.g., vagus nerve or artery/nerve plexus). The monolithic thin-film lead assembly comprises a cable having: a helical portion that extends between a proximal end and a distal end of the cable, the helical portion having a pitch from 600 μm to 1600 μm, a supporting structure that extends from the proximal end to the distal end of the cable, and a plurality of conductive traces formed on a portion of the supporting structure. The monolithic thin-film lead assembly may further include an electrode assembly formed on the supporting structure at the distal end of the cable. The electrode assembly may comprise one or more electrodes in electrical connection with one or more conductive traces of the plurality of conductive traces.

In other embodiments, a monolithic thin-film lead assembly is provided comprising: a cable comprising: a proximal end, a distal end, a supporting structure that extends from the proximal end to the distal end, and a plurality of conductive traces formed on a portion of the supporting structure, where the supporting structure is comprised of one or more layers of dielectric material; and an interface formed on the supporting structure at the distal end of the cable, where the interface comprises a plurality of electrodes and/or a plurality of sensors in electrical connection with one or more conductive traces of the plurality of conductive traces. The plurality of electrodes comprise a first set of electrodes and a second set of electrodes and/or the plurality of sensors comprise a first set of sensors and a second set of sensors. The supporting structure at the distal end of the cable comprises at least one curved portion. The at least one curved portion of the supporting structure is disposed between the first set of electrodes and the second set of electrodes, and/or the at least one curved portion of the supporting structure is disposed between the first set of sensors and the second set of sensors.

To further address these limitations and problems, a method of manufacturing the thin film cable of various embodiments disclosed herein includes process steps for creating a monolithic structure, which results in less connection points, a smaller footprint, and greater design flexibility. One illustrative embodiment of the present disclosure is directed to method of manufacturing a monolithic thin-film lead assembly that comprises forming a first polymer layer on a wafer or panel of substrate, and forming a plurality of conductive traces on a first portion of the first polymer layer. The forming the plurality of conductive traces may comprise depositing a conductive material in a spiral pattern with two or more turns on the first portion of the first polymer layer. The method further comprises forming a wiring layer on a second portion of the first polymer layer. The forming the wiring layer may comprise depositing the conductive material in electrical contact with the plurality of conductive traces. The method may further comprise depositing a second polymer layer on the wiring layer and the second portion of the first polymer layer, forming at least one electrode on the second polymer layer such that the at least one electrode is in electrical contact with at least a portion of a top surface of the wiring layer, and cutting the monolithic thin-film lead assembly from the first polymer layer. The monolithic thin-film lead assembly may comprise the plurality of conductive traces in the spiral pattern on the first polymer layer and the at least one electrode on the second polymer layer electrically connected to the plurality of conductive traces.

In other embodiments, a method of manufacturing a monolithic thin-film lead assembly is provided that comprises obtaining an initial structure comprising: (i) a cable comprising: a proximal end, a distal end, a supporting structure that extends from the proximal end to the distal end, and a plurality of conductive traces formed on a portion of the supporting structure; and (ii) an electrode assembly formed on the supporting structure at the distal end of the cable. The electrode assembly may comprise one or more electrodes in electrical connection with one or more conductive traces of the plurality of conductive traces. The method further comprises winding the portion of the supporting structure in a helical pattern on a mandrel, inserting the mandrel with the portion of the supporting structure into a polymer tube to form an intermediate structure, heating the intermediate structure with the portion of the supporting structure wound in the helical pattern on the mandrel to form the monolithic thin-film lead assembly, and removing the mandrel from the monolithic thin-film lead assembly. The polymer tube may completely encase the portion of the supporting structure wound in the helical pattern.

In other embodiments, a method of manufacturing a monolithic thin-film lead assembly is provided that comprises obtaining an initial structure comprising: (i) a cable comprising: a proximal end, a distal end, a supporting structure that extends from the proximal end to the distal end, and a plurality of conductive traces formed on a portion of the supporting structure; and (ii) an electrode assembly formed on the supporting structure at the distal end of the cable. The electrode assembly may comprise one or more electrodes in electrical connection with one or more conductive traces of the plurality of conductive traces. The method further comprises winding the portion of the supporting structure in a helical pattern on a mandrel, heating the initial structure with the portion of the supporting structure wound in the helical pattern on the mandrel to form a first intermediate structure, removing the mandrel from the intermediate structure, inserting the mandrel into a polymer tube, winding the portion of the supporting structure in the helical pattern on the polymer tube and the mandrel to form a second intermediate structure, inserting the second intermediate structure into a heat shrink tube, heating the second intermediate structure with the heat shrink tube to form the monolithic thin-film lead assembly, and removing the heat shrink tube and the mandrel from the monolithic thin-film lead assembly. The heating may embed the supporting structure wound in the helical pattern into the polymer tube.

In other embodiments, a method of manufacturing a monolithic thin-film lead assembly is provided that comprises forming a cable comprising: forming a first polymer layer; and forming a plurality of conductive traces on a first portion of the first polymer layer, where the forming the plurality of conductive traces comprises depositing a conductive material on the first portion of the first polymer layer; forming an interface comprising: forming a wiring layer on a second portion of the first polymer layer, where the forming the wiring layer comprises depositing the conductive material in electrical contact with the plurality of conductive traces; depositing a second polymer layer on the wiring layer and the second portion of the first polymer layer; forming a plurality of electrodes and/or a plurality of sensors on the second polymer layer such that the plurality of electrodes and/or the plurality of sensors are in electrical contact with at least a portion of a top surface of the wiring layer; where the plurality of electrodes comprise a first set of electrodes and a second set of electrodes and/or the plurality of sensors comprise a first set of sensors and a second set of sensors; forming at least one curved portion in the second portion of the first polymer layer and the second polymer layer, where the at least one curved portion is formed by wrapping the interface around a mandrel or placing the interface in a mold, and where: (i) the at least one curved portion is disposed between the first set of electrodes and the second set of electrodes, and/or (ii) the at least one curved portion is disposed between the first set of sensors and the second set of sensors; and heating the interface while wrapped around the mandrel or placed in the mold to thermoform the second portion of the first polymer layer and the second polymer layer into a curved structure comprising the at least one curved portion.

In other embodiments, a method for deploying a monolithic thin-film lead assembly is provided that comprises: obtaining the lead assembly comprising: a cable comprising: a proximal end, a distal end, a supporting structure that extends from the proximal end to the distal end, and a plurality of conductive traces formed on a portion of the supporting structure, where the supporting structure is comprised of one or more layers of dielectric material; an interface formed on the supporting structure at the distal end of the cable, where the interface comprises a plurality of electrodes and/or a plurality of sensors in electrical connection with one or more conductive traces of the plurality of conductive traces, where the plurality of electrodes comprise a first set of electrodes and a second set of electrodes and/or the plurality of sensors comprise a first set of sensors and a second set of sensors; and a guidewire comprising a stylet inserted through the interface, where while the stylet is inserted through the interface, the interface has a first profile, and where the first profile is straight with the first set of electrodes and the second set of electrodes and/or the first set of sensors and the second set of sensors provided in a linear array; inserting, with the guidewire, the lead assembly into a cavity (such as an endovascular cavity) of a subject; moving, with the guidewire, the lead assembly through the cavity to position the interface at a target location (such as a target location for brain computer interfacing); and removing the guidewire and stylet from the cavity while leaving the lead assembly in place with the interface positioned at the target location, where removal of the stylet from the interface allows for the interface to take a second profile having at least one curved portion, where: (i) the at least one curved portion is disposed between the first set of electrodes and the second set of electrodes, and/or (ii) the at least one curved portion is disposed between the first set of sensors and the second set of sensors. In some instances, the cable is connected to a computing device and the computing device is used to send a single through the interface to tissue at the target location or receive a signal from the tissue at the target location.

Advantageously, these approaches provide a monolithic thin-film lead assembly, which has less connection points, a smaller footprint, and greater design flexibility. More specifically, these approaches enable continuous electrode(s) and conductor(s) on a single cable or lead body. This solution is scalable to connecting several electrodes using a multi flex chip, and thus enabling several therapeutic opportunities for neurostimulation. Furthermore even for applications where multiple electrodes are not required, various embodiments can be miniaturized to make the implant minimally invasive, additionally may make invasive anatomies to become accessible (or navigable) due to the miniaturization. It should be understood that although deep brain neurostimulation and vagus nerve or artery/nerve plexus device applications are provided as examples of some embodiments, this solution is applicable to all leads and devices that need electrodes/sensors that need to be attached to long lengths of conductors.

II. Neuromodulation Devices and Systems with a Lead Assembly

Figure 1:
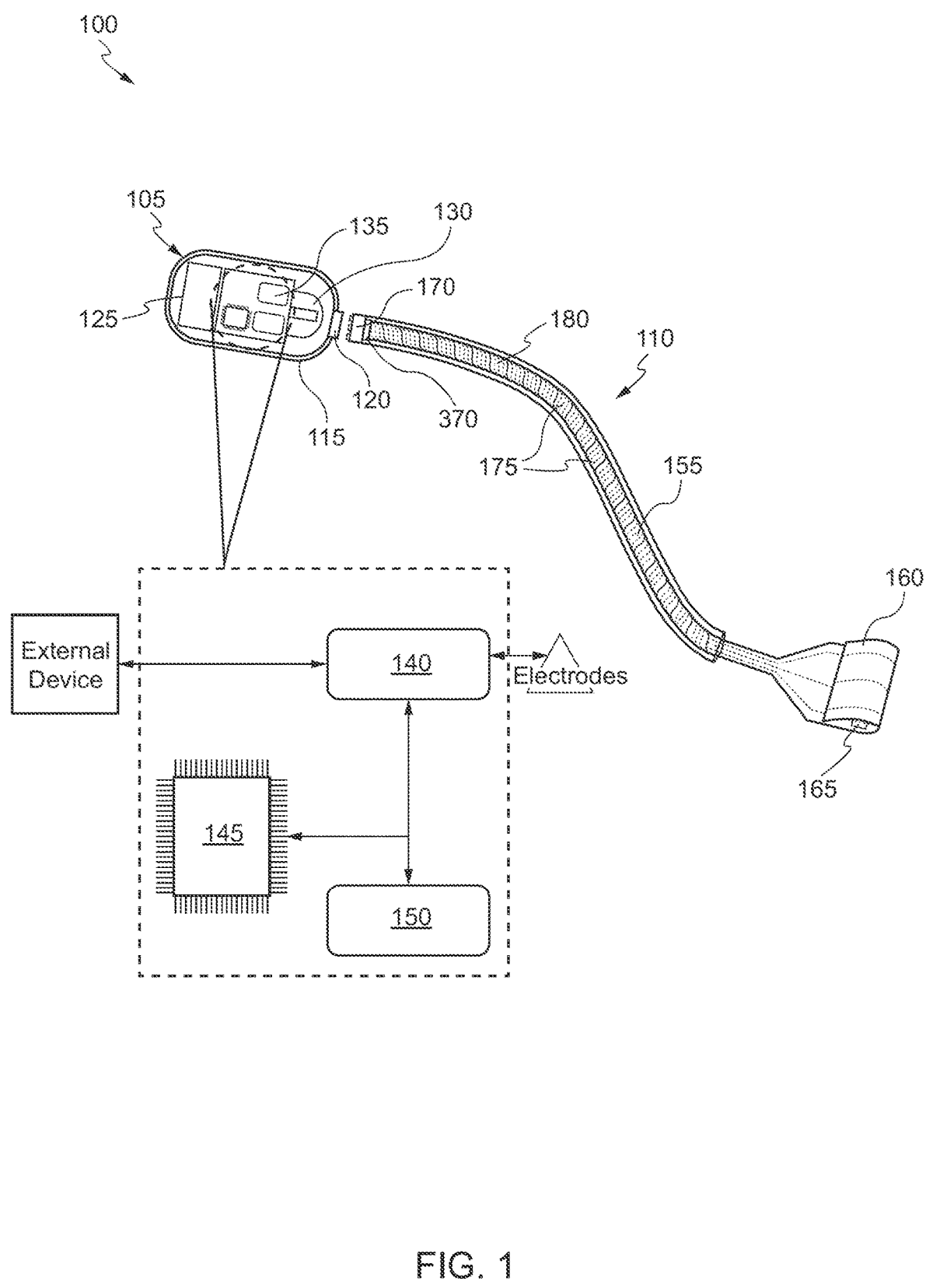

FIG. 1 shows a neuromodulation system 100 in accordance with some aspects of the present invention. In various embodiments, the neuromodulation system 100 includes an implantable neurostimulator 105 and a lead assembly 110. The implantable neurostimulator 105 may include a housing 115, a feedthrough assembly 120, a power source 125, an antenna 130, and an electronics module 135 (e.g., a computing system). The housing 115 may be comprised of materials that are biocompatible such as bioceramics or bioglasses for radio frequency transparency, or metals such as titanium. In accordance with some aspects of the present invention, the size and shape of the housing 115 may be selected such that the neurostimulator 105 can be implanted within a patient. In the example shown in FIG. 1, the feedthrough assembly 120 is attached to a hole in a surface of the housing 115 such that the housing 115 is hermetically sealed. The feedthrough assembly 120 may include one or more feedthroughs (i.e., electrically conductive elements, pins, wires, tabs, pads, etc.) mounted within and extending through the surface of the housing 115 or a cap from an interior to an exterior of the housing 115. The power source 125 may be within the housing 115 and connected (e.g., electrically connected) to the electronics module 135 to power and operate the components of the electronics module 135. The antenna 130 may be connected (e.g., electrically connected) to the electronics module 135 for wireless communication with external devices via, for example, radiofrequency (RF) telemetry.

In some embodiments, the electronics module 135 may be connected (e.g., electrically connected) to interior ends of the feedthrough assembly 120 such that the electronics module 135 is able to apply a signal or electrical current to conductive traces of the lead assembly 110 connected to exterior ends of the feedthrough assembly 120. The electronics module 135 may include discrete and/or integrated electronic circuit components that implement analog and/or digital circuits capable of producing the functions attributed to the neuromodulation devices or systems such as applying or delivering neural stimulation to a patient. In various embodiments, the electronics module 135 may include software and/or electronic circuit components such as a pulse generator 140 that generates a signal to deliver a voltage, current, optical, or ultrasonic stimulation to a nerve or artery/nerve plexus via electrodes, a controller 145 that determines or senses electrical activity and physiological responses via the electrodes and sensors, controls stimulation parameters of the pulse generator 140 (e.g., control stimulation parameters based on feedback from the physiological responses), and/or causes delivery of the stimulation via the pulse generator 140 and electrodes, and a memory 150 with program instructions operable on by the pulse generator 140 and the controller 145 to perform one or more processes for applying or delivering neural stimulation.

In various embodiments, the lead assembly 110 is a monolithic structure that includes a cable or lead body 155.

In some embodiments, the lead assembly 110 further includes one or more electrode assemblies 160 having one or more electrodes 165, and optionally one or more sensors. In some embodiments, the lead assembly 110 further includes a connector 170. In certain embodiments, the connector 170 is bonding material that bonds conductor material of the cable 155 to the electronics module 135 of the implantable neurostimulator 105 via the feedthrough assembly 120. The bonding material may be a conductive epoxy or a metallic solder or weld such as platinum. In other embodiments, the connector 170 is conductive wire, conductive traces, or bond pads (e.g., a wire, trace, or bond pads formed of a conductive material such as copper, silver, or gold) formed on a substrate and bonds a conductor of the cable 155 to the electronics module 135 of the implantable neurostimulator 105. In alternative embodiments, the implantable neurostimulator 105 and the cable 155 are designed to connect with one another via a mechanical connector 170 such as a pin and sleeve connector, snap and lock connector, flexible printed circuit connectors, or other means known to those of ordinary skill in the art.

The cable 155 may include one or more conductive traces 175 formed on a supporting structure 180. The one or more conductive traces 175 allow for electrical coupling of the electronics module 135 to the electrodes 165 and/or sensors of the electrode assemblies 160. As described herein in detail, the supporting structure 180 may be formed with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends may be used. The conductive material for the traces 175 may be any suitable conductor such as stainless steel, silver, copper or other conductive materials, which may have separate coatings or sheathing for anticorrosive, insulative and/or protective reasons.

The electrode assemblies 160 may include the electrodes 165 and/or sensors fabricated using various shapes and patterns to create certain types of electrode assemblies (e.g., book electrodes, split cuff electrodes, spiral cuff electrodes, epidural electrodes, helical electrodes, probe electrodes, linear electrodes, neural probe, paddle electrodes, intraneural electrodes, etc.). In various embodiments, the electrode assemblies 160 include a base material that provides support for microelectronic structures including the electrodes 165, a wiring layer, optional contacts, etc. In some embodiments, the base material is the supporting structure 180. The wiring layer may be embedded within or located on a surface of the supporting structure 180. The wiring layer may be used to electrically connect the electrodes 165 with the one or more conductive traces 175 directly or indirectly via a lead conductor. The term "directly", as used herein, may be defined as being without something in between. The term "indirectly", as used herein, may be defined as having something in between. In some embodiments, the electrodes 165 may make electrical contact with the wiring layer by using the contacts.

III. Lead Assemblies

FIG. 2A shows a lead assembly 200 (e.g., the monolithic lead assembly 110 described with respect to FIG. 1) in accordance with aspects of the present disclosure. In various embodiments, the lead assembly 200 comprises a cable 205 having a proximal end 210 and a distal end 215. As used herein, the term "proximal end" refers to a first end of the main body, while the term "distal end" refers to a second end opposing the first end. For example, the proximal end may be an end of the main body, which is closest to the user, and the distal end may be an end of the main body, which is furthest from the user. The cable 205 may comprise a supporting structure 220 and one or more conductive traces 225 formed on a portion of the supporting structure. As used herein, the term "formed on" refers to a structure or feature that is formed on a surface of another structure or feature, a structure or feature that is formed within another structure or feature, or a structure or feature that is formed both on and within another structure or feature. In some embodiments, the supporting structure 220 extends from the proximal end 210 to the distal end 215. In some embodiments, the supporting structure 220 may be made of one or more layers of dielectric material (i.e., an insulator). The dielectric material may be selected from the group of electrically nonconductive materials consisting of organic or inorganic polymers, ceramics, glass, glass-ceramics, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In other embodiments, the supporting structure 220 may be made of one or more layers of dielectric material formed on a substrate. The substrate may be made from any type of metallic or non-metallic material.

Figure 2B:
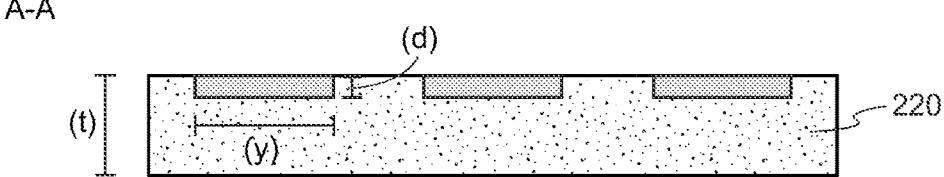

As shown in FIG. 2B, in various embodiments, the supporting structure 220 comprising the one or more layers of dielectric material, and optionally the substrate, has a thickness (t) from the proximal end 210 to the distal end 215. In some embodiments, the thickness (t) is from 10 μm to 150 μm, for example about 50 μm or about 60 μm. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. In some embodiments, the supporting structure 220 has a length (l) of 5 cm to 150 cm or 50 cm to 100 cm, e.g., about 75 cm (see, e.g., FIG. 2A). In some embodiments, the supporting structure 220 has a width (w) from a first side 230 to a second side 235. In some embodiments, the width (w) is from 25 μm to 5 mm, for example about 400 μm or about 1000 μm (see, e.g., FIG. 2A).

In various embodiments, the one or more conductive traces 225 are a plurality of traces, for example, two or more conductive traces or from two to twenty-four conductive traces. The plurality of conductive traces 225 are comprised of one or more layers of conductive material. The conductive material selected for the one or more conductive traces 225 should have good electrical conductivity and may include pure metals, metal alloys, combinations of metals and dielectrics, and the like. For example, the conductive material may be copper (Cu), gold (Au), silver (Ag), gold/chromium (Au/Cr), etc. In some embodiments, it is also desirable that the conductive material selected for the one or more conductive traces 225 have thermal expansion characteristics or a coefficient of thermal expansion (CTE) that is approximately equal to that of CTE of the supporting structure 220. Matching the CTE of components that contact one another is desirable because it eliminates the development of thermal stresses, which may occur during fabrication and the operation of the cable, and thus eliminates a known cause of mechanical failure in the components.

The one or more conductive traces 225 may be deposited onto a surface of the supporting structure 220 by using thin film deposition techniques well known to those skilled in the art such as by sputter deposition, chemical vapor deposition, metal organic chemical vapor deposition, electroplating, electroless plating, and the like. In some embodiments, the thickness of the one or more conductive traces 225 is dependent on the particular impedance desired for conductor, in order to ensure excellent signal integrity (e.g., electrical signal integrity for stimulation or recording). For example, if a conductor having a relatively high impedance is desired, a small thickness of conductive material should be deposited onto the supporting structure 220. If, however, a signal plane having a relatively low impedance is desired, a greater thickness of electrically conductive material should be deposited onto the supporting structure 220. In certain embodiments, each of the one or more conductive traces 225 has a thickness (d). In some embodiments, the thickness (d) is from 0.5 μm to 100 μm or from 25 μm to 50 μm, for example about 25 μm or about 40 μm. In some embodiments, each of the one or more conductive traces 225 has a length (m) of about 5 cm to 200 cm or 50 cm to 150 cm, e.g., about 80 cm. In certain embodiments, each of the one or more conductive traces 225 extends from the proximal end 210 to the distal end 215. In some embodiments, each of the one or more conductive traces 225 has a width (y) from 2.0 μm to 500 μm, for example about 30 μm or about 50 μm.

Figure 2C:
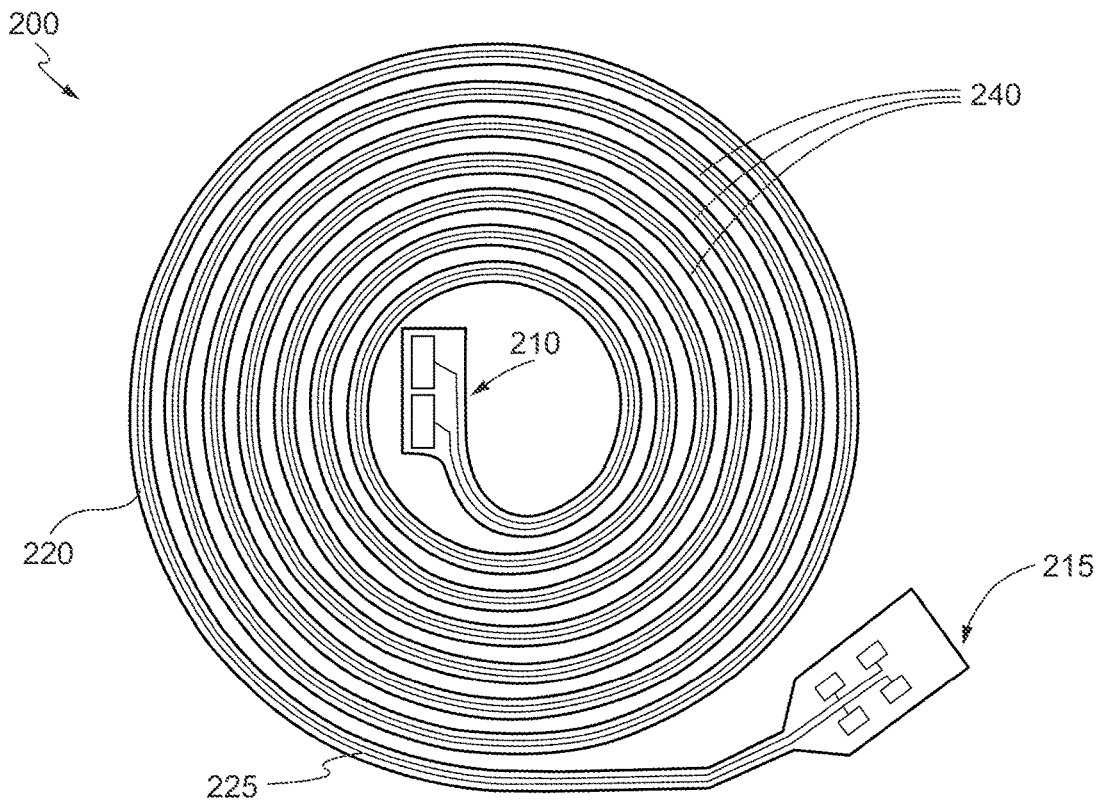
Figure 2C:
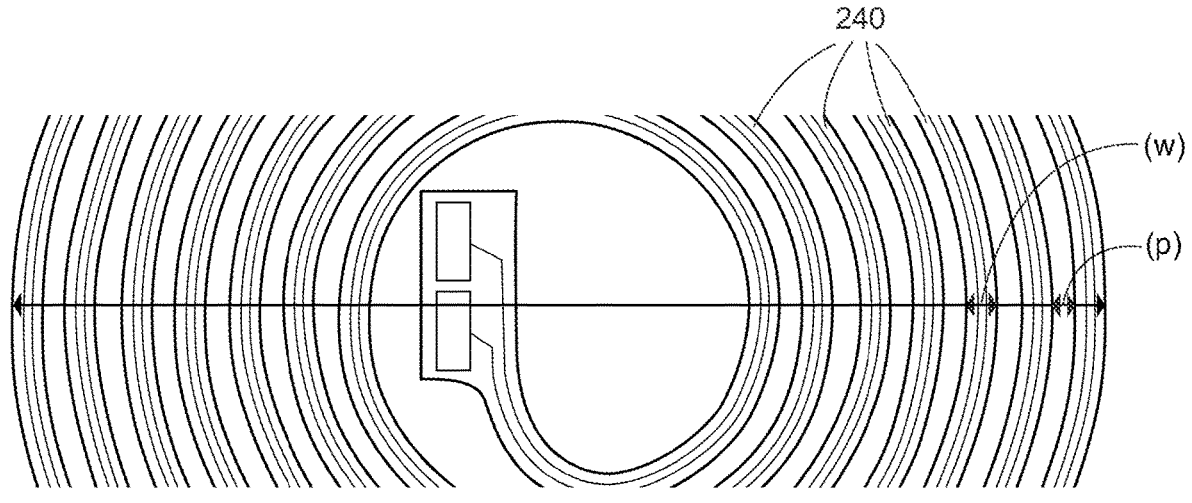

As shown in FIG. 2C, the lead assembly 200 may be formed with a predetermined shape in accordance with aspects of the present disclosure. In particular, as described in greater detail herein, the lead assembly 200 may be formed with a predetermined shape from a prefabricated wafer or panel of dielectric material or optionally a substrate. For example, the lead assembly 200 may be laser cut from a prefabricated wafer or panel in a spiral shape. The spiral shape may include characteristics designed to maximize the length of the lead assembly 200 that can be fabricated from a single wafer or panel. Conventionally, wafers or panels have a diameter, length, and/or width of less than 10 cm. In some embodiments, the characteristics of the spiral shape include a predetermined number of turns 240 and a predetermined pitch (p) between each of the turns 240 to maximize the overall length obtainable for the lead assembly 200. In certain embodiments, the spiral shape has 2 or more turns, for example from 2 to 25 turns, and a pitch (p) between each of the turns from 10 μm to 1 cm or from 250 μm to 2 mm, for example about 350 μm. Accordingly, the spiral shape can maximize the length of the lead assembly 200 that can be fabricated from a single wafer or panel. For example, a single wafer or panel with a limited diameter, length, and/or width of less than 10 cm, can be used to fabricate a lead assembly 200 with a length of 5 cm to 150 cm, 10 cm to 100 cm, or 25 cm to 75 cm, e.g., about 15 cm, using the spiral shape.

Figure 2D:
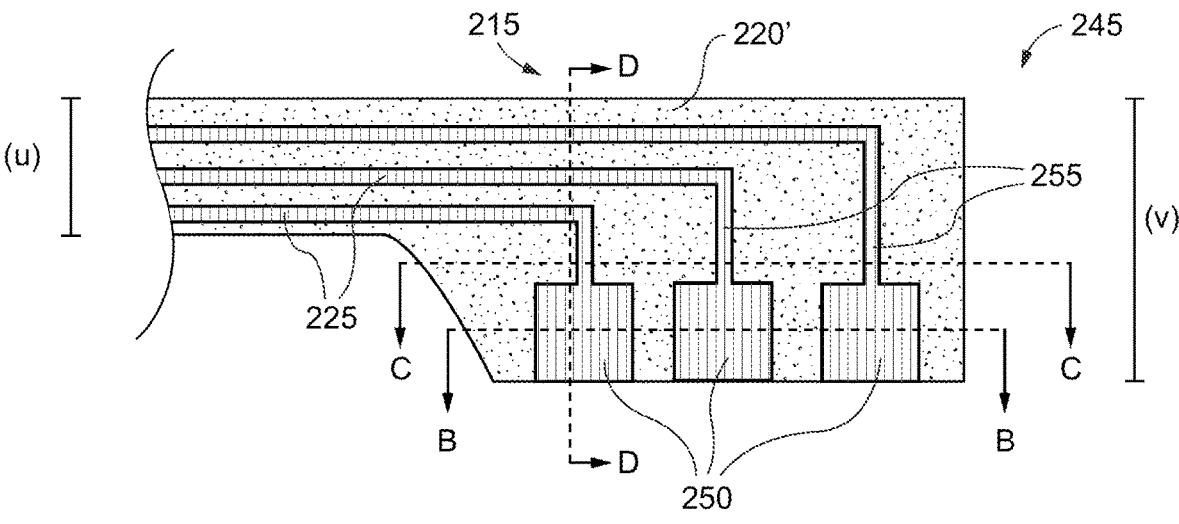
Figure 2E:
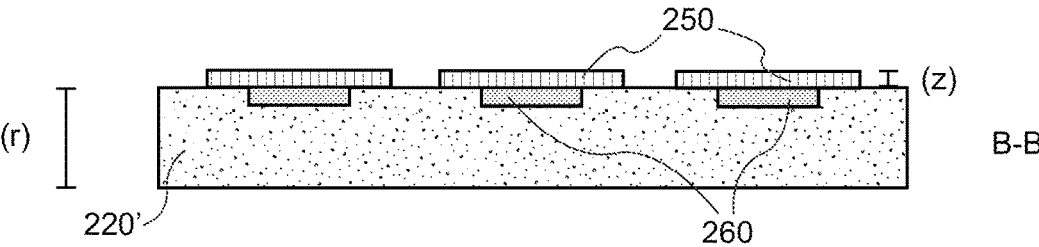
Figure 2F:
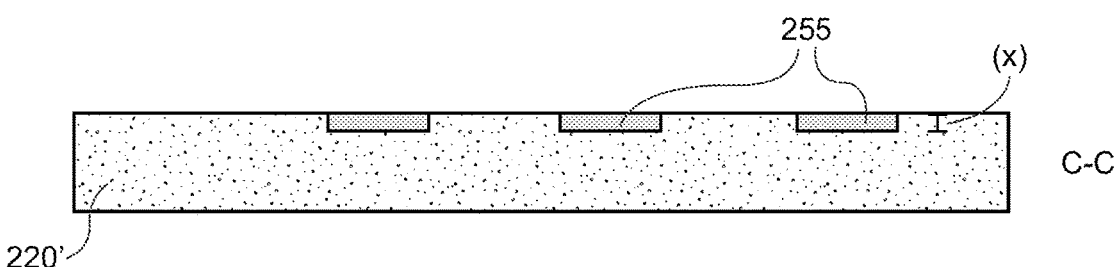
Figure 2G:
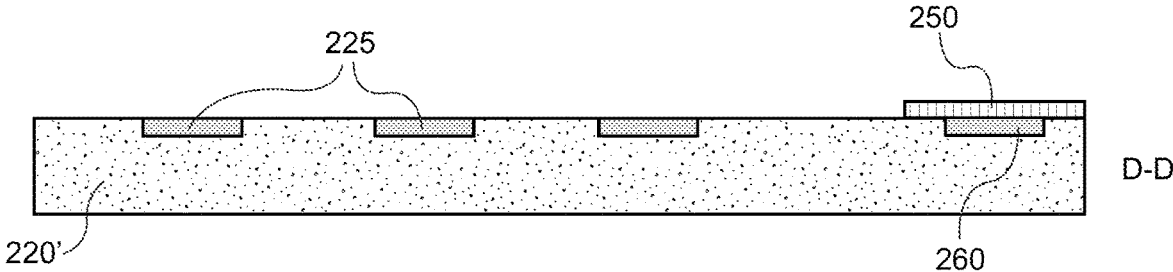

As shown in FIG. 2D, the lead assembly 200 may further comprise an electrode assembly 245 comprising a supporting structure 220' that provides support for microelectronic structures including one or more electrodes 250, a wiring layer 255, and optional contact(s) 260 (shown in FIG. 2F). The electrode assembly 250 may be located at the distal end 215 of the lead assembly 200. In various embodiments, the supporting structure 220' of the lead assembly and the supporting structure 220 of the electrode assembly are the same structure (i.e., the supporting structure is continuous from the proximal end 210 to the distal end 215), which thus creates a monolithic cable. In some embodiments and as shown in FIG. 2E, the supporting structure 220' for the electrode assembly 245 comprising the one or more layers of dielectric material, and optionally the substrate, has a thickness (r) of from 10 μm to 150 μm, from 15 μm to 70 μm, from 30 μm to 60 μm, or from 40 μm to 60 μm. In some embodiments, the supporting structure 220 has a width (v) from a first side 225 to a second side 230. In some embodiments, the width (v) is from 25 μm to 10 mm, for example about 50 μm or about 5000 μm.

The wiring layer 255 may be formed on the supporting structure 220'. In various embodiments, the wiring layer 255 is formed continuously of the one or more conductive traces 225, and is comprised of various metals or alloys thereof, for example, copper (Cu), gold (Au), silver (Ag), gold/chromium (Au/Cr), platinum (Pt), platinum/iridium (Pt/Ir), titanium (Ti), gold/titanium (Au/Ti), or any alloy thereof. The wiring layer 255 may have a thickness (x) of from 0.5 μm to 100 μm, from 0.5 μm to 15 μm, from 0.5 μm to 10 μm, or from 0.5 μm to 5 μm (see, e.g., FIG. 2F). In some embodiments, a top surface of the wiring layer 255 is coplanar with a top surface of the supporting structure 220' (see, e.g., FIG. 2F). In other embodiments, the wiring layer 255 is embedded within the supporting structure 220'. In yet other embodiments, the wiring layer 255 is formed on the top surface of the supporting structure 220' and the top surface of the wiring layer 255 is raised above the top surface of the supporting structure 220'.

In some embodiments, the one or more electrodes 250 are formed on the supporting structure 220' and in electrical contact with the wiring layer 255. The one or more electrodes 250 may be comprised of conductive material such as copper (Cu), gold (Au), silver (Ag), gold/chromium (Au/Cr), platinum (Pt), platinum/iridium (Pt/Ir), titanium (Ti), gold/titanium (Au/Ti), or any alloy thereof, for example. The one or more electrodes 250 may have a thickness (z) of from 0.1 μm to 50 μm, from 0.3 μm to 30 μm, from 0.5 μm to 20 μm, or from 1 μm to 15 μm (see, e.g., FIG. 2E). The one or more electrodes 250 may be formed directly on the supporting structure 220' (see, e.g., FIG. 2E). Alternatively, the one or more electrodes 250 may be formed indirectly on the supporting structure 220'. In some embodiments, the contact (s) 260 are formed on the supporting structure 220' and provide electrical contact between the one or more electrodes 255 and the wiring layer 260 (see, e.g., FIG. 2E). The contact(s) 260 may be comprised of conductive material such as copper (Cu), gold (Au), silver (Ag), gold/chromium (Au/Cr), platinum (Pt), platinum/iridium (Pt/Ir), titanium (Ti), gold/titanium (Au/Ti), or any alloy thereof, for example.

Figure 2H:
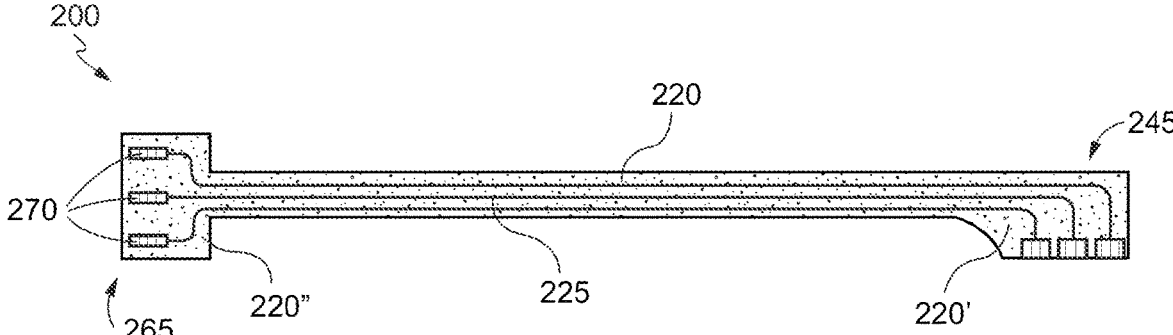

In various embodiments, the lead assembly 200 may further comprise one or more additional supporting structures that may support one or more additional electronic structures of the assembly such as an electrode, conductor, and/or connector. In some embodiments, as shown in FIG. 2H, the lead assembly 200 further comprises supporting structure 225" for a connector 265. In certain embodiments, the connector 265 is bonding material that bonds the one or more conductive traces 225 of the cable 205 to an electronics module of the implantable neurostimulator. The bonding material may be a conductive epoxy or a metallic solder or weld such as platinum. In other embodiments, the connector 265 is conductive wire, conductive traces, or one or more bond or contact pads 270 formed on the supporting substrate 225" and bonds the one or more conductive traces 225 of the cable 205 to the electronics module of the implantable neurostimulator. In alternative embodiments, the implantable neurostimulator and the cable 205 are designed to connect with one another via a mechanical connector 265 such as a pin and sleeve connector, snap and lock connector, flexible printed circuit connectors, or other means known to those of ordinary skill in the art.

The properties of the supporting structures and electronic structures (e.g., thickness, material, position, contact, etc.) may be the same or different from those of the structures previously discussed herein with reference to FIGS. 2A-2G. However, it should be understood the lead assembly 200 is an exemplary embodiment, and that the lead assembly 200 is to be construed with the broadest sense to include variations of the specific design and/or performance need described herein, as well as other variations that are well known to those of skill in the art. In particular, the shape and location of components and layers in the lead assembly 200 may be adjusted or modified to meet specific design and/or performance needs. Furthermore, it is to be understood that other structures may have been omitted from the description of the lead assembly 200 for clarity. The omitted structures may include, for example, sensor structures, insulating layers, interconnect components, passive devices, etc.

Figure 3A:
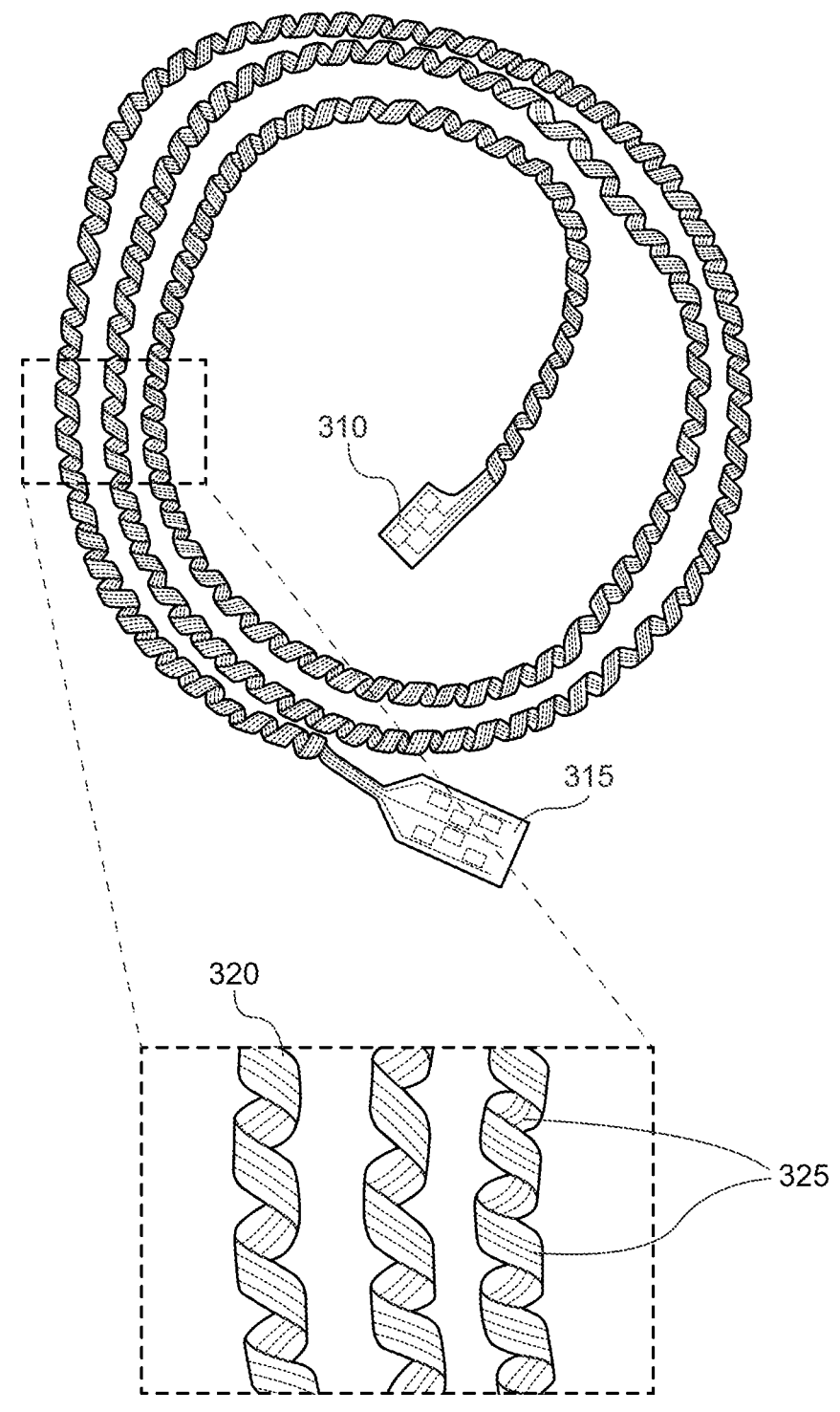
FIGS. 3A and 3B show an alternative lead assembly in accordance with various embodiments.
Figure 3B:
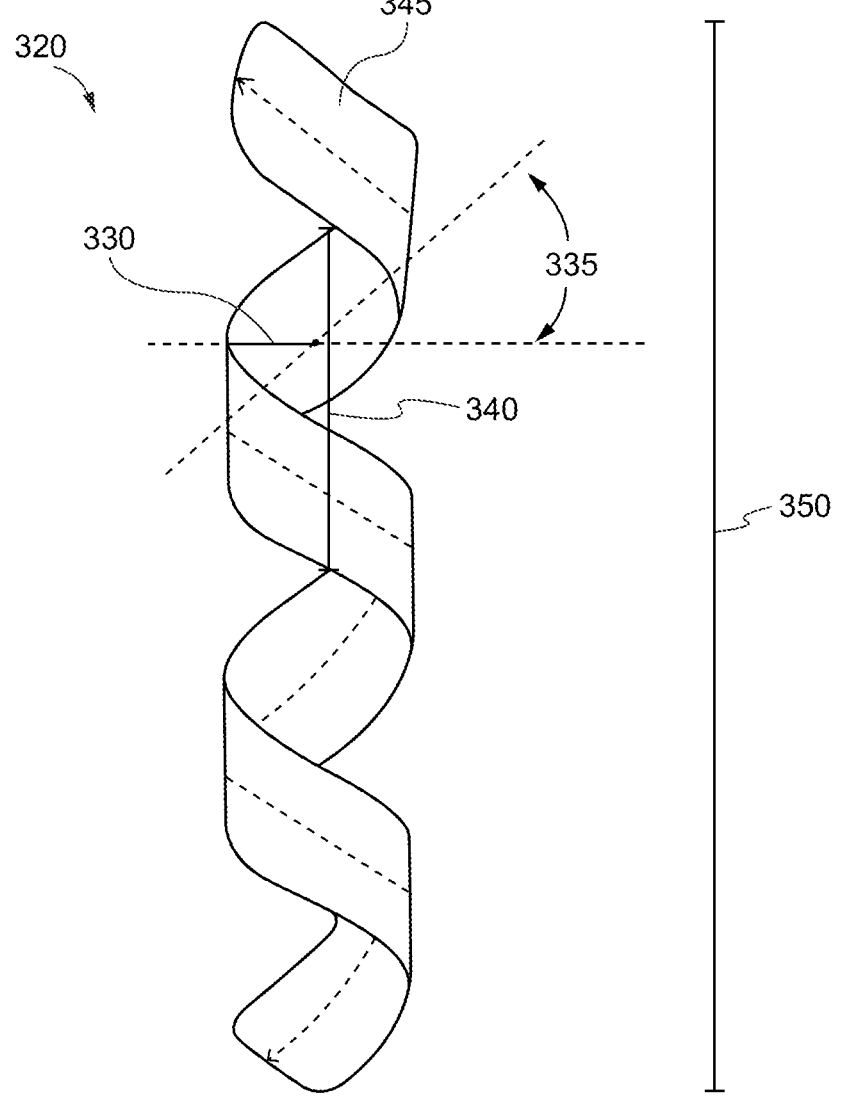

FIGS. 3A and 3B show a lead assembly 300 in accordance with aspects of the present disclosure. In various embodiments, the lead assembly 300 comprises a cable 305 having a proximal end 310 and a distal end 315 (e.g., lead assembly 200 as described with respect to FIGS. 2A-2H). In some embodiments, at least a portion 320 of the cable 305 is helical. As used herein, the phrases "helical" refer to a device fabricated with plural helixes or helices, which are a type of smooth space curve, i.e. a curve in three-dimensional space. The helixes may be wound clockwise direction or anti-clockwise direction. The helixes have the property that a tangent line at any point makes a constant angle with a fixed line called the axis. The helical portion 320 of the cable 305 may be the portion of the cable including substantially the entire length (m) of the one or more conductive traces 325. Alternatively, the helical portion 320 of the cable 305 may be the portion of the cable 305 extending between the proximal end 310 and the distal end 315 but not including the electrode assembly and/or the connector. In certain embodiments, the helical portion 320 of the cable 305 comprises one or more characteristics including a radius 330, a helix angle 335, a pitch 340 (rise of the helix for one turn), a helix length 345, and/or a total rise 350 of the helix (see, e.g., FIG. 3B). The radius 330 may be from 200 μm to 900 μm, from 250 μm to 700 μm, or from 400 μm to 650 μm, for example, about 580 μm. The helix angle 335 may be from 10° to 85°, from 40° to 65°, or from 42° to 60°, for example, about 55°. A pitch 340 may be from 100 μm to 2 mm, from 200 μm to 400 μm, or from 600 μm to 1600 μm, for example, about 720 μm. The helix length 345 may be from 5 cm to 150 cm or 50 cm to 100 cm, e.g., about 75 cm, from the proximal end 310 to the distal end 315. The total rise 350 may be from 5 cm to 125 cm or 25 cm to 75 cm, e.g., about 50 cm, from the proximal end 310 to the distal end 315.

In various embodiments, it is desirable that one or more of the characteristics of the helix are selected such that the cable 305 is capable of achieving an elastic elongation % of >20%. The term "elastic", as used herein, may be defined as a material (e.g., the cable) that returns to its original size/shape when force is removed and the "elongation %"=change in total rise*100/original total rise). Achieving an elastic elongation % of >20% is desirable because it allows the cable to stretch and move during and after implantation in the patient. In some embodiments, it is desirable that one or more of the radius, the helix angle, and the pitch are selected such that the cable is capable of being stretched to a stretched total rise of greater than 20% of its original total rise but the cable will return to its original size/shape when the force causing the stretch is removed. In other embodiments, it is desirable that one or more of the radius, the helix angle, and the pitch are selected such that the cable is capable of being stretched to a stretched total rise of greater than 40% of its original total rise but the cable will return to its original size/shape when the force causing the stretch is removed.

Figure 4A:
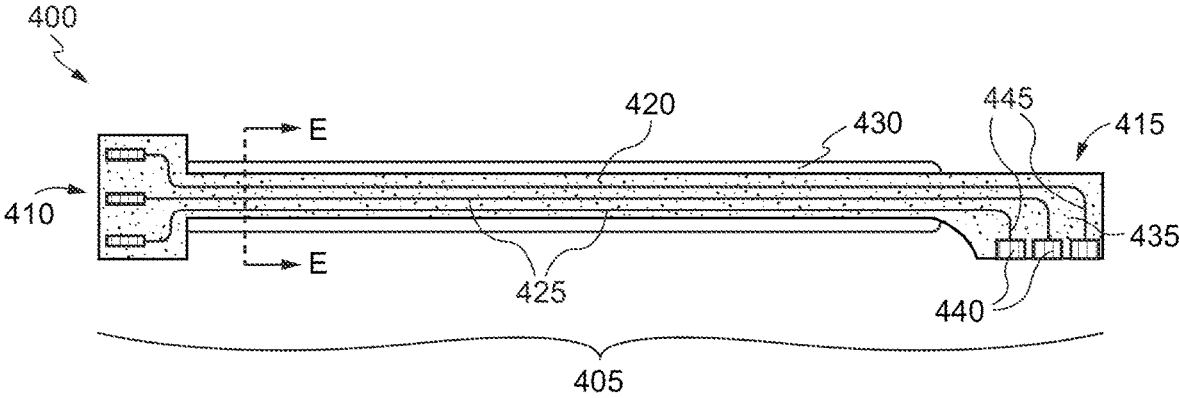
FIGS. 4A, 4B, and 4C show an alternative lead assembly in accordance with various embodiments.
Figure 4B:
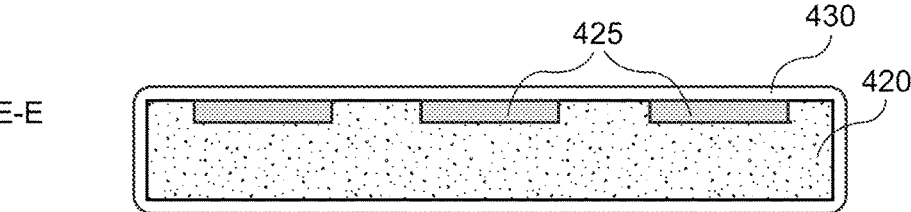
Figure 4C:
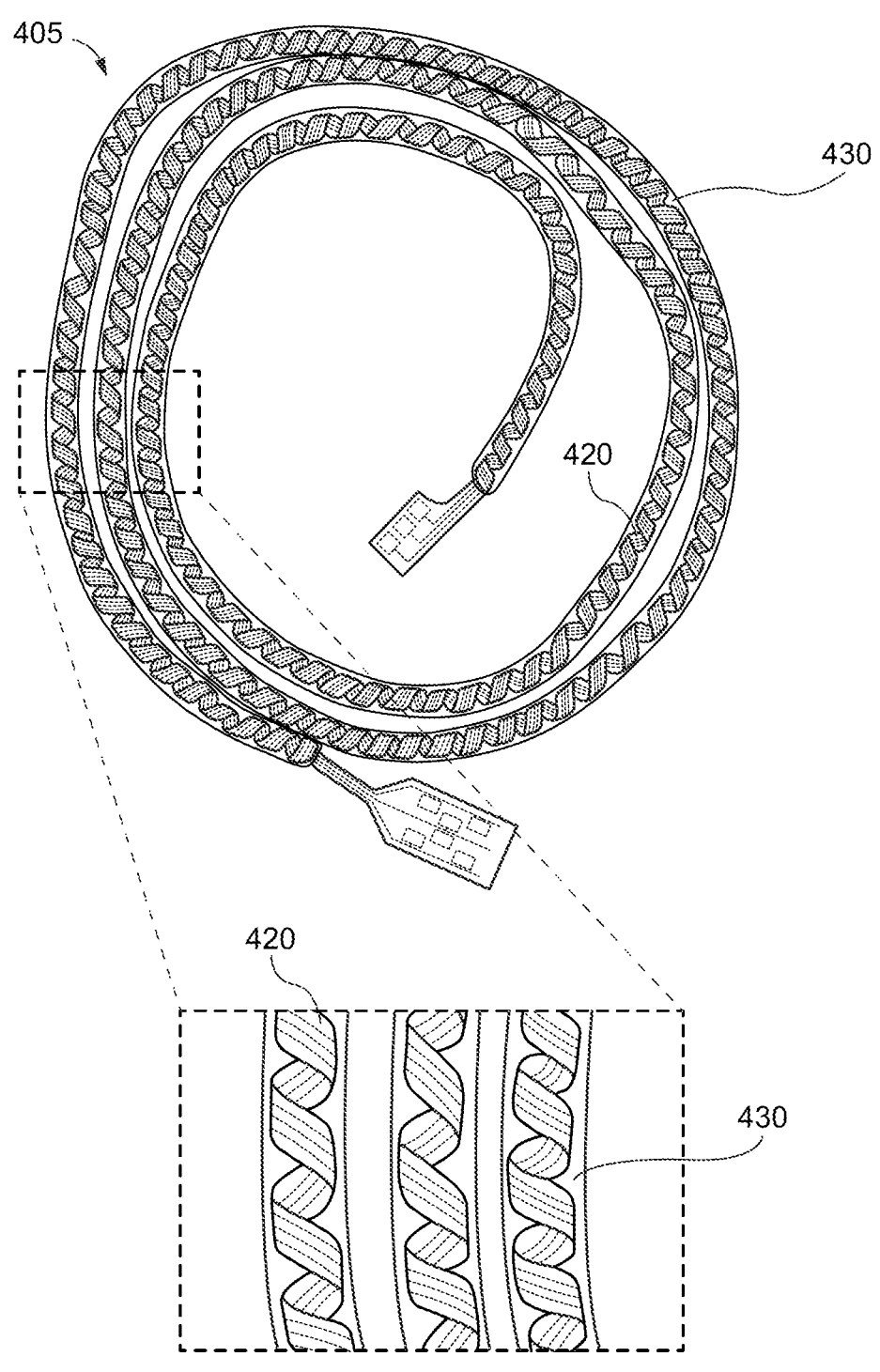

FIGS. 4A-4C show a lead assembly 400 in accordance with aspects of the present disclosure. In various embodiments, the lead assembly 400 comprises a cable 405 having a proximal end 410 and a distal end 415 (e.g., lead assembly 200 as described with respect to FIGS. 2A-2H). In some embodiments, the cable 405 includes a supporting structure 420 with one or more conductive traces 425 and a housing 430. In some embodiments, the lead assembly 400 further includes one or more additional supporting structures that may support one or more additional electronic structures of the assembly such as an electrode, conductor, and/or connector. For example, the lead assembly 400 may further include an electrode assembly 435 comprising one or more electrodes 440. The electrode assembly 435 may be connected to the one or more conductive traces 425 via a wiring layer 445. In some embodiments, the distal 415 end of the lead assembly 400 carries the electrode assembly 435 (e.g., book electrodes, split cuff electrodes, spiral cuff electrodes, epidural electrodes, helical electrodes, probe electrodes, linear electrodes, neural probe, paddle electrodes, and intra-neural electrodes). In other embodiments, the distal end 415 of the lead assembly 400 carries a plurality of the electrode assemblies 435. In certain embodiments, the housing 430 completely encases at least a portion of the supporting structure 420 and the one or more conductive traces 425 (see, e.g., FIGS. 4B and 4C). In other embodiments, the housing 430 completely encases at least a portion of the supporting structure 420 and the one or more conductive traces 425, and extends to partially encase the electrode assembly 440 (e.g., the surfaces of the electrodes are exposed). The housing 430 may be comprised of a medical grade polymer material. In some embodiments, the medical grade polymer is thermosetting or thermoplastic. For example, the medical grade polymer may be a soft polymer such as silicone, a polymer dispersion such as latex, a chemical vapor deposited poly(p-xylylene) polymer such as parylene, or a polyurethane such as Bionate® Thermoplastic Polycarbonate-urethane (PCU) or CarboSil® Thermoplastic Silicone-Polycarbonate-urethan (TSPCU).

Figure 5A:
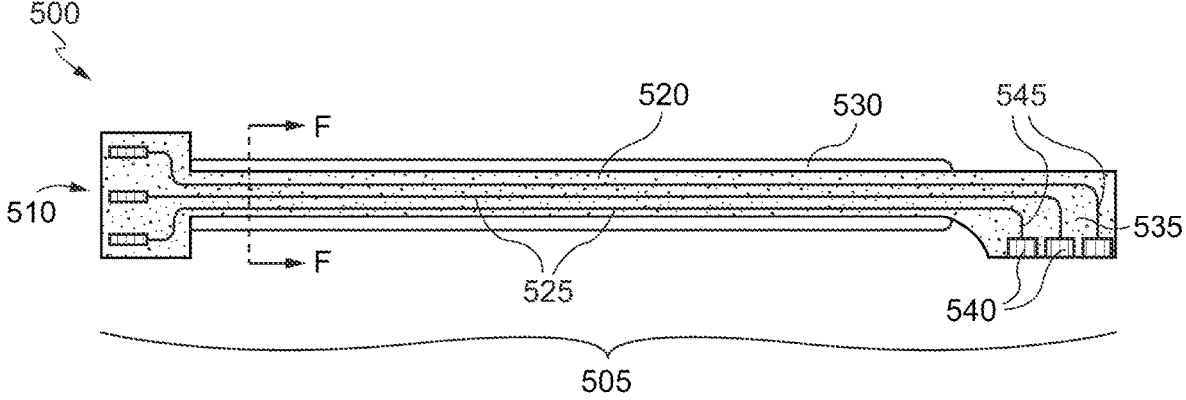
FIGS. 5A, 5B, and 5C show an alternative lead assembly in accordance with various embodiments.
Figure 5B:
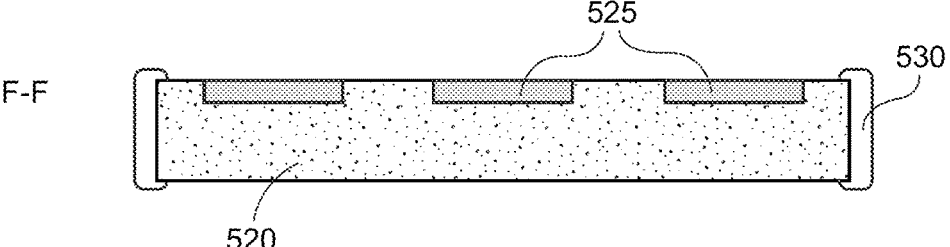
Figure 5C:
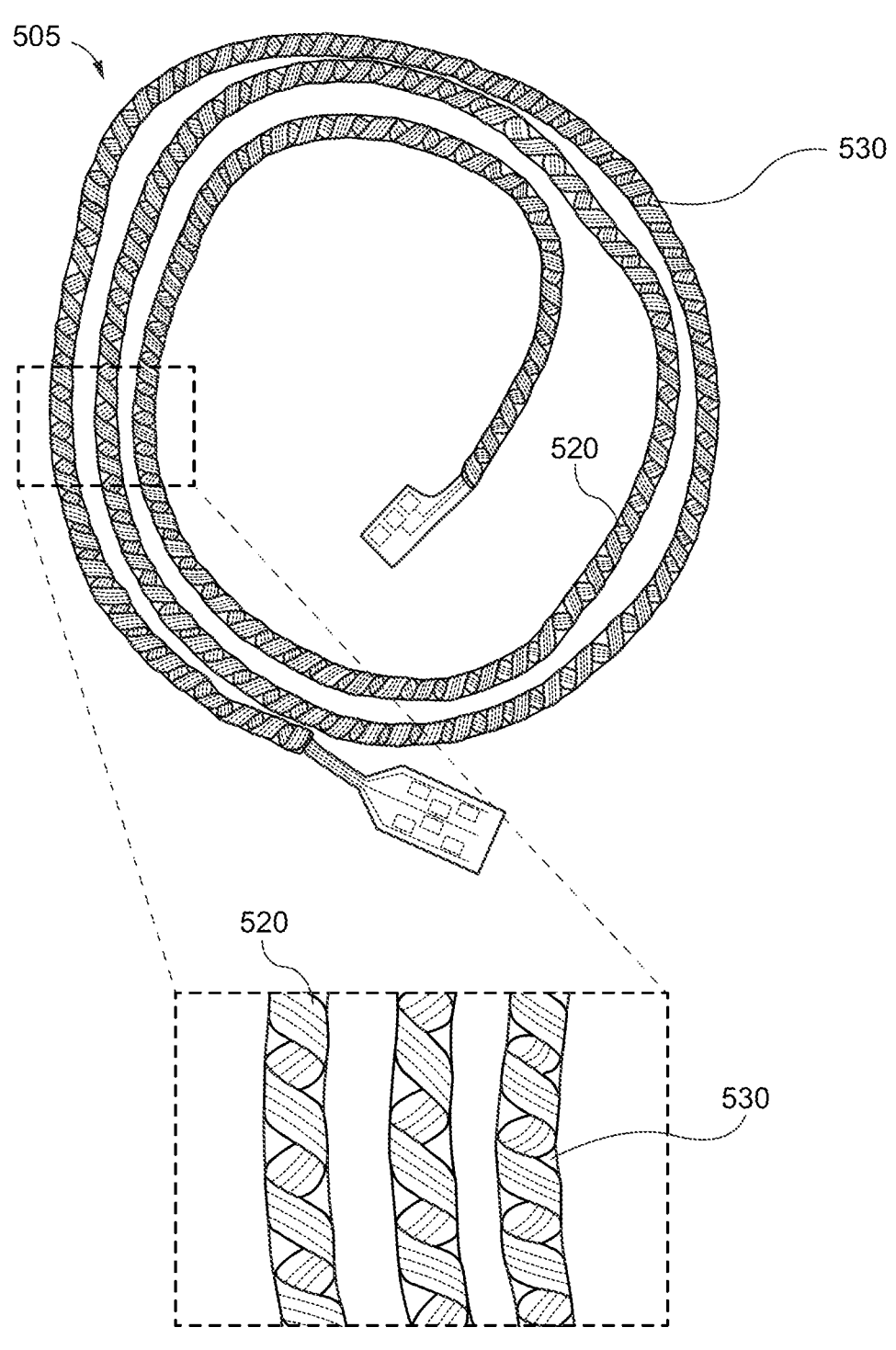

FIGS. 5A-5C show a lead assembly 500 in accordance with aspects of the present disclosure. In various embodiments, the lead assembly 500 comprises a cable 505 having a proximal end 510 and a distal end 515 (e.g., lead assembly 200 as described with respect to FIGS. 2A-2H). In some embodiments, the cable 505 includes a supporting structure 520 with one or more conductive traces 525 and a housing 530. In some embodiments, the lead assembly 500 further includes one or more additional supporting structures that may support one or more additional electronic structures of the assembly such as an electrode, conductor, and/or connector. For example, the lead assembly 500 may further include an electrode assembly 535 comprising one or more electrodes 540. The electrode assembly 535 may be connected to the one or more conductive traces 525 via a wiring layer 545. In some embodiments, the distal end 515 of the lead assembly 500 carries the electrode assembly 535 (e.g., book electrodes, split cuff electrodes, spiral cuff electrodes, epidural electrodes, helical electrodes, probe electrodes, linear electrodes, neural probe, paddle electrodes, and intra-neural electrodes). In other embodiments, the distal end 515 of the lead assembly 500 carries a plurality of electrode assemblies 535. In certain embodiments, the housing 530 is formed coplanar with at least a portion of the supporting structure 520 and the one or more conductive traces 525 (see, e.g., FIGS. 5B and 5C) and encases only a portion of the supporting structure 520 and the one or more conductive traces 525. In other embodiments, the housing 530 is formed coplanar with at least a portion of the supporting structure 520 and the one or more conductive traces 525, and encases only a portion of the supporting structure 520, the one or more conductive traces 525, and the electrode assembly 535. The housing 530 may be comprised of a medical grade polymer material. In some embodiments, the medical grade polymer is thermosetting or thermoplastic. For example, the medical grade polymer may be a soft polymer such as silicone, a polymer dispersion such as latex, a chemical vapor deposited poly(p-xylylene) polymer such as parylene, or a polyurethane such as Bionate® Thermoplastic Polycarbonate-urethane (PCU) or CarboSil® Thermoplastic Silicone-Polycarbonate-urethan (TSPCU).

Figure 6A:
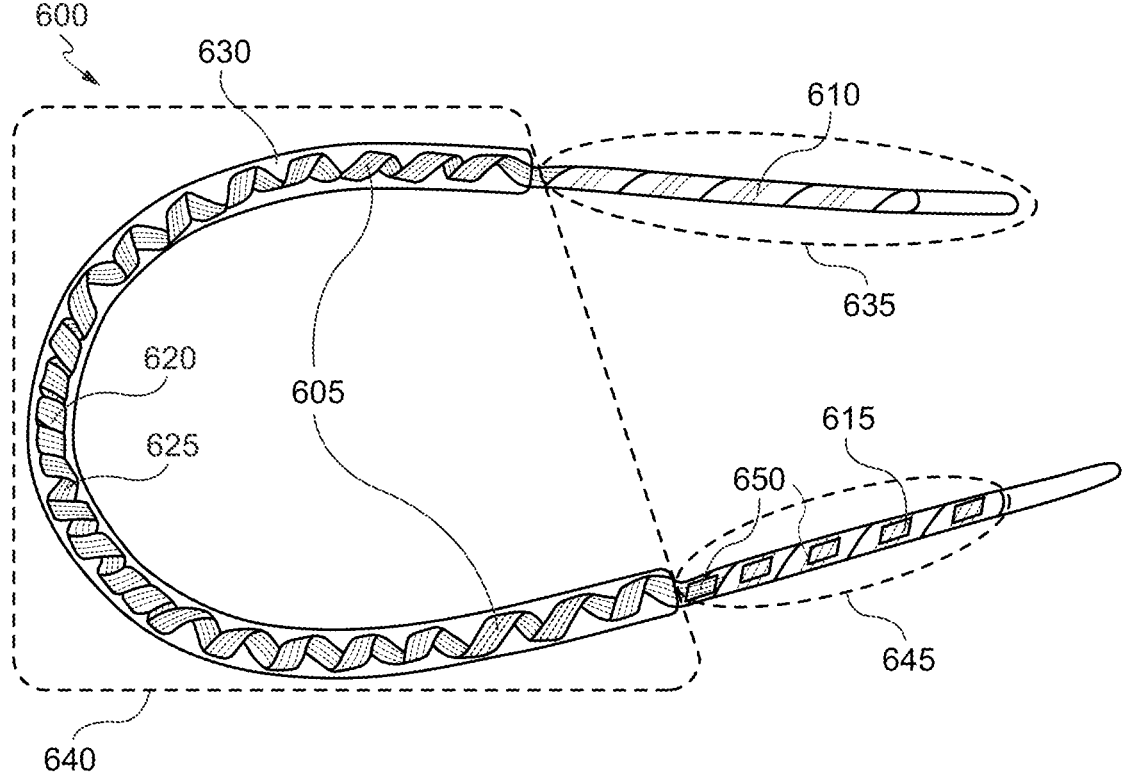
FIGS. 6A, 6B, 6C, and 6D show alternative lead assemblies in accordance with various embodiments.

FIG. 6A shows a lead assembly 600 in accordance with aspects of the present disclosure. In various embodiments, the lead assembly 600 comprises a cable 605 having a proximal end 610 and a distal end 615 (e.g., lead assembly 200 as described with respect to FIGS. 2A-2H). In some embodiments, the cable 605 includes: (i) a supporting structure 620 with one or more conductive traces 625, and (ii) a first housing 630. The housing 630 may be comprised of a medical grade polymer material, as described herein. In accordance with various aspects of the present disclosure, the cable 605 and the housing 630 may be designed for a number of applications. For example, the cable 605 and the housing 630 may be designed for deep brain stimulation, as shown in FIG. 6.

In some embodiments, a first portion 635 of the cable 605 has a first helical structure. The first portion 635 may be defined as the last 1 cm to 15 cm of the cable 605 on the proximal end 610 of the cable 605. In certain embodiments, the first portion 635 comprises tight helixes (e.g., for tissue penetration as with deep brain stimulation or connection to a device such as a neurostimulator) with characteristics including a radius from 200 μm to 900 μm, a helix angle from 10° to 85°, and a pitch from 200 μm to 400 μm. In some embodiments, at least a first portion of the housing 630 completely encases the first portion 635. In other embodiments, at least a first portion of the housing 630 is formed coplanar with the supporting structure 620 and the one or more conductive traces 625 of the first portion 635. In some embodiments, the first portion of the housing 630 is formed coplanar with the first helical portion 635, and the first portion of the housing 630 is comprised of thermosetting polymer such as polyurethane.

In some embodiments, a second portion 640 of the cable 605 has a second helical structure. The second portion 640 may be defined as the middle 5 cm to 150 cm of the cable 605 between the first portion 635 and the third portion 645. In certain embodiments, the second portion 640 comprises loose helixes with characteristics including a radius from 200 μm to 900 μm, a helix angle from 10° to 85°, and a pitch from 600 μm to 1600 μm. In some embodiments, at least a second portion of the housing 630 completely encases the second portion 640. In other embodiments, at least a second portion of the housing 630 is formed coplanar with the supporting structure 620 and the one or more conductive traces 625 of the second portion 640. In some embodiments, the second portion of the housing 630 encases the second helical portion 645, and the second portion of the housing 630 is comprised of silicone.

In some embodiments, a third portion 645 of the cable 605 has a third helical structure. The third portion 645 may be defined as the last 1 cm to 15 cm of the cable 605 on the distal end 615 of the cable 605. In certain embodiments, the third portion 645 comprises tight helixes (e.g., for tissue penetration as with deep brain stimulation or connection to a device such as a neurostimulator) with characteristics including a radius from 200 μm to 900 μm, a helix angle from 10° to 85°, and a pitch from 200 μm to 400 μm. In some embodiments, at least a third portion of the housing 630 completely encases the third portion 645. In other embodiments, at least a third portion of the housing 630 is formed coplanar with the supporting structure 620 and the one or more conductive traces 625 of the third portion 645. In some embodiments, the third portion of the housing 630 is formed coplanar with the third helical portion 645, and the third portion of the housing 630 is comprised of thermosetting polymer such as polyurethane.

In some embodiments, the lead assembly 600 further includes one or more additional supporting structures that may support one or more additional electronic structures of the assembly such as an electrode, sensor, conductor, and/or connector. In certain embodiments, the lead assembly 600 further includes a portion of the supporting structure 620 that is formed as an electrode assembly 650 at the distal end 615. In other embodiments, the lead assembly 600 further includes: (i) a portion of the supporting structure 620 that is formed as an electrode assembly 650 at the distal end 615, and (ii) a multiplexer chip (not shown) formed on the supporting structure 620 at the proximal end 610 or the distal end 615. The multiplexer chip (not shown) may be in electrical connection with one or more electrodes (optionally one or more sensors) of the electrode assembly via the one or more conductive traces 625. In yet other embodiments, the lead assembly 600 further includes: (i) a portion of the supporting structure 620 that is formed as an electrode assembly 650 at the distal end 615, (ii) a multiplexer chip (not shown) formed on the supporting structure 620 at the proximal end 610 or the distal end 615, and/or (iii) a connector formed on the supporting structure 620 at the proximal end 610 of the cable 605 and in electrical connection with the one or more conductive traces 625. The multiplexer chip (not shown) may be in electrical connection with one or more electrodes (optionally one or more sensors) of the electrode assembly via the one or more conductive traces 625.

Figure 6B:
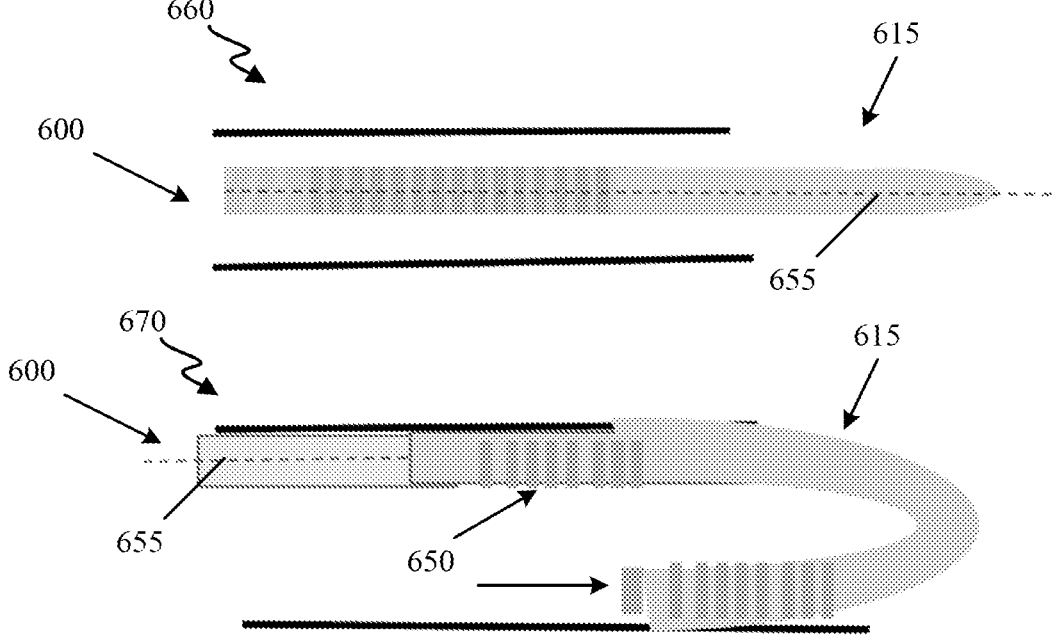
Figure 6C:
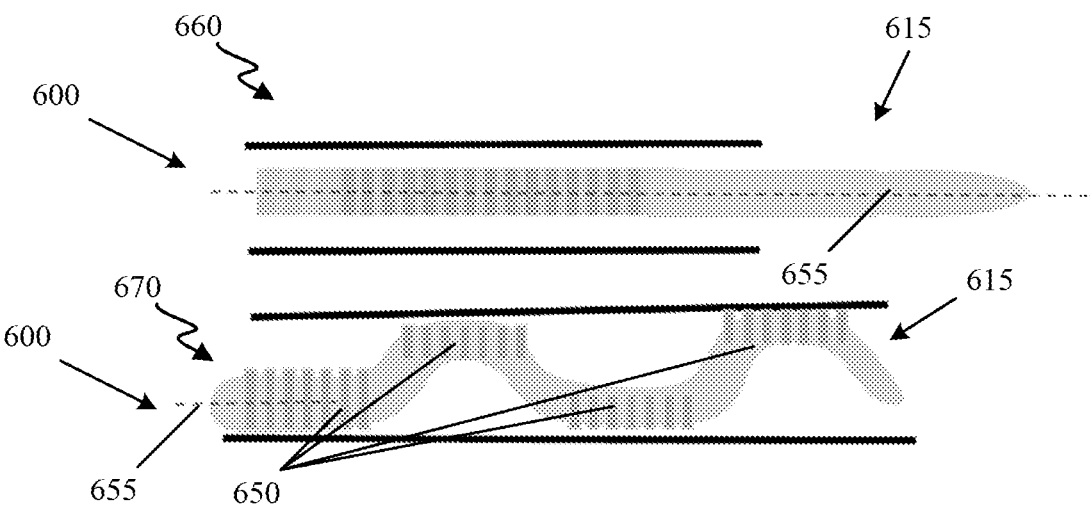
Figure 6D:
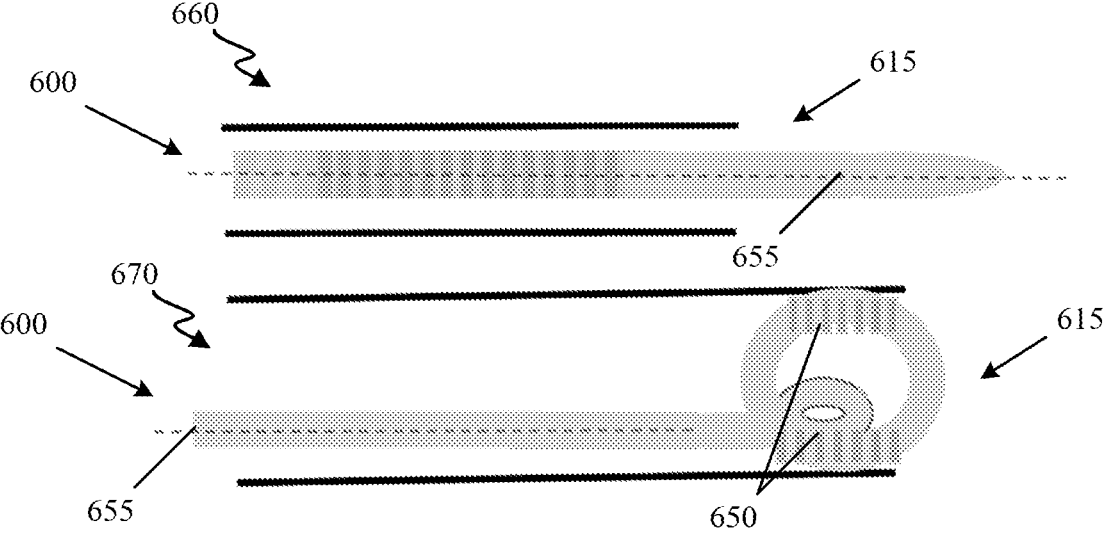

FIGS. 6B, 6C, and 6D show the distal end 615 and electrode assembly 650 of the lead assembly 600 in various configurations. The distal end 615 has at least one curved portion of the supporting structure that is disposed between a first set of electrodes and a second set of electrodes of the electrode assembly 650, and/or (ii) the at least one curved portion of the supporting structure that is disposed between a first set of sensors and a second set of sensors of the electrode assembly 650. In some instances, disclosed herein are monolithic thin-film lead assemblies that can be implanted in biological structures such as veins using a guidewire or a stylet. These lead assemblies can be made isodiametric and under ~1.3 mm outer diameter to be compatible with standard implant tools. Additionally, different distal end lead configurations may be used that allow the lead assemblies to be implanted through a biological structure and deployed in a manner that will not allow the lead assemblies to become dislodged from a given implant location. These shapes or configurations are enabled because of the thermoforming ability of the thin-film lead assembly design. As shown in FIG. 6B, the distal end 615 of the lead assembly 600 is straight when a stylet of guidewire is inserted during which allows for the lead to be navigated through the biological structure (e.g., veins) to a target implant location. Upon situation of the lead at the target implant location, the guidewire or stylet is retracted which is when the distal end 615 of the lead assembly 600 starts to take shape into one or more of the following form factors comprising at least one curved portion: (i) the at least one curved portion is a single curved portion and the curved structure has a shape of a "U" or a "J", or (ii) the at least one curved portion is multiple curved portions and the curved structure has a shape of a "S", a helix, or a involute spiral (see, e.g., FIGS. 6B, 6C, and 6D). This shape at the distal end allows the electrodes and/or sensors of the electrode assembly 650 to be positioned against a biological structure such as a venous wall for sensing and allows for stability.

FIG. 6B shows the "J" or "U" shape on the distal end 615 allowing electrodes and/or sensors of the electrode assembly 650 to be deployed on both sides of a biological structure for better contact. Distal end 615 straightens with stylet or guidewire 655 and takes shape upon retraction. For example, the top portion 660 shows the stylet/guidewire 655 extended which straightens the lead assembly 600 with the electrodes and/or sensors of the electrode assembly 650. The bottom portion 670 shows the stylet/guidewire 655 retracted which allows the lead assembly 600 to take "U" or "J" shape on the distal end 615. This shape acts like a wedge and provides stability to the lead assembly 600, at the same time will not block or occlude the biological structure completely, while allowing enough surface area against the biological structure that can have multiple electrodes and/or sensors in contact with the biological structure.

FIG. 6C shows the helical shape on the distal end 615 allowing electrodes and/or sensors of the electrode assembly 650 to be deployed on both sides of a biological structure for better contact. Distal end 615 straightens with stylet or guidewire 655 and takes shape upon retraction. For example, the top portion 660 shows the stylet/guidewire 655 extended which straightens the lead assembly 600 with the electrodes and/or sensors of the electrode assembly 650. The bottom portion 670 shows the stylet/guidewire 655 retracted which allows the lead assembly 600 to take the helical shape on the distal end 615. This shape acts like a wedge and provides stability to the lead assembly 600, at the same time will not block or occlude the biological structure completely, while allowing enough surface area against the biological structure that can have multiple electrodes and/or sensors in contact with the biological structure.

FIG. 6D shows the spiral shape on the distal end 615 allowing electrodes and/or sensors of the electrode assembly 650 to be deployed on both sides of a biological structure for better contact. Distal end 615 straightens with stylet or guidewire 655 and takes shape upon retraction. For example, the top portion 660 shows the stylet/guidewire 655 extended which straightens the lead assembly 600 with the electrodes and/or sensors of the electrode assembly 650. The bottom portion 670 shows the stylet/guidewire 655 retracted which allows the lead assembly 600 to take the spiral shape on the distal end 615. This shape acts like a wedge and provides stability to the lead assembly 600, at the same time will not block or occlude the biological structure completely, while allowing enough surface area against the biological structure that can have multiple electrodes and/or sensors in contact with the biological structure.

In some embodiments, a method for deploying a monolithic thin-film lead assembly is provided that comprises: obtaining the lead assembly comprising: a lead comprising: a proximal end, a distal end, a supporting structure that extends from the proximal end to the distal end, and a plurality of conductive traces formed on a portion of the supporting structure, where the supporting structure is comprised of one or more layers of dielectric material; an interface formed on the supporting structure at the distal end of the cable, where the interface comprises a plurality of electrodes and/or a plurality of sensors in electrical connection with one or more conductive traces of the plurality of conductive traces, where the plurality of electrodes comprise a first set of electrodes and a second set of electrodes and/or the plurality of sensors comprise a first set of sensors and a second set of sensors; and a guidewire comprising a stylet inserted through the interface, where while the stylet is inserted through the interface, the interface has a first profile, and where the first profile is straight with the first set of electrodes and the second set of electrodes and/or the first set of sensors and the second set of sensors provided in a linear array; inserting, with the guidewire, the lead assembly into a cavity (such as an endovascular cavity) of a subject; moving, with the guidewire, the lead assembly through the cavity to position the interface at a target location (such as a target location for brain computer interfacing); and removing the guidewire and stylet from the cavity while leaving the lead assembly in place with the interface positioned at the target location, where removal of the stylet from the interface allows for the interface to take a second profile having at least one curved portion, where: (i) the at least one curved portion is disposed between the first set of electrodes and the second set of electrodes, and/or (ii) the at least one curved portion is disposed between the first set of sensors and the second set of sensors. In some instances, the method further comprises connecting the cable to a computing device and using the computing device to send a single through the interface to tissue at the target location or receive a signal from the tissue at the target location.

Figure 7:
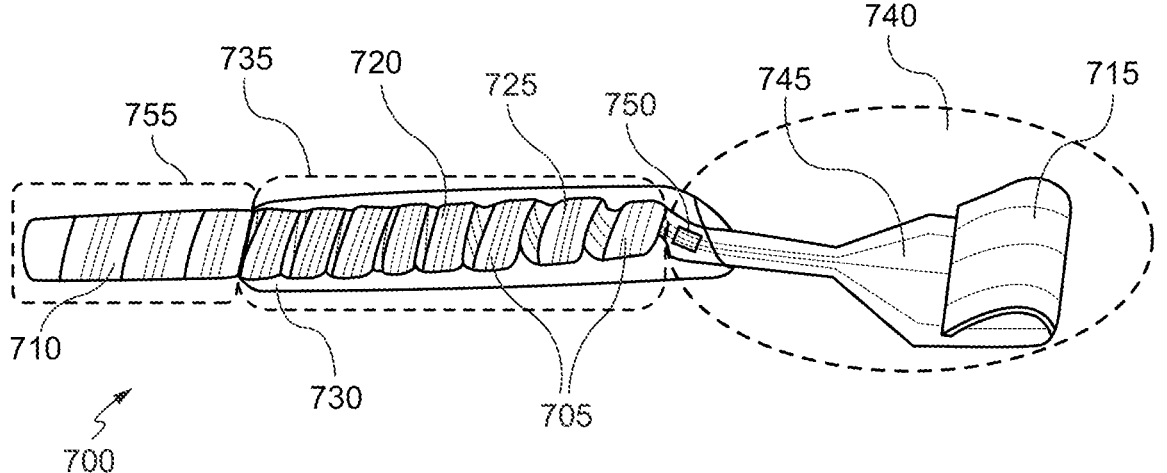
FIG. 7 shows an alternative lead assembly in accordance with various embodiments.

FIG. 7 shows a lead assembly 700 in accordance with aspects of the present disclosure. In various embodiments, the lead assembly 700 comprises a cable 705 having a proximal end 710 and a distal end 715 (e.g., lead assembly 200 as described with respect to FIGS. 2A-2H). In some embodiments, the cable 705 includes: (i) a supporting structure 720 with one or more conductive traces 725, and (ii) an housing 730. The housing 730 may be comprised of a medical grade polymer material, as described herein. In accordance with various aspects of the present disclosure, the cable 705 and the housing 730 may be designed for a number of applications. For example, the cable 705 and the housing 730 may be designed for vagus nerve/artery plexus stimulation, as shown in FIG. 7.

In some embodiments, a first portion 735 of the cable 705 has a helical structure. The first portion 735 may be defined as the middle 5 cm to 150 cm of the cable 705 between the proximal end 710 and the distal end 715. In certain embodiments, the first portion 735 comprises loose helixes with characteristics including a radius from 200 μm to 900 μm, a helix angle from 10° to 85°, and a pitch from 600 μm to 1600 μm. In some embodiments, at least a portion of the housing 730 completely encases the portion 735. In other embodiments, at least a portion of the housing 730 is formed coplanar with the supporting structure 720 and the one or more conductive traces 725 of the first portion 735. In some embodiments, the housing 730 completely encases the helical portion 735, and the housing 730 is comprised of silicone.

In some embodiments, a second portion 740 of the cable 705 has an electrode assembly 745. The second portion 740 may be defined as the last 1 cm to 15 cm of the cable 705 on the distal end 715. In certain embodiments, the second portion 740 comprises a portion of the supporting structure 720 that is thermoformed into book electrodes, split cuff electrodes, spiral cuff electrodes, epidural electrodes, helical electrodes, probe electrodes, linear electrodes, neural probe, paddle electrodes, and intraneural electrodes. In some embodiments, the supporting structure 720 at the distal end 715 of the cable 705 having the electrode assembly 745 formed thereon is thermoformed into a cuff structure. Additionally, a multiplexer chip 750 may formed on or within the supporting structure 720 at the proximal end 710 or the distal end 715. The multiplexer chip 750 may be in electrical connection with one or more electrodes (optionally one or more sensors) of the electrode assembly 745 via the one or more conductive traces 725. In some embodiments, at least a portion of the housing 730 partially encases the second portion 740. In other embodiments, at least a portion of the housing 730 is formed coplanar with one or more electrodes (optionally one or more sensors) of the electrode assembly 745.

In some embodiments, a third portion 755 of the cable 705 has another helical structure. The third portion 755 may be defined as the last 1 cm to 15 cm of the cable 705 on the proximal end 710. In certain embodiments, the third portion 755 comprises tight helixes (e.g., for connection to a device such as a neurostimulator) with characteristics including a radius from 200 μm to 900 μm, a helix angle from 10° to 85°, and a pitch from 200 μm to 400 μm. In some embodiments, at least a portion of the housing 730 completely encases the third portion 755. In other embodiments, at least a portion of the housing 730 is formed coplanar with the supporting structure 720 and the one or more conductive traces 725 of the third portion 755.

In other embodiments, the third portion 755 of the cable 705 includes one or more additional supporting structures that may support one or more additional electronic structures of the assembly such as an electrode, sensor, conductor, and/or connector. The third portion 755 may be defined as the last 1 cm to 15 cm of the cable 705 on the proximal end 710. In certain embodiments, the third portion 755 comprises a connector formed on the supporting structure 720 at the proximal end 710 of the cable 705 and in electrical connection with the one or more conductive traces 725. In some embodiments, at least a portion of the housing 730 completely partially encases the third portion 755. In other embodiments, at least a portion of the housing 730 is formed coplanar with the supporting structure 720 and the connector (e.g., a bond pad) of the third portion 755.

While the lead assemblies have been described at some length and with some particularity with respect to a specific design and/or performance need, it is not intended that the lead assemblies be limited to any such particular design and/or performance need. Instead, it should be understood the lead assemblies described herein are exemplary embodiments, and that the lead assemblies are to be construed with the broadest sense to include variations of the specific design and/or performance need described herein, as well as other variations that are well known to those of skill in the art. In particular, the shape and location of components and layers in the lead assemblies may be adjusted or modified to meet specific design and/or performance needs. Furthermore, it is to be understood that other structures have been omitted from the description of the lead assemblies for clarity. The omitted structures may include sensor structures, insulating layers, interconnect components, passive devices, etc.

IV. Methods For Fabricating a Lead Assembly

FIGS. 8A-8H show structures and respective processing steps for fabricating a thin-film lead assembly 800 (e.g., as described with respect to FIG. 2A-2H, 3A, 4B, 4A, 4B, 4C, 5A, 5B, 5C, 6, or 7) in accordance with various aspects of the invention. It should be understood by those of skill in the art that the thin-film lead assembly can be manufactured in a number of ways using a number of different tools. In general, however, the methodologies and tools used to form the structures of the various embodiments can be adopted from integrated circuit (IC) technology. For example, the structures of the various embodiments, e.g., supporting structure, conductive traces, electrodes, sensors, wiring layers, bond/contact pads, etc., may be built with or without a substrate and realized in films of materials patterned by photolithographic processes. In particular, the fabrication of various structures described herein may typically use three basic building blocks: (i) deposition of films of material on a substrate and/or previous film(s), (ii) applying a patterned mask on top of the film(s) by photolithographic imaging, and (iii) etching the film(s) selectively to the mask.

As used herein, the term "depositing" may include any known or later developed techniques appropriate for the material to be deposited including but not limited to, for example: chemical vapor deposition (CVD), low-pressure CVD (LPCVD), plasma-enhanced CVD (PECVD), semi-atmosphere CVD (SACVD) and high density plasma CVD (HDPCVD), rapid thermal CVD (RTCVD), ultra-high vacuum CVD (UHVCVD), limited reaction processing CVD (LRPCVD), metalorganic CVD (MOCVD), sputtering deposition, ion beam deposition, electron beam deposition, laser assisted deposition, thermal oxidation, thermal nitridation, spin-on methods, physical vapor deposition (PVD), atomic layer deposition (ALD), chemical oxidation, molecular beam epitaxy (MBE), plating (e.g., electroplating), or evaporation.

Figure 8A:
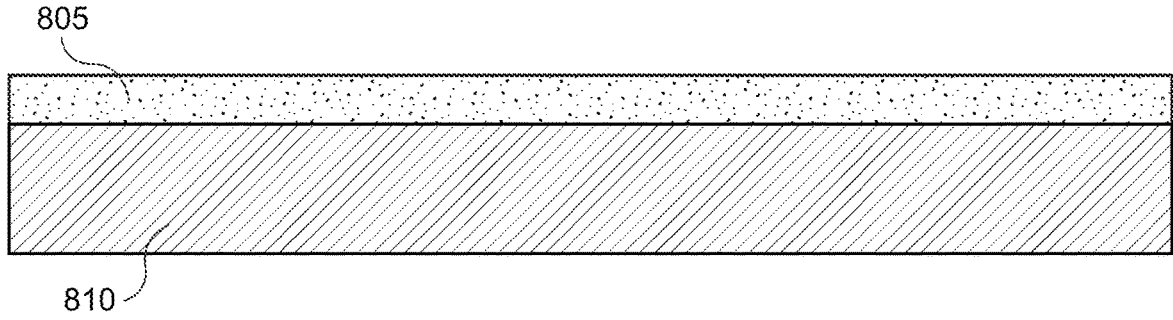
FIGS. 8A-8G show cross-sectional side views and a lead assembly view illustrating a method of forming a lead assembly in accordance with various embodiments.

FIG. 8A shows a beginning structure (a supporting structure) comprising a first polymer layer 805 overlying an optional substrate 810 (e.g., a backer). In various embodiments, the beginning structure may be provided, obtained, or fabricated as a single wafer or panel having a diameter, length, and/or width of less than 15 cm. The substrate 810 may be comprised of any type of metallic or non-metallic material. For example, the substrate 810 may be comprised of but not limited to silicon, germanium, silicon germanium, silicon carbide, and those materials consisting essentially of one or more Group III-V compound semiconductors having a composition defined by the formula AlX1GaX2InX3AsY1PY2NY3SbY4, where X1, X2, X3, Y1, Y2, Y3, and Y4 represent relative proportions, each greater than or equal to zero and X1+X2+X3+Y1+Y2+Y3+Y4=1 (1 being the total relative mole quantity). Substrate 810 may additionally or alternatively be comprised of Group II-VI compound semiconductors having a composition ZnA1CdA2SeB1TeB2, where A1, A2, B1, and B2 are relative proportions each greater than or equal to zero and A1+A2+B1+B2=1 (1 being a total mole quantity). The processes to provide, obtain, or fabricate substrate 810, as illustrated and described, are well known in the art and thus, no further description is provided herein.

The first polymer layer 805 may be comprised of dielectric material (i.e., an insulator). The dielectric material may be selected from the group of electrically nonconductive materials consisting of organic or inorganic polymers, ceramics, glass, glass-ceramics, polyimide-epoxy, epoxy-fiberglass, and the like. In certain embodiments, the dielectric material is a thermoplastic or thermosetting polymer. For example, the polymer may be a polyimide, a LCP, parylene, a PEEK, or combinations thereof. The forming of the first polymer layer 805 may include depositing and curing a dielectric material directly on the substrate 810 without an adhesion promoter. For example, a solution comprised of an imidizable polyamic acid compound dissolved in a vaporizable organic solvent without an adhesion promoter may be deposited (e.g., spin coated) onto the substrate 810. The solution may then be heated at a temperature, preferably less than 250° C., to imidize the polyamic acid compound to form the desired polyimide and vaporize the solvent. The first polymer layer 805 may then be thinned to a desired thickness by planarization, grinding, wet etch, dry etch, oxidation followed by oxide etch, or any combination thereof. This process can be repeated to achieve a desired thickness for the first polymer layer 805. In some embodiments, the first polymer layer 805 may have a thickness from 10 μm to 150 μm. In some embodiments, the first polymer layer 805 may have a thickness from 25 μm to 100 μm. In some embodiments, the first polymer layer 805 may have a thickness from 35 μm to 75 μm.

Figure 8B:
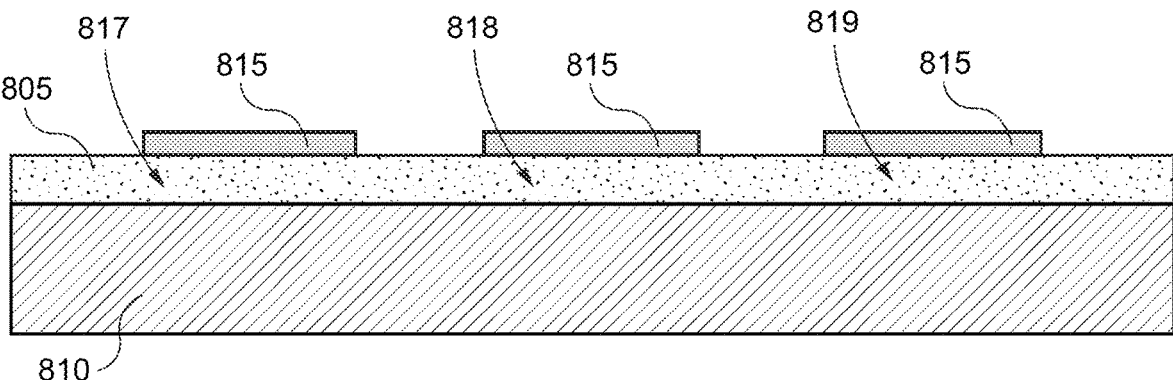

FIG. 8B shows conductive traces 815 formed in a pattern on a first portion (e.g., region) of the first polymer layer 805. In some embodiments, forming the conductive traces 815 may include depositing a seed layer (e.g., a copper (Cu) seed layer, a gold (Au) seed layer, a silver (Ag) seed layer, a gold/chromium (Au/Cr) seed layer, platinum (Pt) seed layer, platinum/iridium (Pt/Ir) seed layer, etc.) over the first polymer layer 805. The seed layer may be configured to enable forming of a conductive trace on the first polymer layer 805 (e.g., through Cu electroplating, Au electroplating, Sn electroplating, Ag electroplating, Au/Cr electroplating, platinum (Pt) electroplating, platinum/iridium (Pt/Ir) electroplating, etc.). Optionally, and prior to forming of the seed layer, an adhesion layer may be deposited over the first polymer layer 805 to enable adequate application of the seed layer. Deposition of either or both of the adhesion layer and seed layer may include sputter deposition Following deposition of the seed layer, a resist pattern may be formed above the first polymer layer 805. The resist pattern may include openings that align over at least a portion of the first polymer layer 805 for forming of a plurality of conductive traces 815 (e.g., a conductive layer with a cross-sectional thickness of 0.5 μm to 100 μm or from 25 μm to 50 μm) on the first polymer layer 805. For example, the resist may be patterned with openings to form: (i) a first conductive trace 815 over a first region 817 of the first polymer layer 805, (ii) a second conductive trace 815 over a second region 818 of the first polymer layer 805, and (iii) a third conductive trace 815 over a third region 819 of the first polymer layer 805. In various embodiments, the openings of the resist pattern may have a spiral pattern such that the formed plurality of conductive traces 815 have a spiral shape, e.g. as shown in FIG. 2C. The spiral shape may include characteristics designed to maximize the length of the lead assembly 800 that can be fabricated from a single wafer or panel. In some embodiments, characteristics of the spiral shape include a predetermined number of turns and a predetermined pitch (p) between each of the turns to maximize the overall length obtainable for the lead assembly 800.

In certain embodiments, the spiral shape has greater than 2 turns, for example from 2 to 25 turns, and a pitch between each of the turns from 10 μm to 1 cm or from 250 μm to 2 mm, for example about 250 μm. Accordingly, the spiral shape can maximize the length of the lead assembly 800 that can be fabricated from a single wafer or panel. For example, a single wafer or panel with a limited diameter, length, and/or width of less than 10 cm, can be used to fabricate a lead assembly 800 with a length of 5 cm to 150 cm or 50 cm to 100 cm, e.g., about 75 cm, using the spiral shape. It should be understood by those of skill in the art that different patterns and shapes are also contemplated by the present invention to maximize the length of the lead assembly 800.

In various embodiments, the conductive traces 815 may be deposited through electroplating (e.g., through Cu electroplating, Au electroplating, Sn electroplating, Ag electroplating, Au/Cr electroplating, etc.) and may be positioned over at least a portion of the first polymer layer 805 (e.g., the first region 817, the second region 818, and the third region 819). The electroplating may be performed at a current density of about 4.0 mA/cm2 to about 4.5 mA/cm2. In some embodiments, the exposed area or portion of the first polymer layer 805 may encompass about 8 cm² to about 10 cm². The current may be about 14 mA to about 18 mA and the duration may be from about 110 minutes to about 135 minutes to form the conductive traces 815 having a thickness of about 8 μm to about 10 μm. In other embodiments, the exposed area or portion of the first polymer layer 805 may encompass about 10 cm² to about 18 cm². The current may be about 18 mA to about 28 mA and the duration may be from about 35 minutes to about 50 minutes to form the wiring layer 815 having a thickness of about 2 μm to about 5 μm.

Following the deposition of the conductive traces 815, the intermediate structure may be subjected to a strip resist to remove the resist pattern and expose portions of the seed layer (portions without wire formation), and optionally the adhesion layer. The exposed portions of the seed layer, and optionally the adhesion layer, may then be subjected to an etch (e.g., wet etch, dry etch, etc.) to remove those portions, thereby isolating the conductive traces 815 over at least a portion of the first polymer layer 805.

Figure 8C:
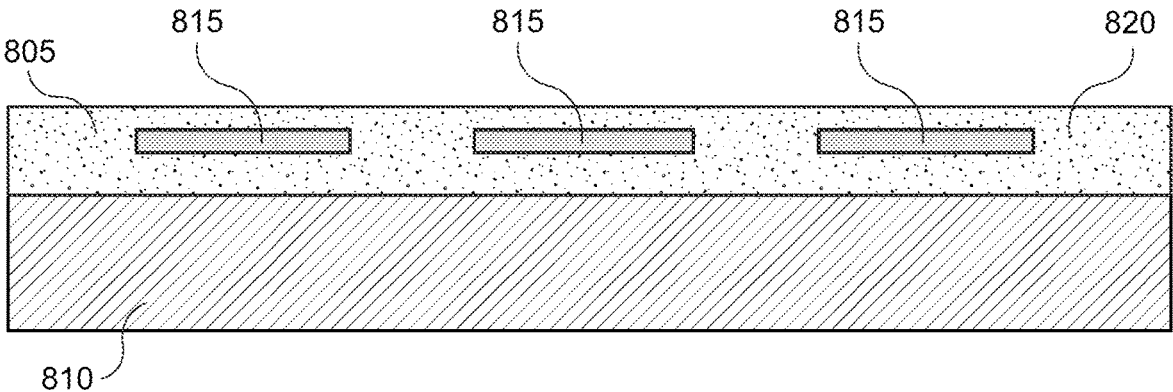

FIG. 8C shows an optional second polymer layer 820 formed over the conductive traces 815 and the first portion of the polymer layer 805. The second polymer layer 820 may be comprised of dielectric material (i.e., an insulator). The dielectric material may be selected from the group of electrically nonconductive materials consisting of organic or inorganic polymers, ceramics, glass, glass-ceramics, polyimide-epoxy, epoxy-fiberglass, and the like. In certain embodiments, the dielectric material is a thermoplastic or thermosetting polymer. For example, the polymer may be a polyimide, a LCP, silicone, parylene, a PEEK, or combinations thereof. The second polymer layer 820 may be comprised of the same material or a different material from that of the first polymer layer 805.

The forming of the second polymer layer 820 may include depositing and curing of a polymer material directly on the conductive traces 815 and the first polymer layer 805. For example, a solution comprised of an imidizable polyamic acid compound dissolved in a vaporizable organic solvent may be applied to the conductive traces 815 and the first polymer layer 805. The solution may then be heated at a temperature, preferably less than 250° C., to imidize the polyamic acid compound to form the desired polyimide and vaporize the solvent. The second polymer layer 820 may then be thinned to a desired thickness by planarization, grinding, wet etch, dry etch, oxidation followed by oxide etch, or any combination thereof. This process can be repeated to achieve a desired thickness for the second polymer layer 820. In some embodiments, the second polymer layer 820 may have a thickness from 1.0 μm to 50.0 μm. In some embodiments, the second polymer layer 820 may have a thickness from 4.0 μm to 15.0 μm. In some embodiments, the second polymer layer 820 may have a thickness from 5.0 μm to 7.0 μm.

Figure 8D:
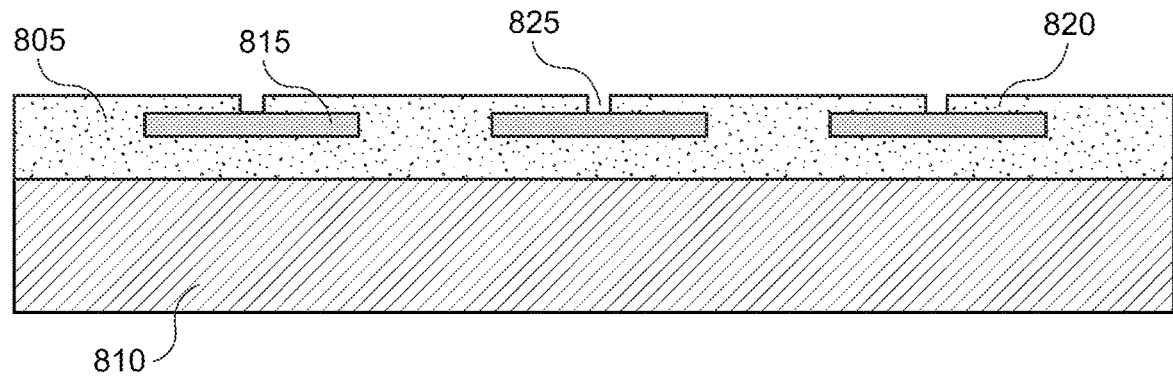

In various embodiments, the lead assembly 800 may further comprise one or more additional supporting structures that may support one or more additional electronic structures of the assembly such as an electrode, sensor, conductor, and/or connector. FIG. 8D shows forming an electrode assembly on the supporting structure 805/810 formed in FIG. 8A that is electrically connected to the conductive traces 815 formed in FIG. 8B. In some embodiments, forming the electrode assembly comprises forming a wiring layer 822 in a pattern on a second portion of the first polymer layer 805. The wiring layer 822 may be formed at the same time as forming the conductive traces 815, or may be formed subsequent to forming the conductive traces 815. For example, the wiring layer 822 and the conductive traces 815 may be deposited as a continuous layer of conductive material, or may be deposited as two separate metallization layers of conductive material that are in electrical contact with one another. The wiring layer 822 may be formed in the same manner as described in detail with respect to the conductive traces 815.

In some embodiments, forming the electrode assembly further comprises forming the second polymer layer 820 over the wiring layer and the second portion of the first polymer layer 805. As described herein, the second polymer layer 820 may be comprised of dielectric material (i.e., an insulator) selected from the group of electrically nonconductive materials consisting of organic or inorganic polymers, ceramics, glass, glass-ceramics, polyimide-epoxy, epoxy-fiberglass, and the like. In certain embodiments, the dielectric material is a thermoplastic or thermosetting polymer. For example, the polymer may be a polyimide, a LCP, parylene, silicone, a PEEK, or combinations thereof. The second polymer layer 820 may be comprised of the same material or a different material from that of the first polymer layer 805.

Figure 8E:
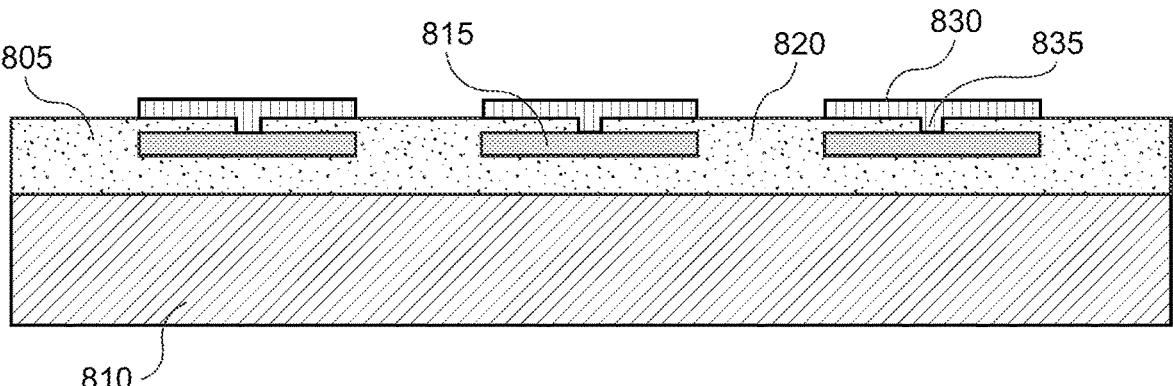

In some embodiments, forming the electrode assembly further comprises forming contact vias 825 in the second polymer layer 820 to the wiring layer 822. The contact vias can e.g. be formed using conventional lithographic, etching, and cleaning processes, known to those of skill in the art. FIG. 8E shows electrodes (optionally one or more sensors) 830 and contacts 835 formed on and within the contact vias 825 to the portion of the top surface the conductive traces 815. In various embodiments, the electrodes 830 (optionally one or more sensors) and contacts 835 may be formed using conventional processes. For example, a conductive material may be blanket deposited on the second polymer layer 820, including within the contact vias 825 and in contact with the portion of the top surface the wiring layer 822. The conductive material may be copper (Cu), gold (Au), silver (Ag), gold/chromium (Au/Cr), platinum (Pt), platinum/iridium (Pt/Ir), titanium (Ti), gold/titanium (Au/Ti), or any alloy thereof, for example. Once the conductive material is deposited, the conductive material may be patterned using conventional lithography and etching processes to form at least one electrode 830 or a pattern of electrodes 830 as shown in FIG. 8E, for example. In some embodiments, at least one electrode 830 is formed on the second polymer layer 820 such that the at least one electrode 830 is in electrical contact with at least a portion of a top surface of the wiring layer 822. In some embodiments, the pattern of electrodes 830 may include each electrode 830 spaced apart from one another via a portion or region 840 of the second polymer layer 820. It should be understood by those of skill in the art that different patterns are also contemplated by the present invention.

Figure 8F:
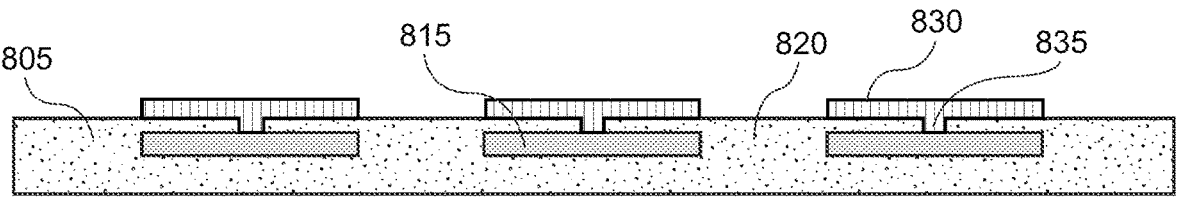

FIG. 8F shows an intermediate structure 845 of the thin-film lead assembly 800 including the first polymer layer 805, the conductive traces 815, the wiring layer 822, the second polymer layer 820, the electrodes 830, and the contacts 835 detached from the substrate 810. In some embodiments, detaching the thin-film lead assembly 800 from the substrate 810 may include removal of the substrate (e.g., selective etching), and cleaning (e.g., a step-wise rinsing process) at least top surfaces of the electrodes 830 and the second polymer layer 820 with acetone, isopropyl alcohol, non-ionic surfactant, a liquid detergent system, and/or deionized water to remove residual material such as remaining adhesive material.

Figure 8G:
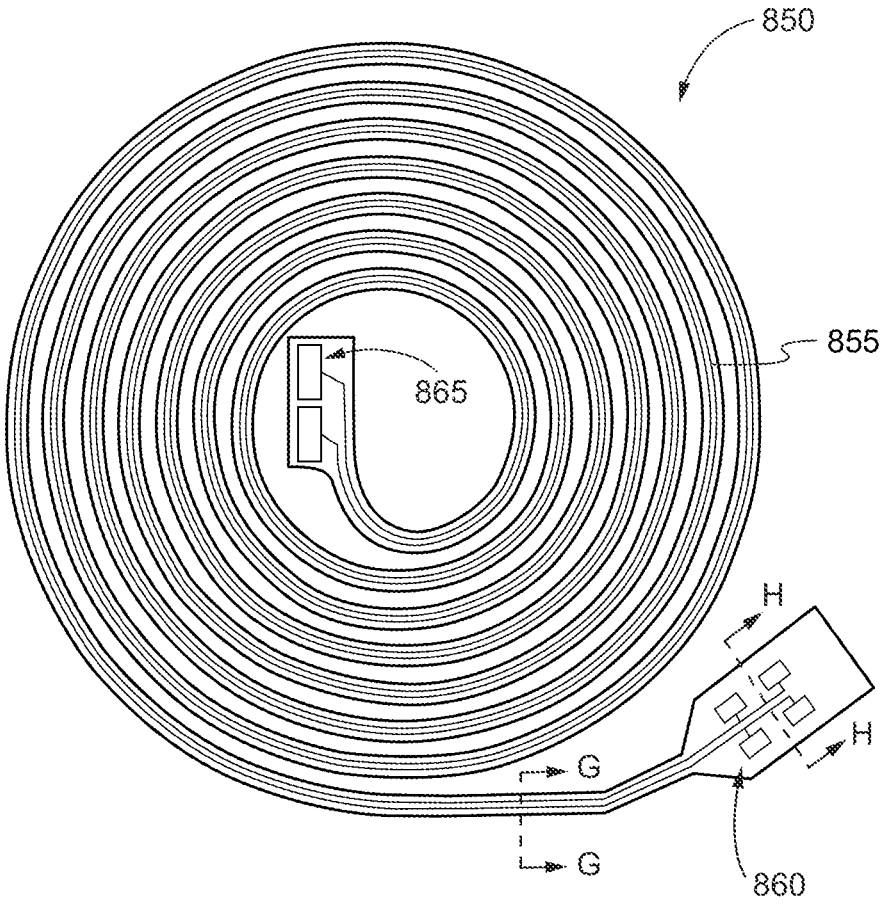

FIG. 8G shows a final monolithic structure 850 of the thin-film lead assembly 800 including a cable 855, optionally an electrode assembly 860, and optionally a connector 865 that is cut from the first polymer layer 805. For example, the thin-film lead assembly 800 may be cut from the first polymer layer 805, and comprises the plurality of conductive traces 815 in the spiral pattern on the first polymer layer 805 and the at least one electrode 830 (optionally one or more sensors) on the second polymer layer 820 electrically connected to the plurality of conductive traces 815. In some embodiments, the cutting is accomplished using a laser and known techniques. As should be understood, FIGS. 8A-8C and 8F shows steps for forming a portion of the cable 855 denoted by line G-G, whereas FIGS. 8A-8F shows steps for forming a portion of the electrode assembly 860 denoted by line H-H.

In some instances, the electrode assembly 860 is an interface comprising a plurality of electrodes and/or a plurality of sensors in electrical connection with one or more conductive traces of the plurality of conductive traces. The plurality of electrodes comprise a first set of electrodes and a second set of electrodes and/or the plurality of sensors comprise a first set of sensors and a second set of sensors. The supporting structure at the distal end of the cable comprises at least one curved portion. The at least one curved portion of the supporting structure is disposed between the first set of electrodes and the second set of electrodes, and/or the at least one curved portion of the supporting structure is disposed between the first set of sensors and the second set of sensors. The interface may be formed by: forming a wiring layer on a second portion of the first polymer layer, where the forming the wiring layer comprises depositing the conductive material in electrical contact with the plurality of conductive traces; depositing a second polymer layer on the wiring layer and the second portion of the first polymer layer; forming a plurality of electrodes and/or a plurality of sensors on the second polymer layer such that the plurality of electrodes and/or the plurality of sensors are in electrical contact with at least a portion of a top surface of the wiring layer; where the plurality of electrodes comprise a first set of electrodes and a second set of electrodes and/or the plurality of sensors comprise a first set of sensors and a second set of sensors; forming at least one curved portion in the second portion of the first polymer layer and the second polymer layer, where the at least one curved portion is formed by wrapping the interface around a mandrel or placing the interface in a mold, and where: (i) the at least one curved portion is disposed between the first set of electrodes and the second set of electrodes, and/or (ii) the at least one curved portion is disposed between the first set of sensors and the second set of sensors; and heating the interface while wrapped around the mandrel or placed in the mold to thermoform the second portion of the first polymer layer and the second polymer layer into a curved structure comprising the at least one curved portion.

In some instances, the at least one curved portion is a single curved portion and the curved structure has a shape of a "U" or a "J". In some instances, the at least one curved portion is multiple curved portions and the curved structure has a shape of a "S", a helix, or a involute spiral. In some instances, the method further comprises: inserting a guidewire having a stylet though the interface causing the at least one curved portion to straighten, which forces the curved structure into a linear structure.

Figure 9A:
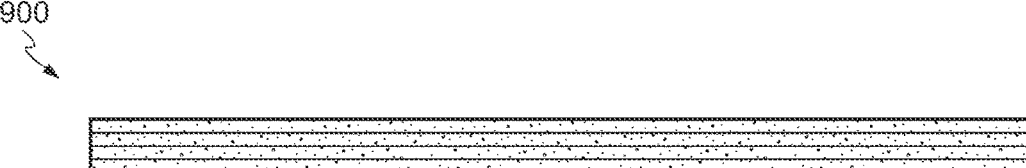
FIGS. 9A-9D show lead assembly views illustrating a method of forming a lead assembly in accordance with various embodiments.

FIGS. 9A-9D show structures and respective processing steps for fabricating an alternative thin-film lead assembly 900 (e.g., a lead assembly having a helical portion) in accordance with various aspects of the invention. FIG. 9A shows a beginning structure 905 for a cable including a plurality of conductive traces 910 formed on or within a supporting structure 915. The cable 910 may further include an electrode assembly 920 comprising a multi-electrode array 925 (optionally one or more sensors) formed at a distal end of the cable. The beginning structure 905 may be formed in accordance with the processes describe herein with reference to FIGS. 8A-8F. For example, the beginning structure 905 may be laser cut in a spiral design from a wafer or panel fabricated with electroplated traces.

Figure 9B:
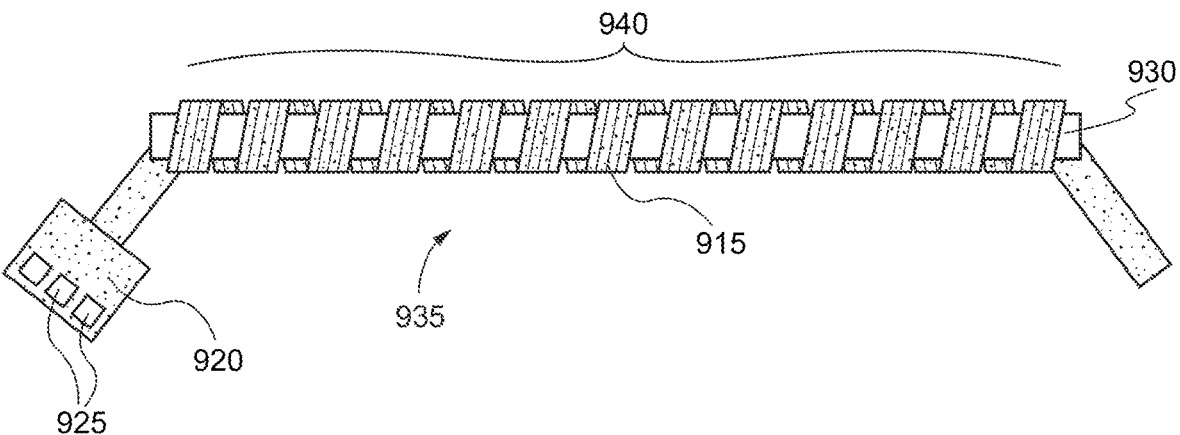

FIG. 9B shows a portion of the cable wound (clockwise direction or anti-clockwise direction) into a helical pattern on a mandrel 930 to form an intermediate structure 935 with a helical portion 940. In various embodiments, the mandrel 930 is selected and the winding is controlled such that the helical portion 940 comprises one or more characteristics including a radius, a helix angle, a pitch, a helix length, and a total rise of the helix. The radius is dictated by the outer diameter of the mandrel 930 and may be from 200 μm to 900 μm, from 250 μm to 700 μm, or from 400 μm to 650 μm, for example, about 580 μm. The helix angle is dictated by controlling the winding and may be from 10° to 85°, from 40° to 65°, or from 42° to 60°, for example, about 55°. The pitch is dictated by controlling the winding and may be may be from 100 μm to 2 mm, from 250 μm to 1100 μm, or from 400 μm to 950 μm, for example, about 720 μm. The helix length is dictated by controlling the winding and may be from 5 cm to 150 cm or 50 cm to 100 cm, e.g., about 75 cm, from the proximal end to the distal end. The total rise is dictated by controlling the winding and may be from 5 cm to 125 cm or 25 cm to 75 cm, e.g., about 50 cm, from the proximal end to the distal end. In some embodiments, the mandrel 930 comprises a coating such as polytetrafluoroethylene (PTFE) for easier removal of the cable 910 from the mandrel 930.

Figure 9C:
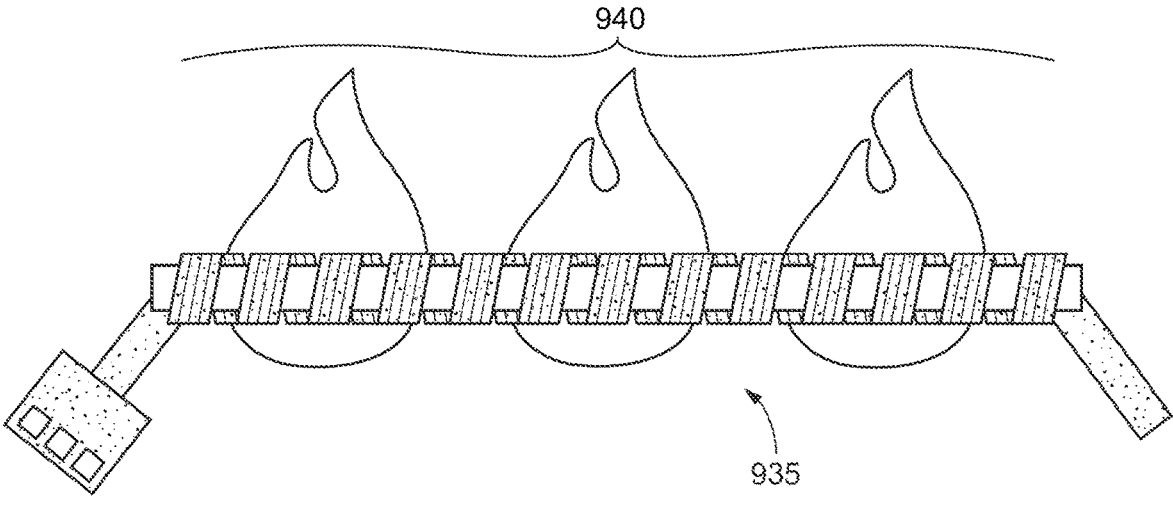
Figure 9D:
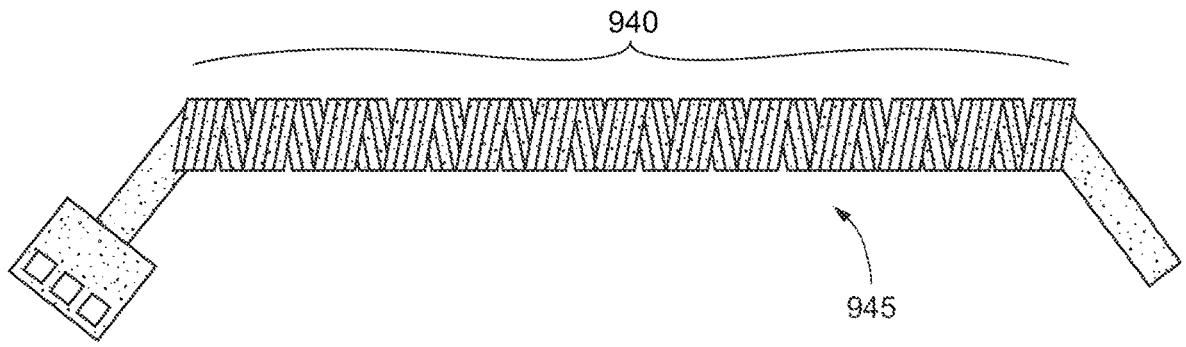

FIG. 9C shows the intermediate structure 935 with a helical portion 940 being heated to thermoform intermediate structure 935 with a helical portion 940 into a final structure 945. The heating process may include baking the structure in an oven, use of a heat gun, application of hot air, like methods, or any combination thereof. In various embodiments, the intermediate structure 935 is heated at 135° C. to 165° C., for example about 150° C., for 25 to 40 minutes, for example 30 minutes. Thereafter, the intermediate structure 935 is cooled (e.g., at ambient temperature) and withdrawn from the mandrel to obtain the final structure 945 shown in FIG. 9D.

Figure 10A:
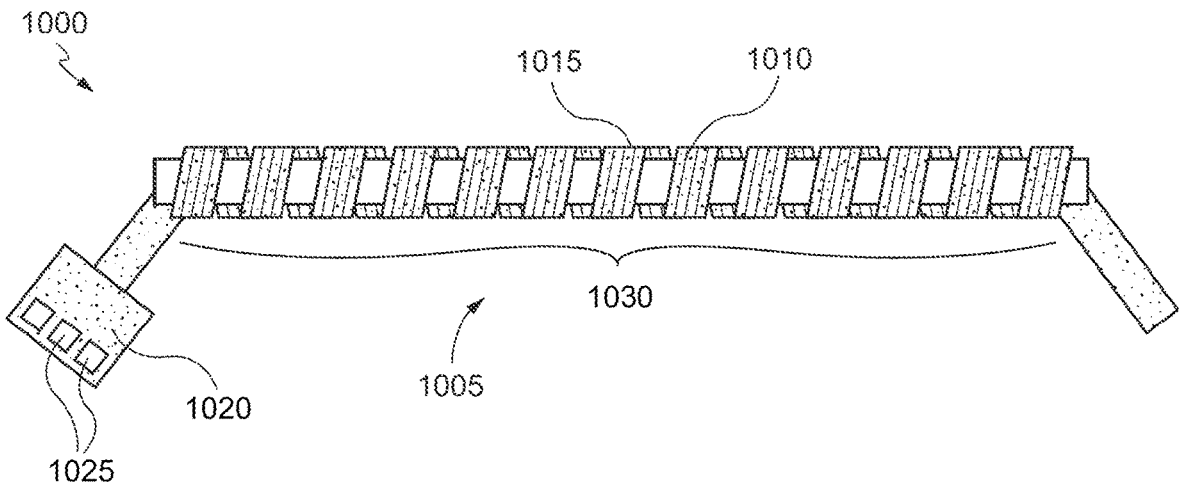
FIGS. 10A-10J show lead assembly views illustrating a method of forming a lead assembly in accordance with various embodiments.

FIGS. 10A-10J show structures and respective processing steps for fabricating an alternative thin-film lead assembly 1000 (e.g., a portion of a lead assembly encased in a housing) in accordance with various aspects of the invention. FIG. 10A shows a beginning structure 1005 for a cable including a plurality of conductive traces 1010 formed on or within a supporting structure 1015. The cable may further include an electrode assembly 1020 comprising a multi-electrode array 1025 (optionally one or more sensors) formed at a distal end of the cable 1010. The beginning structure 1005 may be formed in accordance with the processes describe herein with reference to FIGS. 8A-8F and FIGS. 9A-9C. For example, the beginning structure 1005 may be laser cut in a spiral design from a wafer or panel fabricated with electroplated traces. Thereafter, a portion of the cable may be wound into a helical pattern on a mandrel and heated to form beginning structure 1005 with a helical portion 1030.

Figure 10B:
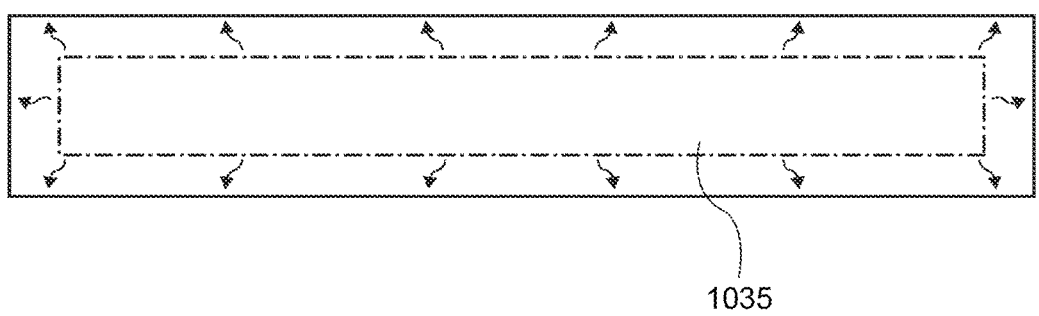

FIG. 10B shows a polymer tube 1035 being soaked in a solution and swelled to an enlarged size. In various embodiments, the polymer tube is comprised of a medical grade polymer material, for example, a soft polymer such as silicone, a polymer dispersion such as latex, or a polyurethane. In certain embodiments, the inner diameter of the polymer tube 1035 is selected to be slightly smaller (5 μm to 25 μm smaller) than the outer diameter of the helical portion 1030. For example, the inner diameter of the polymer tube 1035 may be selected to be from 375 μm to 1775 μm, from 475 μm to 1375 μm, or from 750 μm to 1275 μm, for example, about 1145 μm. The inability of medical grade polymers to expand or stretch without mechanical or chemical assistance coupled with its tacky surface makes assembly with rigid parts, such as the cable, difficult. Accordingly, the polymer tube 1035 may be soaked in a solution for predetermined amount of time to temporarily enlarge the size (e.g., the inner diameter and the outer diameter) of the polymer tube 1035 and allow for insertion of the cable into the polymer tube 1035. In some embodiments, the medical grade polymer material is a silicone. In some embodiments, the solution includes heptane. In some embodiments, the predetermined time is between three and ten minutes, for example, five minutes. In some embodiments, the size of the polymer tube 1035 is enlarged by about 15% to 45%, for example 30%.

Figure 10C:
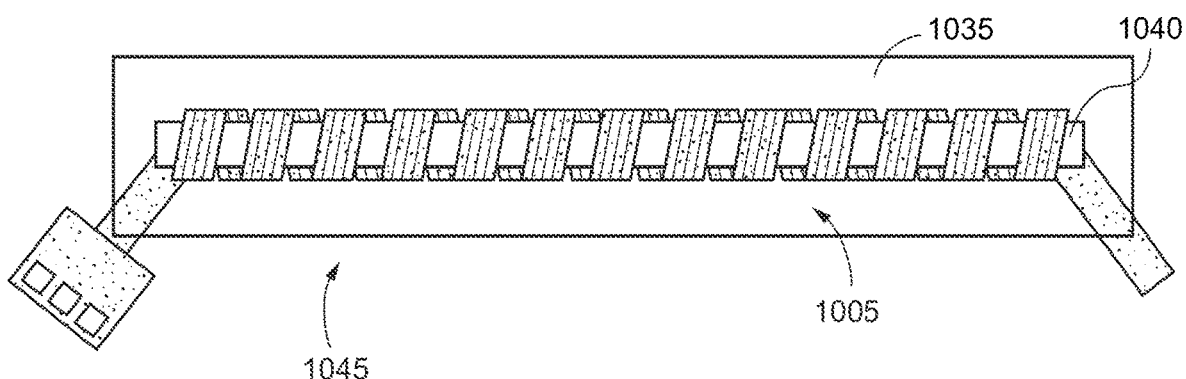
Figure 10D:
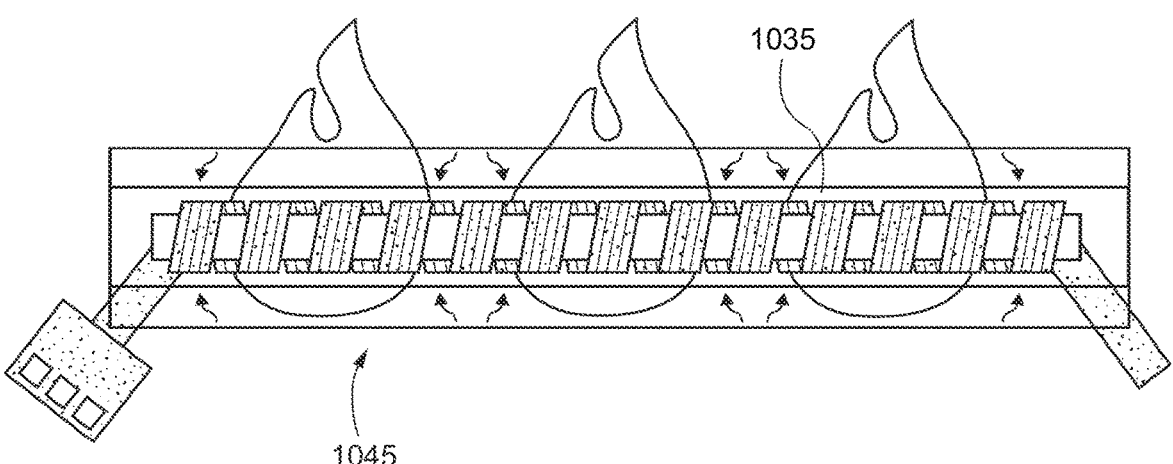
Figure 10E:
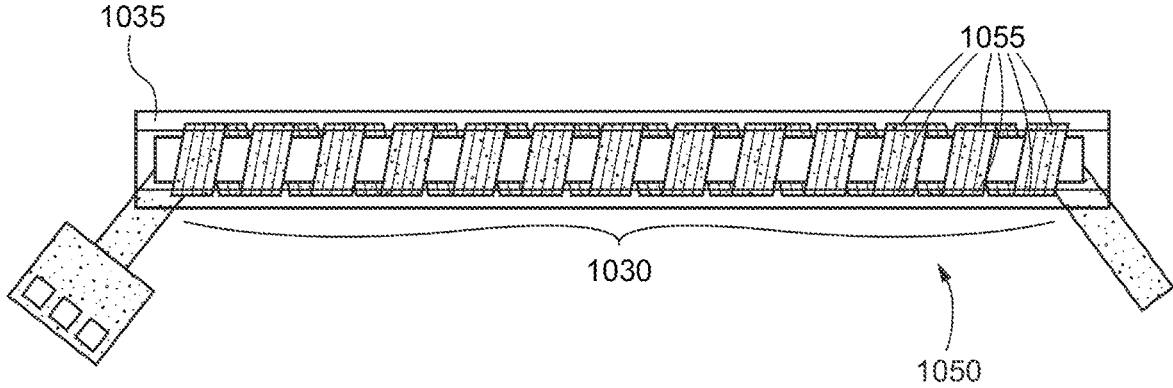

FIG. 10C shows the beginning structure 1005 on the mandrel 1040 being inserted into the enlarged polymer tube 1035 to form an intermediate structure 1045. FIG. 10D shows intermediate structure 1045 being heated to recover the original size of the polymer tube 1035. The heating process may include baking the structure in an oven, use of a heat gun, application of hot air, like methods, or any combination thereof. In various embodiments, the intermediate structure 1045 is heated at 80° C. to 115° C., for example about 100° C., for 5 to 20 minutes, for example 10 minutes. Thereafter, the intermediate structure 1045 is cooled (e.g., at ambient temperature) and the mandrel 1040 is withdrawn to obtain the intermediate structure 1050 shown in FIG. 10E. In some embodiments, the heating process results in at least a portion 1055 of the helical portion 1030 embedding into the silicone wall since the inner diameter of the polymer tube 1035 is selected to be smaller than the outer diameter of the helical portion 1030.

Figure 10F:
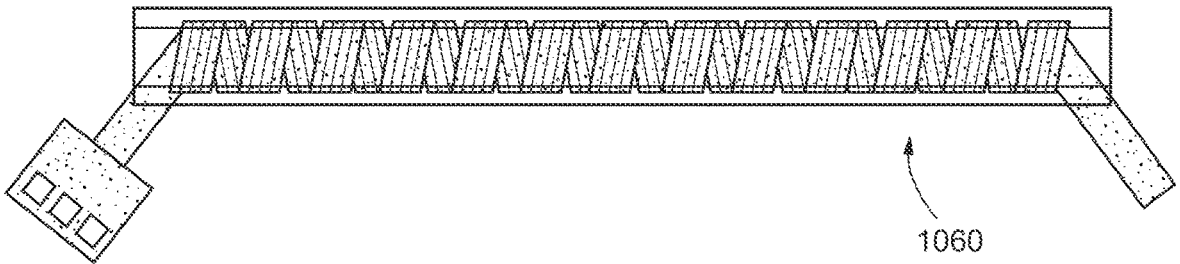
Figure 10G:
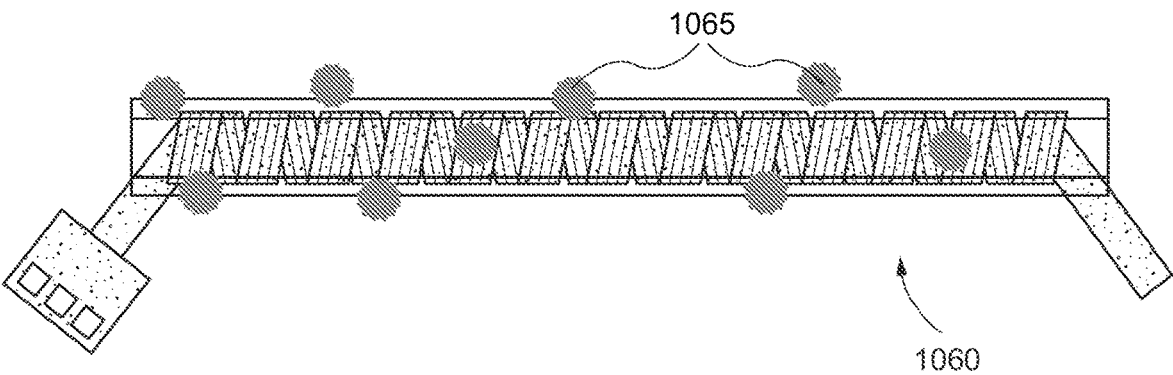
Figure 10H:
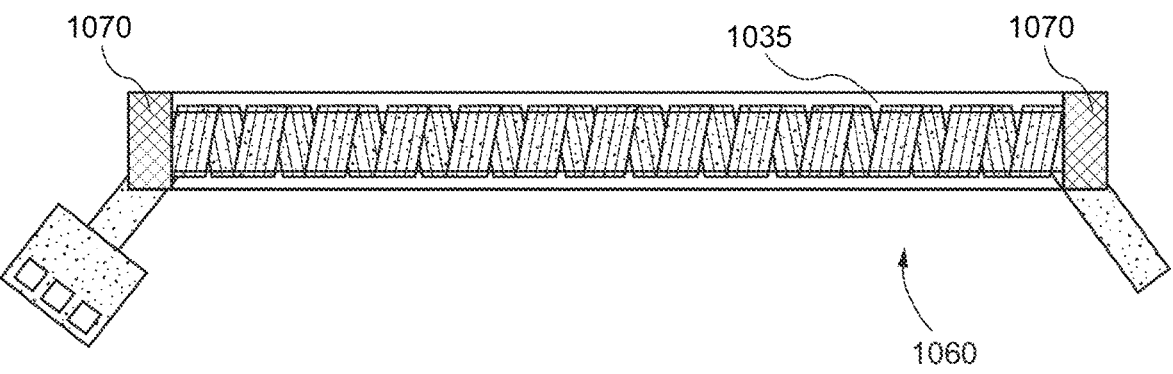
Figure 10I:
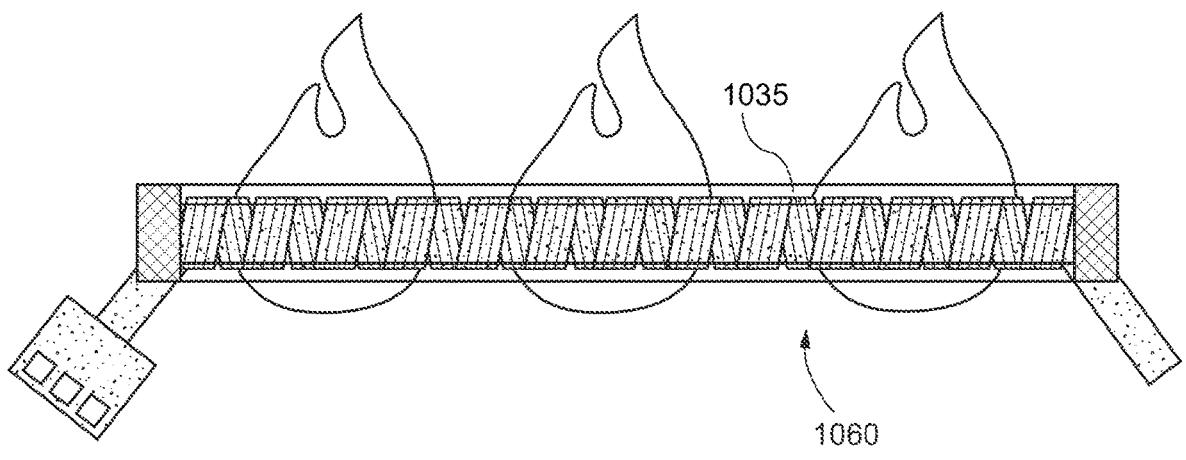
Figure 10J:
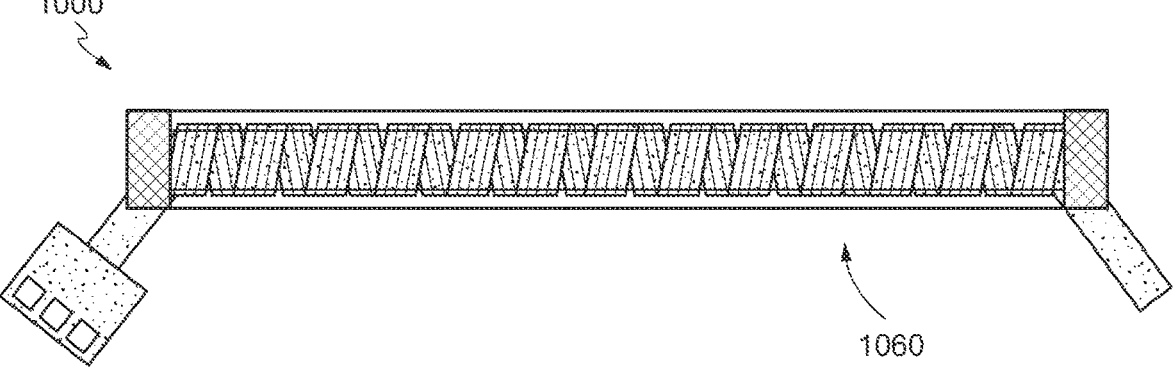

FIG. 10F shows the mandrel 1040 withdrawn from the intermediate structure 1050 to obtain the final structure 1060. Optionally, the final structure 1060 may be treated to increase wettability of the thin-film lead assembly 1000. In various embodiments, the final structure 1060 is treated with oxygen plasma 1065, as shown in FIG. 10G. The processes to provide oxygen plasma treatment to a polymer are well known in the art and thus, no further description is provided herein. Optionally, the final structure 1060 may be sealed. In various embodiments, both ends of the polymer tube 1035 are filled with liquid prepolymer 1070 (e.g., silicone liquid prepolymer), as shown in FIG. 10H. FIG. 10I shows the final structure 1060 being heated to thermally cure the liquid prepolymer on and seal the polymer tube 1035. The heating process may include baking the structure in an oven, use of a heat gun, application of hot air, like methods, or any combination thereof. In various embodiments, the final structure 1060 is heated at 80° C. to 115° C., for example about 100° C., for 5 to 20 minutes, for example 10 minutes. Thereafter, the final structure 1060 is cooled (e.g., at ambient temperature) to obtain the thin-film lead assembly 1000 shown in FIG. 10J.

Figure 11A:
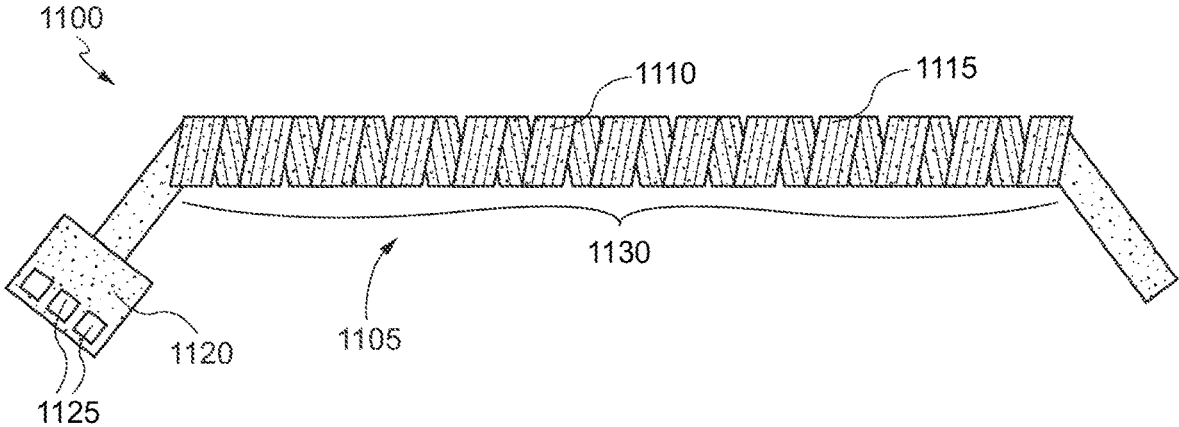
FIGS. 11A-11F show lead assembly views illustrating a method of forming a lead assembly in accordance with various embodiments.

FIGS. 11A-11F show structures and respective processing steps for fabricating an alternative thin-film lead assembly 1100 (e.g., a portion of a lead assembly embedded in a housing) in accordance with various aspects of the invention. FIG. 11A shows a beginning structure 1105 for a cable including a plurality of conductive traces 1110 formed on or within a supporting structure 1115. The cable may further include an electrode assembly 1120 comprising a multi-electrode array 1125 (optionally one or more sensors) formed at a distal end of the cable. The beginning structure 1105 may be formed in accordance with the processes describe herein with reference to FIGS. 8A-8F and FIGS. 9A-9D. For example, the beginning structure 1105 may be laser cut in a spiral design from a wafer or panel fabricated with electroplated traces. Thereafter, a portion of the cable may be wound into a helical pattern on a PTFE-coated mandrel to form beginning structure 1105 with a helical portion 1130, the beginning structure 1105 with the helical portion 1130 is then heated, and the PTFE-coated mandrel may be withdrawn.

Figure 11B:
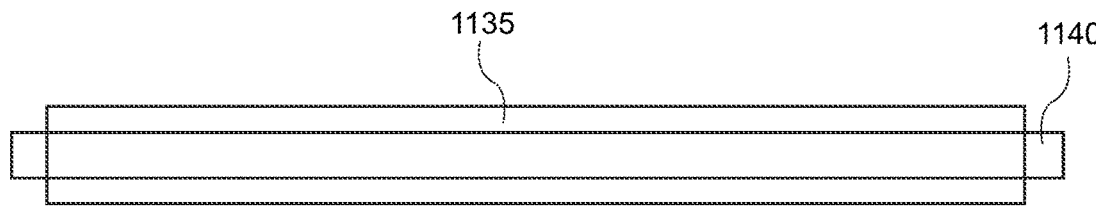

FIG. 11B shows a polymer tube 1135 inserted into a mandrel 1140. In various embodiments, the polymer tube is comprised of a medical grade polymer material, for example, a soft polymer such as silicone, a polymer dispersion such as latex, or a polyurethane. In certain embodiments, the outer diameter of the polymer tube 1135 is selected to be smaller (5 μm to 25 μm smaller) than the inner diameter of the helical portion 1130. For example, the outer diameter of the polymer tube 1135 may be selected to be from 375 μm to 1775 μm, from 475 μm to 1375 μm, or from 7750 μm to 1275 μm, for example, about 1145 μm. In some embodiments, the mandrel 1140 is the same mandrel used in the fabrications steps discussed with respect to FIGS. 9A-9C (e.g., a PTFE-coated mandrel). In some embodiments, the medical grade polymer material is a polyurethane.

Figure 11C:
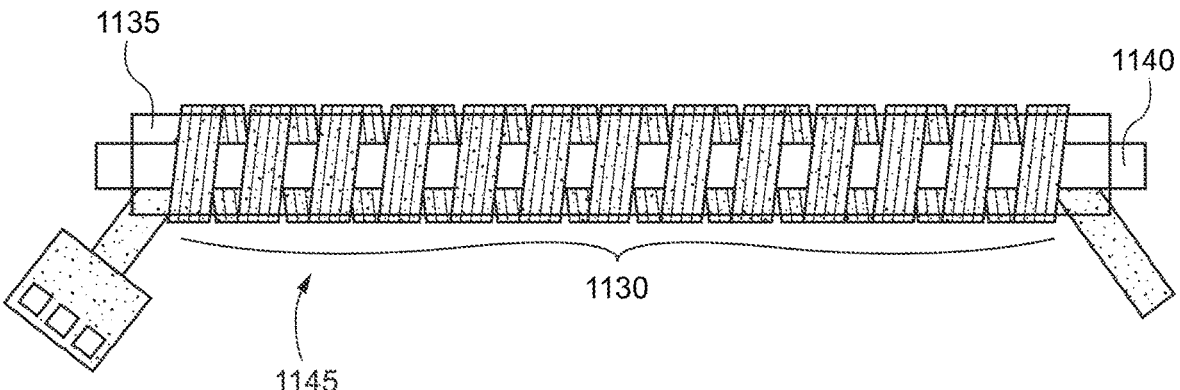
Figure 11D:
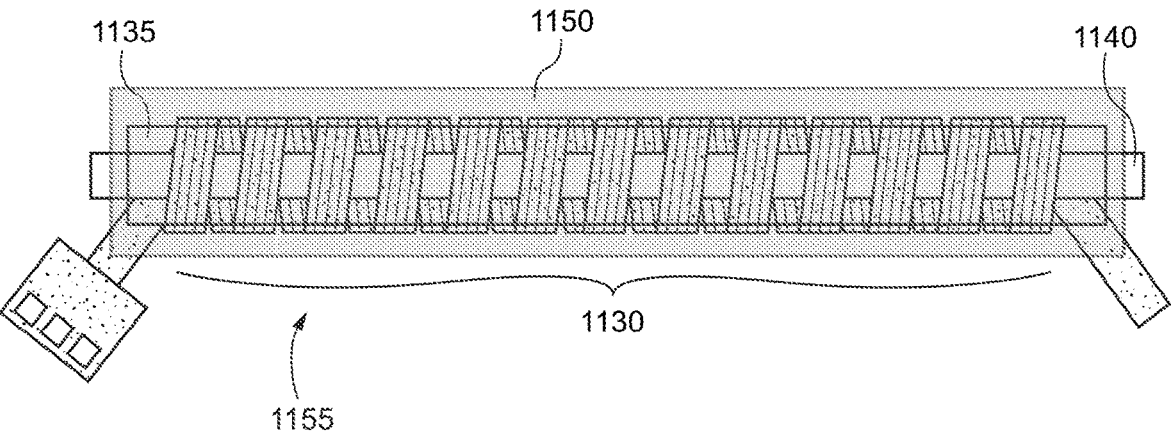
Figure 11E:
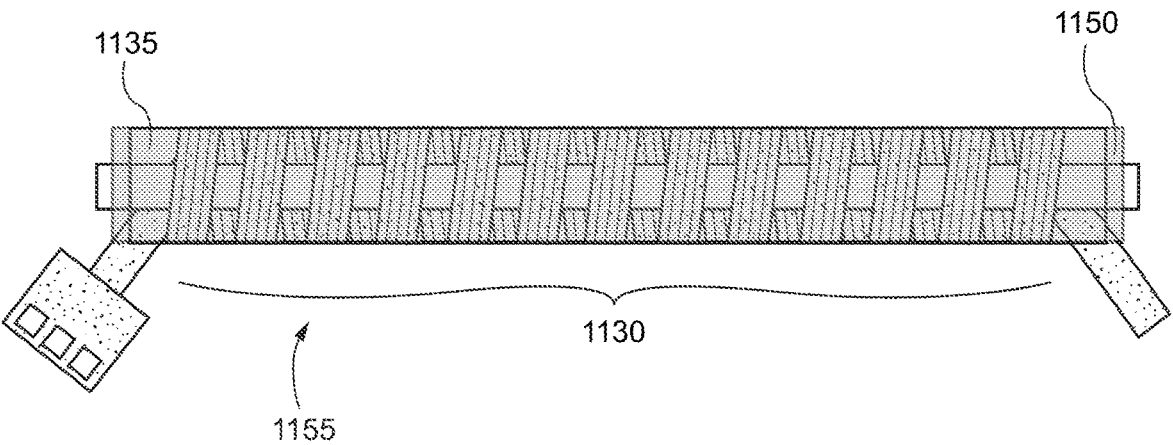
Figure 11F:
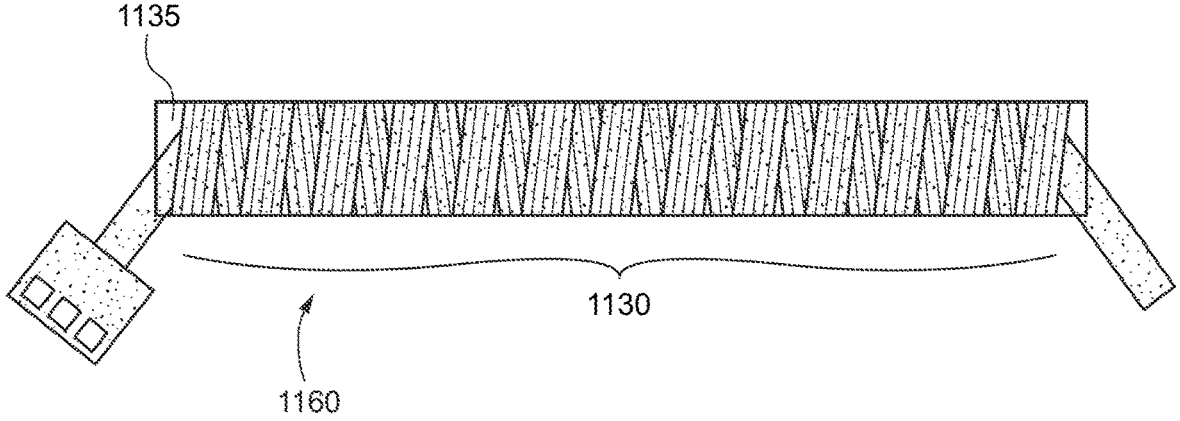

FIG. 11C shows the helical portion 1130 of the beginning structure 1105 being wrapped onto the polymer tube 1135 to form an intermediate structure 1145. FIG. 11D shows intermediate structure 1145 being inserted into a heat shrink tube 1150 to form an intermediate structure 1155. In various embodiments, the heat shrink tube is comprised of one or more polymer resins, for example, a fluoropolymer such as the FluoroPEELZ® peelable heat shrink tubes, fluorinated ethylene propylene (FEP), etc. FIG. 11E shows intermediate structure 1155 being heated to heat shrink the tube 1150 to define an outer diameter of the helical portion 1130 of the intermediate structure 1155, and at the same time melt and reflow the polymer tube 1135 to embed the helical portion 1130 in the polymer tube 1135. The heating process may include baking the structure in an oven, use of a heat gun, application of hot air, like methods, or any combination thereof. In various embodiments, the intermediate structure 1155 is heated at 170° C. to 210° C., for example about 190° C., for 15 to 40 minutes, for example 25 minutes. Thereafter, the intermediate structure 1155 is cooled (e.g., at ambient temperature), the heat shrink tube 1150 is peeled away, and the mandrel 1040 is withdrawn to obtain the final structure 1160 of the thin-film lead assembly 1100 shown in FIG. 11F. In some embodiments, the heating process embeds the helical portion 1130 into the polymer tube 1135, which results in the conductive traces 1110 and the supporting structure 1115 of the helical portion 1130 being coplanar with the polymer tube 1135. In some embodiments, the heating process results in the helical portion 1130 and the polymer tube 1135 forming a conjoined hollow tube or a conjoined tube with a lumen.

Figure 12A:
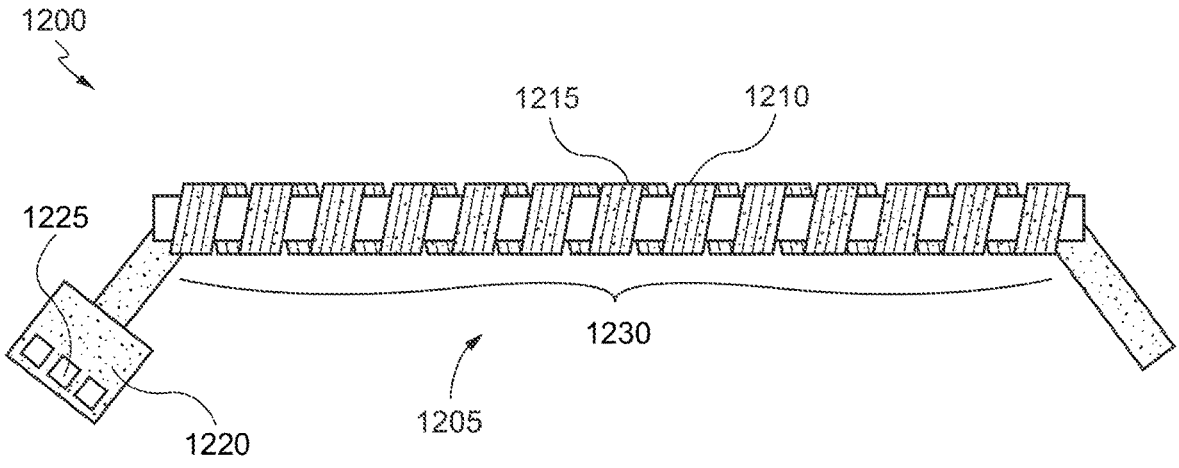

FIGS. 12A-12G show structures and respective processing steps for fabricating an alternative thin-film lead assembly 1200 (e.g., a portion of a lead assembly encased in a housing) in accordance with various aspects of the invention. FIG. 12A shows a beginning structure 1205 for a cable including a plurality of conductive traces 1210 formed on or within a supporting structure 1215. The cable may further include an electrode assembly 1220 comprising a multi-electrode array 1225 (optionally one or more sensors) formed at a distal end of the cable 1210. The beginning structure 1205 may be formed in accordance with the processes describe herein with reference to FIGS. 8A-8F and FIGS. 9A-9C. For example, the beginning structure 1205 may be laser cut in a spiral design from a wafer or panel fabricated with electroplated traces. Thereafter, a portion of the cable may be wound into a helical pattern on a mandrel and heated to form beginning structure 1205 with a helical portion 1230.

Figure 12B:
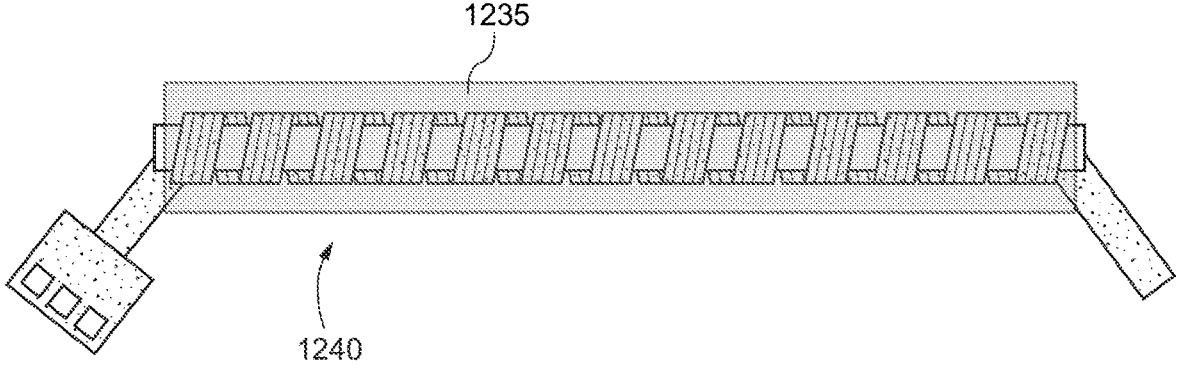
Figure 12C:
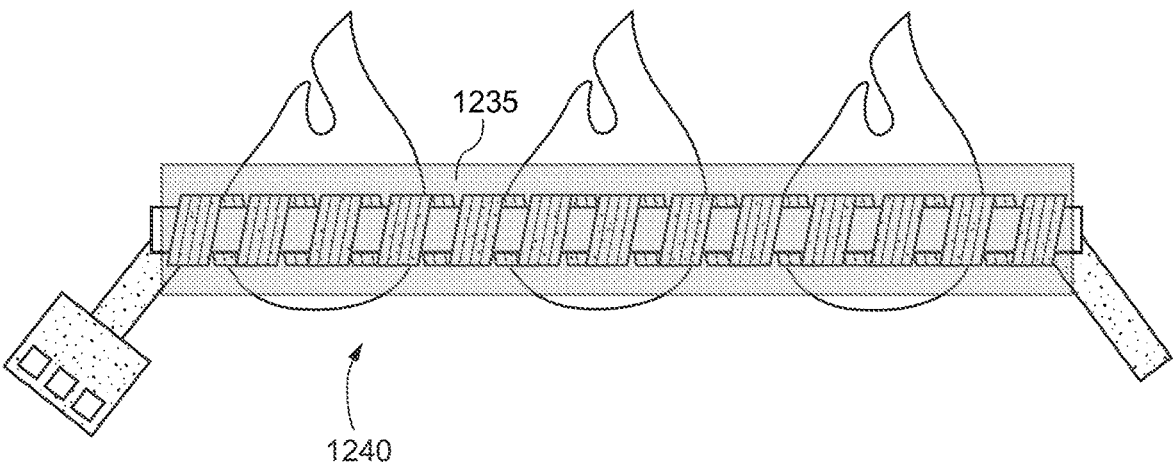
Figure 12G:
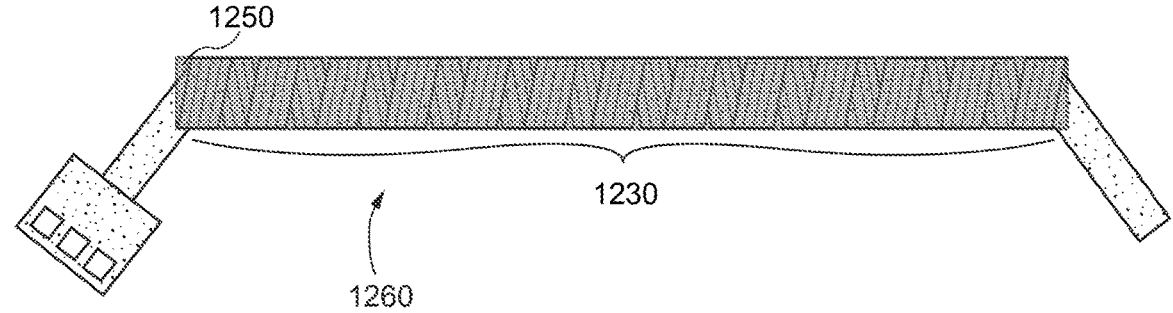

FIG. 12B shows the beginning structure 1205 being inserted into a heat shrink tube 1235 to form an intermediate structure 1240. In various embodiments, the heat shrink tube is comprised of one or more polymer resins, for example, a fluoropolymer such as the FluoroPEELZ® peelable heat shrink tubes, fluorinated ethylene propylene (FEP), etc. FIG. 12C shows intermediate structure 1240 being heated in an oven to heat shrink the tube 1235 to define an outer diameter of the helical portion 1230 of the intermediate structure 1240. The heating process may include baking the structure in an oven, use of a heat gun, application of hot air, like methods, or any combination thereof. In various embodiments, the intermediate structure 1240 is heated at 170° C. to 210° C., for example about 190° C., for 15 to 40 minutes, for example 25 minutes. Thereafter, the intermediate structure 1240 is cooled (e.g., at ambient temperature), and the mandrel is withdrawn to obtain the intermediate structure 1245 shown in FIG. 12D.

FIG. 12E shows a polymer 1250 being injected into the tube 1235 of the intermediate structure 1245. In various embodiments, the polymer is comprised of a medical grade polymer material, for example, a soft polymer such as silicone, a polyurethane, a copolymer thereof, or a blend thereof. In some embodiments, the polymer is a thermosetting polymer. In certain embodiments, the polymer is comprised of a medical grade polymer material with a Shore durometer measured on a Shore 00 Scale of less than 50 or extra soft. (Shore durometer is defined as a material's resistance to indentation). The polymer 1250 may be injected into the tube 1235 one or more times in order to fill the entire length of the tube 1235 or a portion of the length of the tube 1235 to obtain the intermediate structure 1255. FIG. 12F shows intermediate structure 1255 being heated to thermally cure (e.g., thermoset) the polymer 1250. The heating process may include heating the structure in an oven, use of a heat gun, application of hot air, like methods, or any combination thereof. In various embodiments, the intermediate structure 1255 is heated at 80° C. to 115° C., for example about 100° C., for 5 to 20 minutes, for example 10 minutes. Thereafter, the intermediate structure 1255 is cooled (e.g., at ambient temperature) and the heat shrink tube 1235 is peeled away to obtain the final structure 1260 of the thin-film lead assembly 1200 shown in FIG. 12G. In some embodiments, the injection and heating processes result in at least a portion of the helical portion 1230 embedding into the polymer 1250. In some embodiments, the injection and heating processes embeds the helical portion 1230 into the polymer 1250, which results in the conductive traces 1210 and the supporting structure 1215 of the helical portion 1230 being coplanar with the polymer 1250 (forms a housing with the polymer 1250). In some embodiments, the heating process results in the helical portion 1230 and the polymer 1250 forming a conjoined solid tube without a lumen.

Figure 13A:
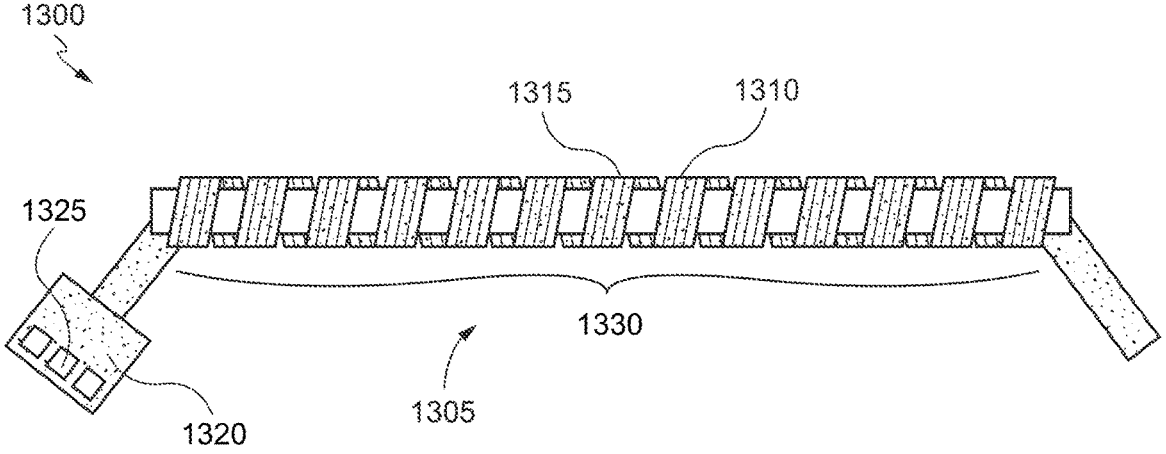
FIGS. 13A-13F show lead assembly views illustrating a method of forming a lead assembly in accordance with various embodiments.

FIGS. 13A-13F show structures and respective processing steps for fabricating an alternative thin-film lead assembly 1300 (e.g., a portion of a lead assembly encased in a housing) in accordance with various aspects of the invention. FIG. 13A shows a beginning structure 1305 for a cable including a plurality of conductive traces 1310 formed on or within a supporting structure 1315. The cable may further include an electrode assembly 1320 comprising a multi-electrode array 1325 (optionally one or more sensors) formed at a distal end of the cable 1310. The beginning structure 1305 may be formed in accordance with the processes describe herein with reference to FIGS. 8A-8F and FIGS. 9A-9C. For example, the beginning structure 1305 may be laser cut in a spiral design from a wafer or panel fabricated with electroplated traces. Thereafter, a portion of the cable may be wound into a helical pattern on a mandrel and heated to form beginning structure 1305 with a helical portion 1330.

Figure 13B:
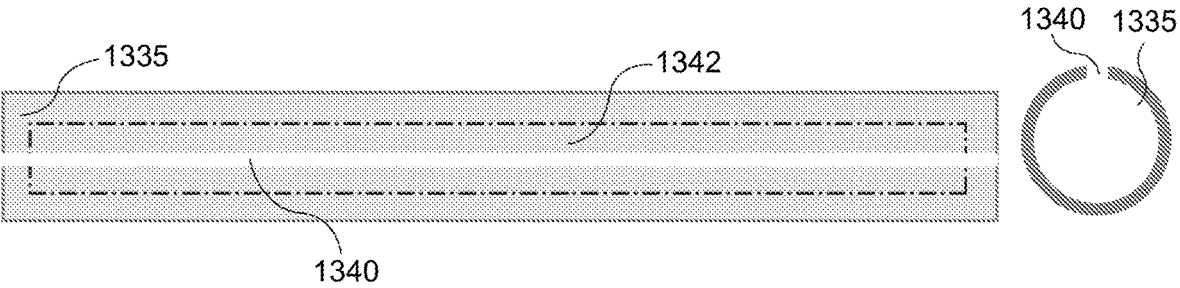

FIG. 13B shows a polymer tube 1335 having a slit 1340 cut along an entire length of the polymer tube 1335. In various embodiments, a slit 1340 is cut into the polymer tube 1335 such that a lumen 1342 of the polymer tube 1335 is exposed along an entire length of the polymer tube 1335. In some embodiments, the polymer tube is comprised of a medical grade polymer material, for example, a soft polymer such as silicone, a polymer dispersion such as latex, or a polyurethane. In certain embodiments, the inner diameter of the polymer tube 1335 is selected to be slightly larger (5 μm to 25 μm smaller) than the outer diameter of the helical portion 1330. For example, the inner diameter of the polymer tube 1335 may be selected to be from 475 μm to 2075 μm, from 575 μm to 1775 μm, or from 850 μm to 1375 μm, for example, about 1245 μm. The inability of medical grade polymers to expand or stretch without mechanical or chemical assistance coupled with its tacky surface makes assembly with rigid parts, such as the cable, difficult. Accordingly, the polymer tube 1335 has a slit 1340 cut into it to temporarily open the polymer tube 1035 and allow for insertion of the cable into the lumen 1342 of the polymer tube 1335. In some embodiments, the medical grade polymer material is a silicone.

Figure 13C:
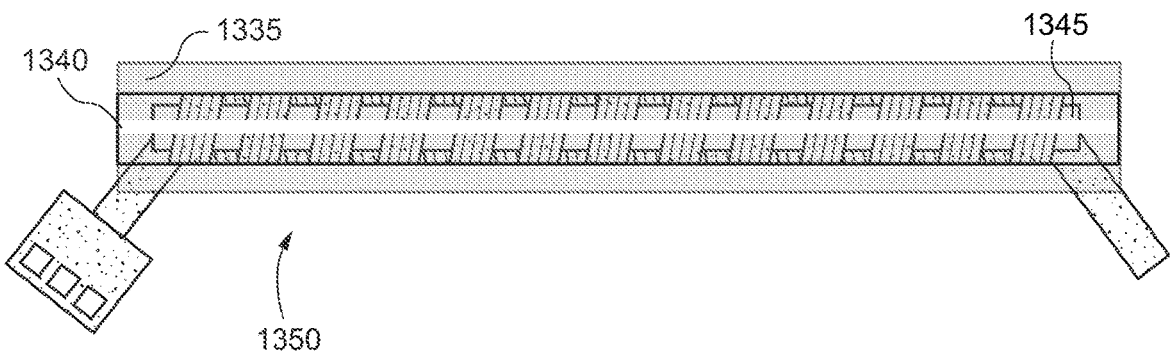
Figure 13D:
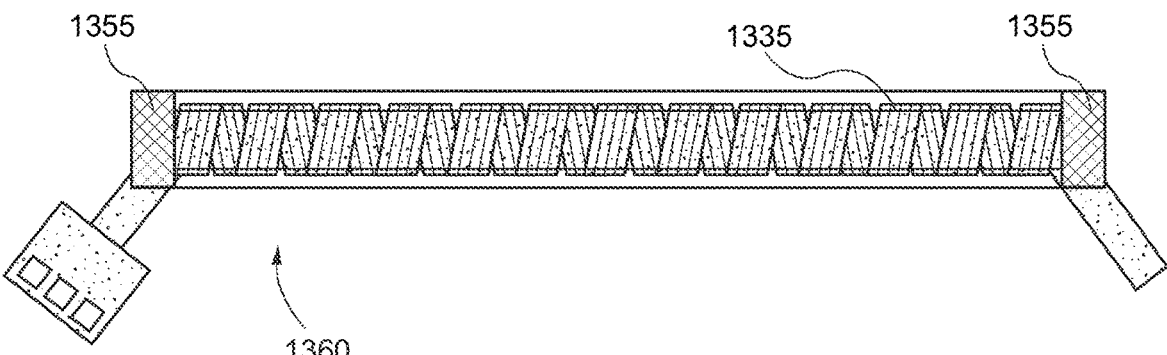
Figure 13E:
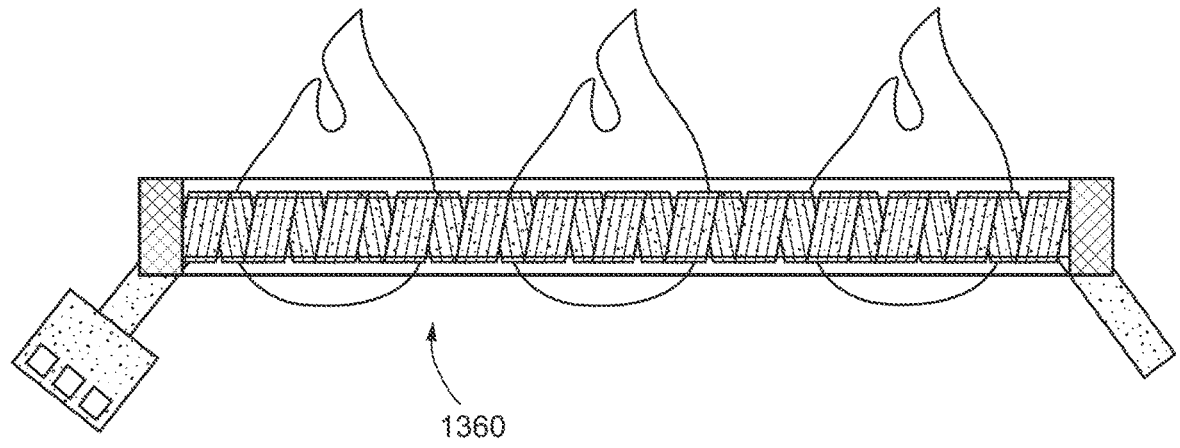
Figure 13F:
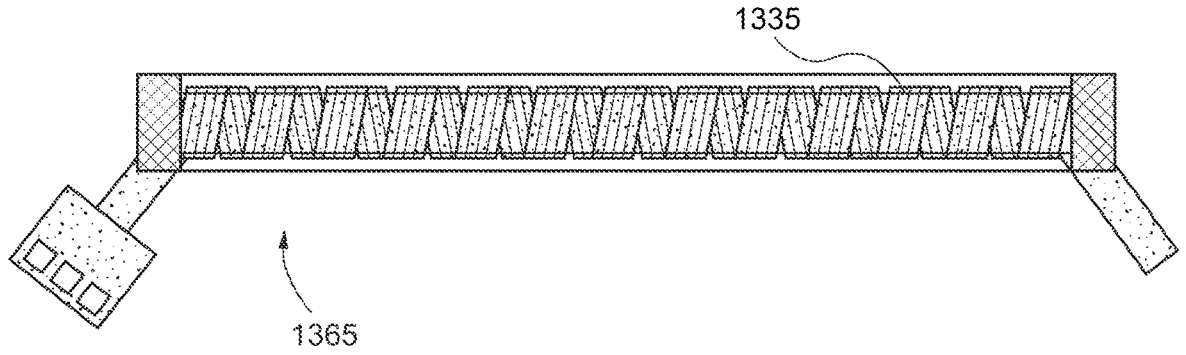

FIG. 13C shows the beginning structure 1305 on the mandrel 1345 being inserted into the slit 1340 of the polymer tube 1335 to form an intermediate structure 1350. FIG. 13D shows the mandrel 1345 withdrawn and the intermediate structure 1350 being sealed. In various embodiments, both ends of the polymer tube 1335 are filled with liquid prepolymer 1355 (e.g., silicone liquid prepolymer) to form an intermediate structure 1360. FIG. 13E shows the intermediate structure 1360 being heated to thermally cure the liquid prepolymer on and seal the polymer tube 1335. The heating process may include baking the structure in an oven, use of a heat gun, application of hot air, like methods, or any combination thereof. In various embodiments, the intermediate structure 1360 is heated at 80° C. to 115° C., for example about 100° C., for 5 to 20 minutes, for example 10 minutes. Thereafter, the intermediate structure 1360 is cooled (e.g., at ambient temperature) to obtain a final structure 1365 of the thin-film lead assembly 1300 shown in FIG. 13F. In some embodiments, the polymer tube 1335 encases (but for the slit between the sealed ends) portion of the supporting structure wound in the helical pattern. In other embodiments, the polymer tube 1335 completely encases (the slit is sealed, for example, using the liquid prepolymer) the portion of the supporting structure wound in the helical pattern.

Figure 14A:
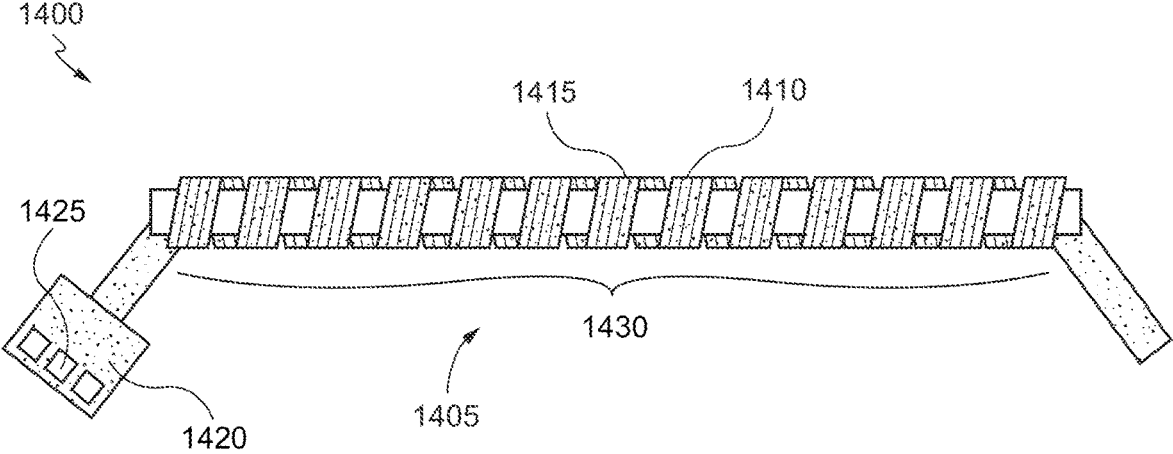
FIGS. 14A-14F show lead assembly views illustrating a method of forming a lead assembly in accordance with various embodiments.

FIGS. 14A-14F show structures and respective processing steps for fabricating an alternative thin-film lead assembly 1400 (e.g., a portion of a lead assembly encased in a housing) in accordance with various aspects of the invention. FIG. 14A shows a beginning structure 1405 for a cable including a plurality of conductive traces 1410 formed on or within a supporting structure 1415. The cable may further include an electrode assembly 1420 comprising a multi-electrode array 1425 (optionally one or more sensors) formed at a distal end of the cable 1410. The beginning structure 1405 may be formed in accordance with the processes describe herein with reference to FIGS. 8A-8F and FIGS. 9A-9D. For example, the beginning structure 1405 may be laser cut in a spiral design from a wafer or panel fabricated with electroplated traces. Thereafter, a portion of the cable may be wound into a helical pattern on a mandrel to form beginning structure 1405 with a helical portion 1430, the beginning structure 1405 with the helical portion 1430 is then heated, and the mandrel may be withdrawn.

Figure 14B:
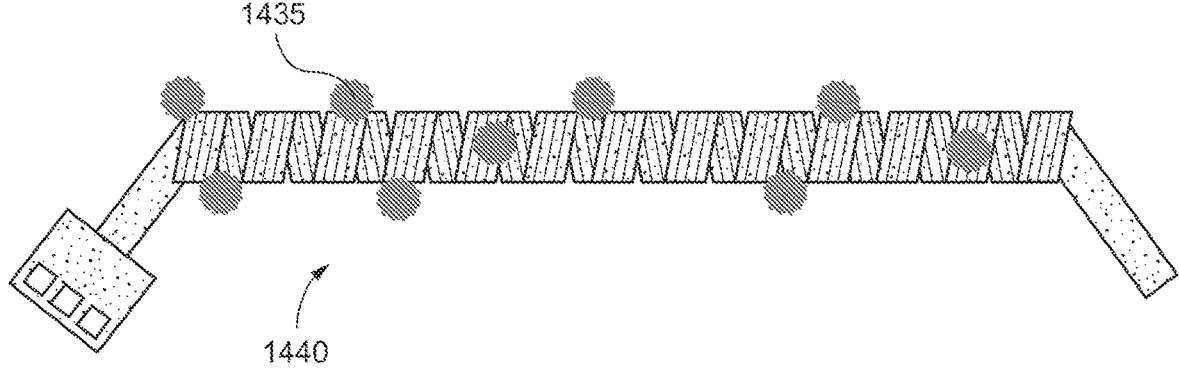

FIG. 14B shows the beginning structure 1405 is treated with oxygen plasma 1435 to form intermediate structure 1440. In various embodiments, the oxygen plasma treatment is provided to create hydroxyl groups on a surface of the supporting structure 1415. The processes to provide oxygen plasma treatment to a polymer are well known in the art and thus, no further description is provided herein.

Figure 14C:
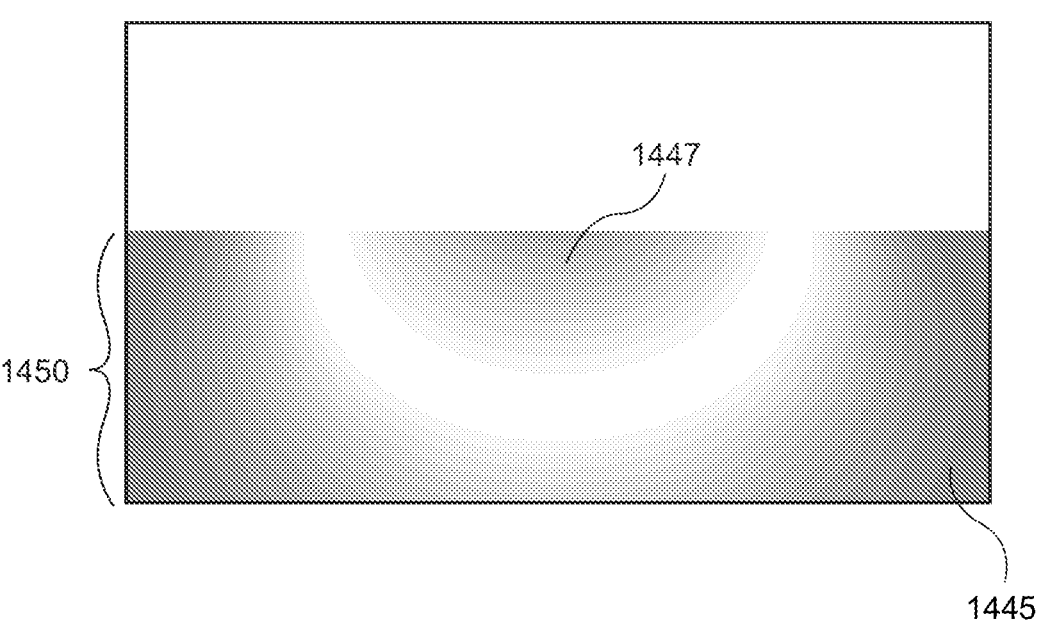

FIG. 14C shows diluting a liquid prepolymer or polymer 1445 (e.g., silicone liquid prepolymer) with a solvent 1447 to adjust the viscosity for use as a dip or spray solution 1450 in a dip coating, spin coating, or spray coating process. In various embodiments, the liquid prepolymer or polymer 1445 is comprised of silicone, a polymer dispersion, parylene, or a polyurethane. In some embodiments, the solvent is an organic solvent. In some embodiments, the solvent is a fluorinated organic solvent. In some embodiments, the fluorinated organic solvent is selected from the group consisting of: perfluoroarylalkanes, perfluoro-tert-amines, perfluoropolyethers, and hydrofluoropolyethers. In some embodiments, the fluorinated organic solvent comprises perfluoropolyether or hydrofluoropolyether. In some embodiments, the fluorinated organic solvent comprises ethoxy-nonafluorobutane. In some embodiments, the fluorinated organic solvent consists essentially of ethoxy-non-afluorobutane. The solution 1450 may be provided compris-ing the solvent at a wt % in the range from 50 to 90 wt %, more particularly from 60 to 85 wt %, for example 75 wt % based on a total weight of the dip solution. In some embodiments, the solution 1450 is provided comprising the solvent at 75 wt %.

Figure 14D:
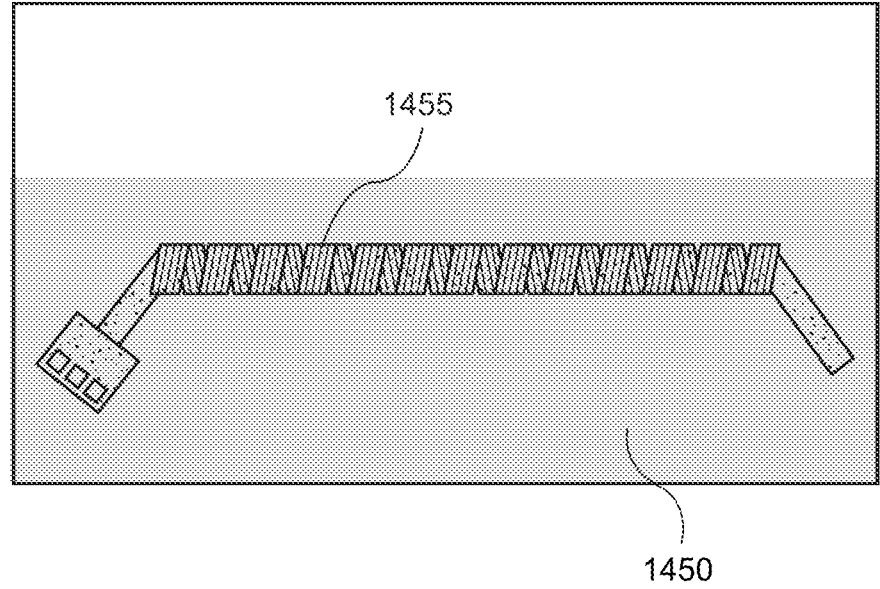

FIG. 14D shows applying the solution 1450 on the intermediate structure 1440 to form the intermediate structure 1455 comprising one or more coats of the polymer. In various embodiments, the applying comprising dip coating, pin coating, or spray coating the intermediate structure 1440 with the solution 1450 to form the intermediate structure 1455 comprising one or more coats of the polymer. In some embodiments, the dip coating process includes immersion and dwell time, deposition and drainage, and evaporation. In the first step, immersion and dwell time, the intermediate structure 1440 is immersed in the solution 1450. Sufficient time is required for the solution 1450 to interact and fully wet the intermediate structure 1440. In the second step, deposition and drainage, the intermediate structure 1440 is withdrawn from the solution 1450. The moving intermediate structure 1440 entrains the liquid polymer. The entrained thickness of the deposited polymer is related to various competing factors. For example, higher viscosity and with-draw speed result in a thicker housing; whereas surface energy and gravity drive a lower housing thickness. In the third step, evaporation, the solvent evaporates from the liquid polymer, and the viscosity of the polymer increases such that bulk flow of the polymer is no longer possible. Change in housing thickness at the third step may be facilitated by further evaporation of the solvent from the liquid polymer.

Figure 14E:
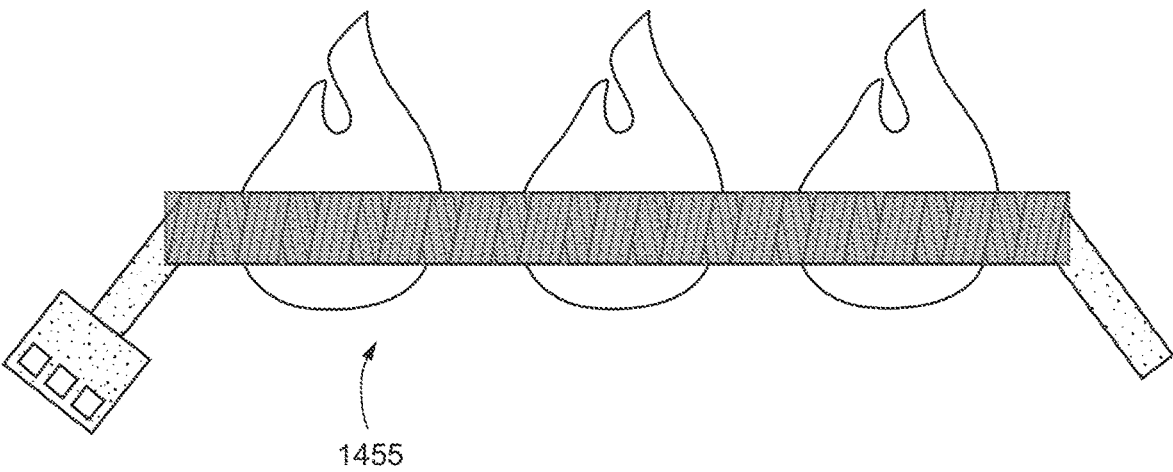
Figure 14F:
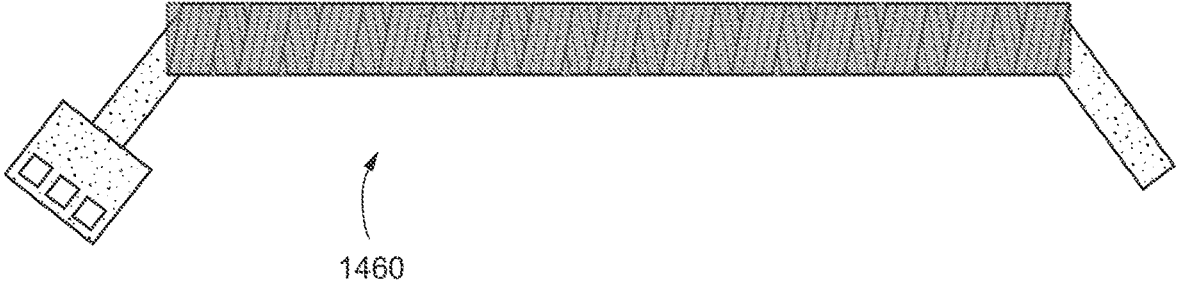

FIG. 14E shows the intermediate structure 1455 being heated to cure (e.g., thermoset) the polymer. The heating process may include baking the structure in an oven, use of a heat gun, application of hot air, like methods, or any combination thereof. In various embodiments, the interme-diate structure 1455 is heated at 80° C. to 115° C., for example about 100° C., for 5 to 20 minutes, for example 10 minutes. Thereafter, the intermediate structure 1455 is cooled (e.g., at ambient temperature) to obtain the final structure 1460 of the thin-film lead assembly 1400 shown in FIG. 14F. In some embodiments, the heating process results in at least a portion of the helical portion 1430 embedding into the polymer since the solution 1450 is capable of dispersing in between the helixes of the helical portion 1430. In some embodiments, the polymer encases the portion of the supporting structure wound in the helical pattern.

While the manufacturing processes of lead assemblies have been described at some length and with some particu-larity with respect to a specific steps, it is not intended that the processes be limited to any such particular set of steps. Instead, it should be understood the manufacturing pro-cesses described herein are exemplary embodiments, and that the manufacturing processes are to be construed with the broadest sense to include variations of the steps to meet specific design and/or performance need described herein, as well as other variations that are well known to those of skill in the art. For example, the various intermediate and final structures described may be adjusted or modified with treatments to increase wettability of the thin-film lead assembly or to seal the ends of the lumens to meet specific design and/or performance needs. Furthermore, it is to be understood that other steps have been omitted from the description of the manufacturing processes for simplicity and clarity. The omitted steps may include obtaining or fabricating the polymer tubes, obtaining or fabricating the heat shrink tubes, waiting predetermined amounts of time for curing or thermosetting, etc.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A lead assembly comprising:
a cable comprising: a proximal end, a distal end, a supporting structure that extends from the proximal end to the distal end, and a plurality of conductive traces formed on a portion of the supporting structure, wherein the supporting structure is comprised of one or more layers of dielectric material, wherein a first portion of the supporting structure at the proximal end has a first type of helical structure, and wherein a second portion of the supporting structure between the first portion and the distal end has a second type of helical structure and is completely encased in a housing; and
an interface formed on the supporting structure at the distal end of the cable, wherein the interface comprises a plurality of electrodes and/or a plurality of sensors in electrical connection with one or more conductive traces of the plurality of conductive traces,
wherein the plurality of electrodes comprise a first set of electrodes and a second set of electrodes and/or the plurality of sensors comprise a first set of sensors and a second set of sensors,
wherein the supporting structure at the distal end of the cable comprises at least one curved portion in a deployed state; and
wherein: (i) the at least one curved portion of the supporting structure is disposed between the first set of electrodes and the second set of electrodes, and/or (ii) the at least one curved portion of the supporting structure is disposed between the first set of sensors and the second set of sensors.

2. The lead assembly of claim 1, wherein the supporting structure at the distal end of the cable is thermoformed into a curved structure comprising the at least one curved portion.

3. The lead assembly of claim 2, wherein the at least one curved portion is a single curved portion and the curved structure has a shape of a "U" or a "J".

4. The lead assembly of claim 2, wherein the at least one curved portion is multiple curved portions and the curved structure has a shape of a "S", a helix, or an involute spiral.

5. The lead assembly of claim 2, wherein the plurality of conductive traces have a thickness from 0.5 µm to 100 µm.

6. The lead assembly of claim 2, wherein the cable has a spiral shape comprising two or more turns and a pitch between each of the turns from 10 µm to 1 cm.

7. The lead assembly of claim 2, wherein the plurality of conductive traces extend from the proximal end to the distal end.

8. The lead assembly of claim 2, wherein a length of the supporting structure is from 5 cm to 150 cm, and a width of the supporting structure is from 25 µm to 5 mm.

9. The lead assembly of claim 2, wherein the dielectric material is polyimide, liquid crystal polymer, parylene, polyether ether ketone, or a combination thereof.

10. The lead assembly of claim 2, wherein the plurality of conductive traces are comprised of one or more layers of conductive material, and the conductive material is copper (Cu), gold (Au), silver (Ag), gold/chromium (Au/Cr), platinum (Pt), platinum/iridium (Pt/Ir), titanium (Ti), gold/titanium (Au/Ti), or any alloy thereof.

11. The lead assembly of claim 2, wherein a coefficient of thermal expansion for the plurality of conductive traces is approximately equal to a coefficient of thermal expansion for the supporting structure.

12. The lead assembly of claim 2, further comprising a multiplexer chip formed on the supporting structure at the proximal end or the distal end, the multiplexer chip in electrical connection with the plurality of electrodes and/or the plurality of sensors via the plurality of conductive traces.

13. A method for deploying a monolithic thin-film lead assembly, comprising:
obtaining the lead assembly comprising:
a cable comprising: a proximal end, a distal end, a supporting structure that extends from the proximal end to the distal end, and a plurality of conductive traces formed on a portion of the supporting structure, wherein the supporting structure is comprised of one or more layers of dielectric material, wherein a first portion of the supporting structure at the proximal end has a first type of helical structure, and wherein a second portion of the supporting structure between the first portion and the distal end has a second type of helical structure and is completely encased in a housing;
an interface formed on the supporting structure at the distal end of the cable, wherein the interface comprises a plurality of electrodes and/or a plurality of sensors in electrical connection with one or more conductive traces of the plurality of conductive traces, wherein the plurality of electrodes comprise a first set of electrodes and a second set of electrodes and/or the plurality of sensors comprise a first set of sensors and a second set of sensors; and
a guidewire comprising a stylet inserted through the interface, wherein while the stylet is inserted through the interface, the interface has a first profile, and wherein the first profile is straight with the first set of electrodes and the second set of electrodes and/or the first set of sensors and the second set of sensors provided in a linear array;
inserting, with the guidewire, the lead assembly into a cavity of a subject;
moving, with the guidewire, the lead assembly through the cavity to position the interface at a target location; and
removing the guidewire and stylet from the cavity while leaving the lead assembly in place with the interface positioned at the target location, wherein removal of the stylet from the interface allows for the interface to take a second profile having at least one curved portion, wherein: (i) the at least one curved portion is disposed between the first set of electrodes and the second set of electrodes, and/or (ii) the at least one curved portion is disposed between the first set of sensors and the second set of sensors.

14. The method of claim 13, wherein the at least one curved portion is a single curved portion and the curved structure has a shape of a "U" or a "J".

15. The method of claim 13, wherein the at least one curved portion is multiple curved portions and the curved structure has a shape of a "S", a helix, or an involute spiral.

16. The method of claim 13, further comprising: connecting the cable to a computing device and using the computing device to send a single through the interface to tissue at the target location or receive a signal from the tissue at the target location.

* * * * *